United States Patent
Cavanagh et al.

(10) Patent No.: US 10,039,348 B2
(45) Date of Patent: *Aug. 7, 2018

(54) TENSION LIMITING MECHANISMS FOR CLOSURE DEVICES AND METHODS THEREFOR

(71) Applicant: Boa Technology Inc., Denver, CO (US)

(72) Inventors: Sean Cavanagh, Bend, OR (US); Michael Nickel, Golden, CO (US); Jesse Cotterman, Evergreen, CO (US); Eric Irwin, Denver, CO (US); Brett Vladika, Golden, CO (US); Randon Kruse, Denver, CO (US); Mark Soderberg, Conifer, CO (US); Christopher Converse, Boulder, CO (US); Adam Auell, Morrison, CO (US)

(73) Assignee: Boa Technology Inc., Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/489,530

(22) Filed: Apr. 17, 2017

(65) Prior Publication Data
US 2017/0303644 A1    Oct. 26, 2017

Related U.S. Application Data

(63) Continuation of application No. 14/322,690, filed on Jul. 2, 2014, now Pat. No. 9,629,417.
(Continued)

(51) Int. Cl.
*A43C 11/00* (2006.01)
*A43C 11/20* (2006.01)
(Continued)

(52) U.S. Cl.
CPC ............ *A43C 11/20* (2013.01); *A43C 11/165* (2013.01); *A61F 5/028* (2013.01); *Y10T 24/2183* (2015.01); *Y10T 29/4984* (2015.01)

(58) Field of Classification Search
CPC ....... A61F 5/028; A43C 11/16; A43C 11/165; Y10T 24/2158; Y10T 24/2164
(Continued)

(56) References Cited

U.S. PATENT DOCUMENTS

| 59,332 A | 10/1866 | White et al. |
| 80,834 A | 8/1868 | Prussia |

(Continued)

FOREIGN PATENT DOCUMENTS

| CA | 2112789 | 8/1994 |
| CA | 2114387 | 8/1994 |

(Continued)

OTHER PUBLICATIONS

U.S. Appl. No. 09/956,601, filed Sep. 18, 2001, Hammerslag.
(Continued)

*Primary Examiner* — Jason W San
(74) *Attorney, Agent, or Firm* — Kilpatrick Townsend & Stockton LLP

(57) ABSTRACT

According to an embodiment, a device for tightening an article includes a housing having an interior region and a spool positioned within the interior region and rotatable relative thereto. A tightening mechanism is operably coupled with the spool to cause the spool to rotate within the interior region of the housing. A tension member is coupled with the spool and is configured to be tensioned upon rotation of the spool via the tightening mechanism. The device also includes a tension limiting mechanism that allows the tension member to be tensioned via the tightening mechanism until a tension threshold is achieved. After the tension threshold is achieved, further operation of the tightening mechanism does not substantially tension the tension member due to the tension limiting mechanism.

23 Claims, 49 Drawing Sheets

Related U.S. Application Data

(60) Provisional application No. 61/842,238, filed on Jul. 2, 2013.

(51) Int. Cl.
*A43C 11/16* (2006.01)
*A61F 5/02* (2006.01)

(58) Field of Classification Search
USPC ............................................. 24/68 SK
See application file for complete search history.

(56) References Cited

U.S. PATENT DOCUMENTS

| | | | |
|---|---|---|---|
| 117,530 A | 8/1871 | Foote | |
| 228,946 A | 6/1880 | Schulz | |
| 230,759 A | 8/1880 | Drummond | |
| 301,854 A | 7/1884 | Buch | |
| 371,394 A | 10/1887 | Warren | |
| 379,113 A | 3/1888 | Hibberd | |
| 460,743 A | 10/1891 | Dickson, Jr. | |
| 886,779 A | 5/1908 | Dunstan | |
| 908,704 A | 1/1909 | Sprinkle | |
| 1,060,422 A | 4/1913 | Bowdish | |
| 1,062,511 A | 5/1913 | Short | |
| 1,083,775 A | 1/1914 | Thomas | |
| 1,090,438 A | 3/1914 | Worth et al. | |
| 1,170,472 A | 2/1916 | Barber | |
| 1,288,859 A | 12/1918 | Feller et al. | |
| 1,390,991 A | 9/1921 | Fotchuk | |
| 1,393,188 A | 10/1921 | Whiteman | |
| 1,412,486 A | 4/1922 | Paine | |
| 1,416,203 A | 5/1922 | Hobson | |
| 1,429,657 A | 9/1922 | Trawinski | |
| 1,466,673 A | 9/1923 | Solomon et al. | |
| 1,469,661 A | 10/1923 | Tosuke | |
| 1,481,903 A | 1/1924 | Hart | |
| 1,502,919 A | 7/1924 | Seib | |
| 1,505,430 A | 8/1924 | Thomas | |
| 1,530,713 A | 3/1925 | Clark | |
| 1,548,407 A | 8/1925 | Chisholm | |
| 1,862,047 A | 6/1932 | Boulet et al. | |
| 1,995,243 A | 3/1935 | Clarke | |
| 2,088,851 A | 8/1937 | Gantenbein | |
| 2,109,751 A | 3/1938 | Matthias et al. | |
| 2,124,310 A | 7/1938 | Murr, Jr. | |
| 2,316,102 A | 4/1943 | Preston | |
| 2,353,562 A * | 7/1944 | Hatcher | B64D 1/22 |
| | | | 254/346 |
| 2,539,026 A | 1/1951 | Mangold | |
| 2,611,940 A | 9/1952 | Cairns | |
| 2,673,381 A | 3/1954 | Dueker | |
| 2,893,090 A | 7/1959 | Pagoda | |
| 2,907,086 A | 10/1959 | Ord | |
| 2,991,523 A | 7/1961 | Conte | |
| 3,028,602 A | 4/1962 | Miller | |
| 3,035,319 A | 5/1962 | Wolff | |
| 3,106,003 A | 10/1963 | Herdman | |
| 3,112,545 A | 12/1963 | Williams | |
| 3,122,810 A | 3/1964 | Lawrence et al. | |
| 3,163,900 A | 1/1965 | Martin | |
| D200,394 S | 2/1965 | Hakim | |
| 3,169,325 A | 2/1965 | Fesl | |
| 3,193,950 A | 7/1965 | Shu-Lien | |
| 3,197,155 A | 7/1965 | Chow | |
| 3,221,384 A | 12/1965 | Aufenacker | |
| 3,276,090 A | 10/1966 | Nigon | |
| D206,146 S | 11/1966 | Hendershot | |
| 3,345,707 A | 10/1967 | Rita | |
| D210,649 S | 4/1968 | Getgay | |
| 3,401,437 A | 9/1968 | Christpohersen | |
| 3,430,303 A | 3/1969 | Perrin et al. | |
| 3,491,465 A | 1/1970 | Martin | |
| 3,545,106 A | 12/1970 | Martin | |
| 3,618,232 A | 11/1971 | Shnuriwsky | |
| 3,668,791 A | 6/1972 | Salzman et al. | |
| 3,678,539 A | 7/1972 | Graup | |
| 3,703,775 A | 11/1972 | Gatti | |
| 3,729,779 A | 5/1973 | Porth | |
| 3,738,027 A | 6/1973 | Schoch | |
| 3,793,749 A | 2/1974 | Gertsch et al. | |
| 3,808,644 A | 5/1974 | Schoch | |
| 3,845,575 A | 11/1974 | Boden | |
| 3,934,346 A | 1/1976 | Sasaki et al. | |
| 3,975,838 A | 8/1976 | Martin | |
| 3,998,429 A * | 12/1976 | Cheung | F16H 7/08 |
| | | | 254/216 |
| 4,084,267 A | 4/1978 | Zadina | |
| 4,130,949 A | 12/1978 | Seidel | |
| 4,142,307 A | 3/1979 | Martin | |
| 4,227,322 A | 10/1980 | Annovi | |
| 4,261,081 A | 4/1981 | Lott | |
| 4,267,622 A | 5/1981 | Burnett-Johnston | |
| RE31,052 E | 10/1982 | Adams | |
| 4,394,803 A | 7/1983 | Goldstein | |
| 4,417,703 A | 11/1983 | Weinhold | |
| 4,433,456 A | 2/1984 | Baggio | |
| 4,463,761 A | 8/1984 | Pols et al. | |
| 4,480,395 A | 11/1984 | Schoch | |
| 4,507,878 A | 4/1985 | Semouha | |
| 4,516,576 A | 5/1985 | Kirchner | |
| 4,551,932 A | 11/1985 | Schoch | |
| 4,555,830 A | 12/1985 | Petrini et al. | |
| 4,574,500 A | 3/1986 | Aldinio et al. | |
| 4,616,432 A | 10/1986 | Bunch et al. | |
| 4,616,524 A | 10/1986 | Biodia | |
| 4,619,057 A | 10/1986 | Sartor et al. | |
| 4,620,378 A | 11/1986 | Sartor | |
| 4,631,839 A | 12/1986 | Bonetti et al. | |
| 4,631,840 A | 12/1986 | Gamm | |
| 4,633,599 A * | 1/1987 | Morell | A43C 11/16 |
| | | | 24/68 SK |
| 4,644,938 A | 2/1987 | Yates et al. | |
| 4,654,985 A | 4/1987 | Chalmers | |
| 4,660,300 A * | 4/1987 | Morell | A43C 11/16 |
| | | | 24/68 SK |
| 4,660,302 A | 4/1987 | Arieh et al. | |
| 4,680,878 A | 7/1987 | Pozzobon et al. | |
| 4,719,670 A | 1/1988 | Kurt | |
| 4,719,709 A | 1/1988 | Vaccari | |
| 4,719,710 A | 1/1988 | Pozzobon | |
| 4,722,477 A | 2/1988 | Floyd | |
| 4,741,115 A | 5/1988 | Pozzobon | |
| 4,748,726 A * | 6/1988 | Schoch | A43C 11/16 |
| | | | 24/68 B |
| 4,760,653 A | 8/1988 | Baggio | |
| 4,780,969 A | 11/1988 | White, Jr. | |
| 4,787,124 A | 11/1988 | Pozzobon et al. | |
| 4,790,081 A | 12/1988 | Benoit et al. | |
| 4,796,829 A | 1/1989 | Pozzobon et al. | |
| 4,799,297 A | 1/1989 | Baggio et al. | |
| 4,802,291 A | 2/1989 | Sartor | |
| 4,811,503 A | 3/1989 | Iwama | |
| 4,826,098 A | 5/1989 | Pozzobon et al. | |
| 4,841,649 A | 6/1989 | Baggio et al. | |
| 4,856,207 A | 8/1989 | Datson | |
| 4,862,878 A | 9/1989 | Davison | |
| 4,870,723 A | 10/1989 | Pozzobon et al. | |
| 4,870,761 A | 10/1989 | Tracy | |
| 4,884,760 A | 12/1989 | Baggio et al. | |
| 4,901,938 A | 2/1990 | Cantley et al. | |
| 4,924,605 A | 5/1990 | Spademan | |
| D308,282 S | 6/1990 | Bergman et al. | |
| 4,937,953 A | 7/1990 | Walkhoff | |
| 4,961,544 A | 10/1990 | Biodia | |
| 4,974,299 A | 12/1990 | Moon | |
| 4,979,953 A | 12/1990 | Spence | |
| 4,989,805 A | 2/1991 | Burke | |
| 5,001,817 A | 3/1991 | De Bortoli et al. | |
| 5,016,327 A | 5/1991 | Klausner | |
| 5,042,177 A | 8/1991 | Schoch | |
| 5,062,225 A | 11/1991 | Gorza | |
| 5,065,480 A | 11/1991 | DeBortoli | |
| 5,065,481 A | 11/1991 | Walkhoff | |

(56) References Cited

U.S. PATENT DOCUMENTS

| | | |
|---|---|---|
| 5,108,216 A | 4/1992 | Geyer et al. |
| 5,117,567 A | 6/1992 | Berger |
| 5,152,038 A | 10/1992 | Schoch |
| 5,157,813 A | 10/1992 | Carroll |
| 5,158,428 A | 10/1992 | Gessner et al. |
| 5,177,882 A | 1/1993 | Berger |
| 5,181,331 A | 1/1993 | Berger |
| 5,184,378 A | 2/1993 | Batra |
| D333,552 S | 3/1993 | Berger et al. |
| 5,205,055 A | 4/1993 | Harrell |
| 5,233,767 A | 8/1993 | Kramer |
| 5,249,377 A | 10/1993 | Walkhoff |
| 5,259,094 A | 11/1993 | Zepeda |
| 5,315,741 A | 5/1994 | Debberke |
| 5,319,868 A | 6/1994 | Hallenbeck |
| 5,319,869 A | 6/1994 | McDonald et al. |
| 5,325,613 A | 7/1994 | Sussmann |
| 5,327,662 A | 7/1994 | Hallenbeck |
| 5,333,398 A | 8/1994 | Seo |
| 5,335,401 A | 8/1994 | Hanson |
| 5,341,583 A | 8/1994 | Hallenbeck |
| 5,345,697 A | 9/1994 | Quellais |
| 5,355,596 A | 10/1994 | Sussmann |
| 5,357,654 A | 10/1994 | Hsing-Chi |
| 5,371,957 A | 12/1994 | Gaudio |
| 5,381,609 A | 1/1995 | Hieblinger |
| 5,392,535 A | 2/1995 | Van Noy et al. |
| D357,576 S | 4/1995 | Steinweis |
| 5,425,161 A | 6/1995 | Schoch |
| 5,425,185 A | 6/1995 | Gansler |
| 5,430,960 A | 7/1995 | Richardson |
| 5,433,648 A | 7/1995 | Frydman |
| 5,463,822 A | 11/1995 | Miller |
| 5,477,593 A | 12/1995 | Leick |
| D367,755 S | 3/1996 | Jones |
| D367,954 S | 3/1996 | Dion |
| 5,502,902 A | 4/1996 | Sussmann |
| 5,511,325 A | 4/1996 | Hieblinger |
| 5,526,585 A | 6/1996 | Brown et al. |
| 5,535,531 A | 7/1996 | Karabed et al. |
| 5,537,763 A | 7/1996 | Donnadieu et al. |
| 5,557,864 A | 9/1996 | Marks |
| 5,566,474 A | 10/1996 | Leick et al. |
| D375,831 S | 11/1996 | Perry |
| 5,596,820 A | 1/1997 | Edauw et al. |
| 5,599,000 A | 2/1997 | Bennett |
| 5,599,288 A | 2/1997 | Shirley et al. |
| 5,600,874 A | 2/1997 | Jungkind |
| 5,606,778 A * | 3/1997 | Jungkind ............... A43C 11/16 24/68 SK |
| 5,607,448 A | 3/1997 | Stahl et al. |
| D379,113 S | 5/1997 | McDonald et al. |
| 5,638,588 A | 6/1997 | Jungkind |
| 5,640,785 A | 6/1997 | Egelja |
| 5,647,104 A | 7/1997 | James |
| 5,651,198 A | 7/1997 | Sussmann |
| 5,669,116 A | 9/1997 | Jungkind |
| 5,692,319 A | 12/1997 | Parker et al. |
| 5,718,021 A | 2/1998 | Tatum |
| 5,718,065 A | 2/1998 | Locker |
| 5,720,084 A | 2/1998 | Chen |
| 5,732,483 A | 3/1998 | Cagliari |
| 5,732,648 A | 3/1998 | Aragon |
| 5,736,696 A | 4/1998 | Del Rosso |
| 5,737,854 A | 4/1998 | Sussmann |
| 5,755,044 A | 5/1998 | Veylupek |
| 5,756,298 A | 5/1998 | Burczak |
| 5,761,777 A | 6/1998 | Leick |
| 5,772,146 A | 6/1998 | Kawamoto et al. |
| 5,784,809 A | 7/1998 | McDonald |
| 5,791,068 A | 8/1998 | Bernier et al. |
| 5,819,378 A | 10/1998 | Doyle |
| 5,833,640 A | 11/1998 | Vazquez, Jr. et al. |
| 5,839,210 A | 11/1998 | Bernier et al. |
| 5,845,371 A | 12/1998 | Chen |
| 5,906,057 A | 5/1999 | Borsoi |
| 5,909,946 A | 6/1999 | Okajima |
| D413,197 S | 8/1999 | Faye |
| 5,934,599 A | 8/1999 | Hammerslag |
| 5,937,542 A | 8/1999 | Bourdeau |
| 5,956,823 A | 9/1999 | Borel |
| 5,971,946 A | 10/1999 | Quinn et al. |
| 6,015,110 A * | 1/2000 | Lai ........................ B65H 75/28 242/388.1 |
| 6,038,791 A | 3/2000 | Cornelius et al. |
| 6,052,921 A | 4/2000 | Oreck |
| 6,070,886 A | 6/2000 | Cornelius et al. |
| 6,070,887 A | 6/2000 | Cornelius et al. |
| 6,083,857 A | 7/2000 | Bottger |
| 6,088,936 A | 7/2000 | Bahl |
| 6,102,412 A | 8/2000 | Staffaroni |
| D430,724 S | 9/2000 | Matis et al. |
| 6,119,318 A | 9/2000 | Maurer |
| 6,119,372 A | 9/2000 | Okajima |
| 6,128,835 A | 10/2000 | Ritter et al. |
| 6,128,836 A | 10/2000 | Barret |
| 6,148,489 A | 11/2000 | Dickie et al. |
| 6,202,953 B1 | 3/2001 | Hammerslag |
| 6,219,891 B1 | 4/2001 | Maurer et al. |
| 6,240,657 B1 | 6/2001 | Weber et al. |
| 6,256,798 B1 | 7/2001 | Egolf et al. |
| 6,267,390 B1 | 7/2001 | Maravetz et al. |
| 6,286,233 B1 | 9/2001 | Gaither |
| 6,289,558 B1 | 9/2001 | Hammerslag |
| D456,130 S | 4/2002 | Towns |
| 6,370,743 B2 | 4/2002 | Choe |
| 6,401,364 B1 | 6/2002 | Burt |
| 6,416,074 B1 | 7/2002 | Maravetz et al. |
| 6,467,195 B2 | 10/2002 | Pierre et al. |
| 6,477,793 B1 | 11/2002 | Pruitt et al. |
| 6,502,286 B1 | 1/2003 | Dubberke |
| 6,543,159 B1 | 4/2003 | Carpenter et al. |
| 6,568,103 B2 | 5/2003 | Durocher |
| 6,606,804 B2 | 8/2003 | Kaneko et al. |
| 746,563 A1 | 12/2003 | McMahon |
| 6,694,643 B1 | 2/2004 | Hsu |
| 6,708,376 B1 | 3/2004 | Landry |
| 6,711,787 B2 | 3/2004 | Jungkind et al. |
| 6,735,829 B2 | 5/2004 | Hsu |
| 6,757,991 B2 | 7/2004 | Sussmann |
| 6,775,928 B2 | 8/2004 | Grande et al. |
| 6,792,702 B2 | 9/2004 | Borsoi et al. |
| 6,802,439 B2 | 10/2004 | Azam et al. |
| 6,823,610 B1 | 11/2004 | Ashley |
| 6,871,812 B1 | 3/2005 | Chang |
| 6,877,256 B2 | 4/2005 | Martin et al. |
| 6,899,720 B1 | 5/2005 | McMillan |
| 6,922,917 B2 | 8/2005 | Kerns et al. |
| 6,938,913 B2 | 9/2005 | Elkington |
| 6,945,543 B2 | 9/2005 | De Bertoli et al. |
| D510,183 S | 10/2005 | Tresser |
| 6,976,972 B2 | 12/2005 | Bradshaw |
| 6,993,859 B2 | 2/2006 | Martin et al. |
| D521,226 S | 5/2006 | Douglas et al. |
| 819,993 A1 | 5/2006 | Haws et al. |
| 7,073,279 B2 | 7/2006 | Min |
| 7,076,843 B2 | 7/2006 | Sakabayashi |
| 7,082,701 B2 | 8/2006 | Dalgaard et al. |
| 7,096,559 B2 | 8/2006 | Johnson et al. |
| 7,134,224 B2 | 11/2006 | Elkington et al. |
| 7,266,911 B2 | 9/2007 | Holzer et al. |
| 7,281,341 B2 | 10/2007 | Reagan et al. |
| 7,293,373 B2 | 11/2007 | Reagan et al. |
| 7,331,126 B2 | 2/2008 | Johnson |
| 7,343,701 B2 | 3/2008 | Pare et al. |
| 7,367,522 B2 * | 5/2008 | Chen ........................ A43C 7/00 24/68 SK |
| 7,386,947 B2 | 6/2008 | Martin et al. |
| 7,392,602 B2 | 7/2008 | Reagan et al. |
| 7,401,423 B2 | 7/2008 | Reagan et al. |
| 7,490,458 B2 * | 2/2009 | Ford ..................... A01K 13/007 54/82 |
| 7,568,298 B2 | 8/2009 | Kerns |
| 7,582,102 B2 | 9/2009 | Heinz et al. |

(56) References Cited

U.S. PATENT DOCUMENTS

| | | | |
|---|---|---|---|
| 7,584,528 B2* | 9/2009 | Hu | A43C 11/16 24/68 SK |
| 7,591,050 B2 | 9/2009 | Hammerslag | |
| 7,597,675 B2 | 10/2009 | Ingimundarson et al. | |
| 7,600,660 B2 | 10/2009 | Kasper et al. | |
| 7,617,573 B2 | 11/2009 | Chen | |
| 7,624,517 B2 | 12/2009 | Smith | |
| 7,648,404 B1* | 1/2010 | Martin | B63B 35/7936 114/39.19 |
| 7,650,705 B2 | 1/2010 | Donnadieu et al. | |
| 7,694,354 B2 | 4/2010 | Philpott et al. | |
| 7,752,774 B2 | 7/2010 | Ussher | |
| 7,757,412 B2 | 7/2010 | Farys | |
| 7,762,531 B2* | 7/2010 | Bond | B66D 1/04 24/69 ST |
| 7,774,956 B2 | 8/2010 | Dua et al. | |
| D626,322 S | 11/2010 | Servettaz | |
| 7,841,106 B2 | 11/2010 | Farys | |
| 7,871,334 B2 | 1/2011 | Young et al. | |
| 7,877,845 B2 | 2/2011 | Signori | |
| 7,900,378 B1 | 3/2011 | Busse | |
| 7,908,769 B2 | 3/2011 | Pellegrini | |
| 7,947,061 B1 | 5/2011 | Reis | |
| 7,950,112 B2 | 5/2011 | Hammerslag et al. | |
| 7,954,204 B2* | 6/2011 | Hammerslag | A43L 35/16 24/68 SK |
| 7,963,049 B2 | 6/2011 | Messmer | |
| 7,992,261 B2 | 8/2011 | Hammerslag et al. | |
| D646,790 S | 10/2011 | Castillo et al. | |
| 8,056,150 B2 | 11/2011 | Stokes et al. | |
| 8,056,265 B2 | 11/2011 | Pirkle | |
| 8,074,379 B2 | 12/2011 | Robinson, Jr. et al. | |
| 8,091,182 B2 | 1/2012 | Hammerslag et al. | |
| 8,109,015 B2 | 2/2012 | Signori | |
| D663,850 S | 7/2012 | Joseph | |
| D663,851 S | 7/2012 | Joseph | |
| 8,215,033 B2 | 7/2012 | Carboy et al. | |
| 8,231,074 B2* | 7/2012 | Hu | A43C 11/165 24/68 SK |
| D665,088 S | 8/2012 | Joseph | |
| 8,235,321 B2 | 8/2012 | Chen | |
| 8,245,371 B2 | 8/2012 | Chen | |
| 8,257,293 B2 | 9/2012 | Ingimundarson et al. | |
| 8,266,827 B2 | 9/2012 | Dojan et al. | |
| 8,277,401 B2 | 10/2012 | Hammerslag et al. | |
| 8,302,329 B2 | 11/2012 | Hurd et al. | |
| 8,303,527 B2 | 11/2012 | Joseph | |
| 8,308,098 B2 | 11/2012 | Chen | |
| 8,353,087 B2 | 1/2013 | Chen | |
| 8,353,088 B2 | 1/2013 | Ha | |
| 8,381,362 B2 | 2/2013 | Hammerslag | |
| D677,045 S | 3/2013 | Voskuil | |
| D679,019 S | 3/2013 | Siddle et al. | |
| 8,434,200 B2 | 5/2013 | Chen | |
| 8,468,657 B2* | 6/2013 | Soderberg | A43C 11/16 24/68 SK |
| 8,490,299 B2 | 7/2013 | Dua et al. | |
| 8,516,662 B2* | 8/2013 | Goodman | A43C 11/165 24/68 SK |
| 8,578,632 B2 | 11/2013 | Bell et al. | |
| 8,652,164 B1 | 2/2014 | Aston | |
| 8,713,820 B2 | 5/2014 | Kerns et al. | |
| 8,955,199 B2* | 2/2015 | Chang | A43C 11/165 24/68 SK |
| 8,984,719 B2 | 3/2015 | Soderberg et al. | |
| 9,072,341 B2 | 7/2015 | Jungkind | |
| D735,987 S | 8/2015 | Hsu | |
| 9,101,181 B2 | 8/2015 | Soderberg et al. | |
| 9,125,455 B2 | 9/2015 | Kerns et al. | |
| 9,138,030 B2 | 9/2015 | Soderberg et al. | |
| 9,375,053 B2* | 6/2016 | Burns | A43C 11/165 |
| 9,486,039 B2* | 11/2016 | Ha | A43C 11/165 |
| 9,511,975 B2* | 12/2016 | Grenet | B65H 75/4431 |
| 9,629,417 B2* | 4/2017 | Cavanagh | A43C 11/20 |
| 9,706,814 B2* | 7/2017 | Converse | A43C 11/165 |
| 2002/0002781 A1 | 1/2002 | Bouvier | |
| 2002/0050076 A1 | 5/2002 | Borsoi et al. | |
| 2002/0062579 A1 | 5/2002 | Caeran | |
| 2002/0095750 A1 | 7/2002 | Hammerslag | |
| 2002/0129518 A1 | 9/2002 | Borsoi et al. | |
| 2002/0148142 A1 | 10/2002 | Oorei et al. | |
| 2002/0178548 A1 | 12/2002 | Freed | |
| 2003/0079376 A1 | 5/2003 | Mathieu | |
| 2003/0144620 A1 | 7/2003 | Sieller | |
| 2003/0150135 A1 | 8/2003 | Liu | |
| 2003/0177662 A1 | 9/2003 | Elkington et al. | |
| 2003/0204938 A1 | 11/2003 | Hammerslag | |
| 2004/0041452 A1 | 3/2004 | Williams | |
| 2004/0211039 A1 | 10/2004 | Livingston | |
| 2005/0054962 A1 | 3/2005 | Bradshaw | |
| 2005/0060912 A1 | 3/2005 | Holzer et al. | |
| 2005/0081339 A1* | 4/2005 | Sakabayashi | A43C 7/00 24/128 |
| 2005/0081403 A1 | 4/2005 | Mathieu | |
| 2005/0087115 A1 | 4/2005 | Martin | |
| 2005/0098673 A1* | 5/2005 | Huang | A43C 7/00 242/395 |
| 2005/0102861 A1 | 5/2005 | Martin | |
| 2005/0126043 A1 | 6/2005 | Reagan et al. | |
| 2005/0172463 A1 | 8/2005 | Rolla | |
| 2005/0184186 A1 | 8/2005 | Tsoi et al. | |
| 2005/0198866 A1 | 9/2005 | Wiper et al. | |
| 2005/0247813 A1* | 11/2005 | Kovacevich | A42B 3/08 242/388.6 |
| 2006/0135901 A1 | 6/2006 | Ingimundarson et al. | |
| 2006/0156517 A1 | 7/2006 | Hammerslag et al. | |
| 2006/0179685 A1 | 8/2006 | Borel et al. | |
| 2006/0185193 A1 | 8/2006 | Pellegrini | |
| 2006/0213085 A1 | 9/2006 | Azam | |
| 2006/0287627 A1 | 12/2006 | Johnson | |
| 2007/0006489 A1 | 1/2007 | Case, Jr. et al. | |
| 2007/0063459 A1 | 3/2007 | Kavarksy | |
| 2007/0068040 A1 | 3/2007 | Farys | |
| 2007/0084956 A1* | 4/2007 | Chen | A43C 7/00 242/388.6 |
| 2007/0113524 A1 | 5/2007 | Lander | |
| 2007/0128959 A1 | 6/2007 | Cooke | |
| 2007/0169378 A1 | 7/2007 | Sodeberg et al. | |
| 2008/0016717 A1 | 1/2008 | Ruban | |
| 2008/0060167 A1* | 3/2008 | Hammerslag | A43B 5/16 24/68 SK |
| 2008/0060168 A1 | 3/2008 | Hammerslag et al. | |
| 2008/0066272 A1 | 3/2008 | Hammerslag et al. | |
| 2008/0066345 A1 | 3/2008 | Hammerslag et al. | |
| 2008/0066346 A1 | 3/2008 | Hammerslag et al. | |
| 2008/0068204 A1 | 3/2008 | Carmen et al. | |
| 2008/0083135 A1 | 4/2008 | Hammerslag et al. | |
| 2008/0092279 A1 | 4/2008 | Chiang | |
| 2008/0172848 A1 | 7/2008 | Chen | |
| 2008/0196224 A1* | 8/2008 | Hu | A43C 11/16 24/68 SK |
| 2009/0019734 A1 | 1/2009 | Reagan et al. | |
| 2009/0071041 A1 | 3/2009 | Hooper | |
| 2009/0090029 A1 | 4/2009 | Kishino | |
| 2009/0172928 A1 | 7/2009 | Messmer et al. | |
| 2009/0184189 A1 | 7/2009 | Soderberg et al. | |
| 2009/0272007 A1 | 11/2009 | Beers et al. | |
| 2009/0277043 A1 | 11/2009 | Graser et al. | |
| 2010/0064547 A1 | 3/2010 | Kaplan | |
| 2010/0101061 A1 | 4/2010 | Ha | |
| 2010/0115744 A1 | 5/2010 | Fong | |
| 2010/0139057 A1* | 6/2010 | Soderberg | A43C 11/16 24/68 R |
| 2010/0154254 A1 | 6/2010 | Fletcher | |
| 2010/0175163 A1 | 7/2010 | Litke | |
| 2010/0251524 A1 | 10/2010 | Chen | |
| 2010/0269373 A1 | 10/2010 | Pirkle | |
| 2010/0299959 A1 | 12/2010 | Hammerslag | |
| 2010/0319216 A1 | 12/2010 | Grenzke et al. | |
| 2011/0000173 A1 | 1/2011 | Lander | |
| 2011/0071647 A1 | 3/2011 | Mahon | |
| 2011/0162236 A1 | 7/2011 | Voskuil et al. | |
| 2011/0167543 A1 | 7/2011 | Kovacevich et al. | |

(56) References Cited

U.S. PATENT DOCUMENTS

| | | |
|---|---|---|
| 2011/0191992 A1 | 8/2011 | Chen |
| 2011/0197362 A1 | 8/2011 | Chella et al. |
| 2011/0225843 A1* | 9/2011 | Kerns ................. A43B 3/0052 36/50.1 |
| 2011/0258876 A1 | 10/2011 | Baker et al. |
| 2011/0266384 A1* | 11/2011 | Goodman ........... A43C 11/165 242/396.4 |
| 2012/0000091 A1 | 1/2012 | Cotterman et al. |
| 2012/0004587 A1* | 1/2012 | Nickel ................. A61F 5/0118 602/21 |
| 2012/0005995 A1 | 1/2012 | Emery |
| 2012/0023717 A1 | 2/2012 | Chen |
| 2012/0101417 A1 | 4/2012 | Joseph |
| 2012/0102783 A1 | 5/2012 | Swigart et al. |
| 2012/0138882 A1 | 6/2012 | Moore et al. |
| 2012/0157902 A1 | 6/2012 | Castillo et al. |
| 2012/0167290 A1 | 7/2012 | Kovacevich et al. |
| 2012/0174437 A1 | 7/2012 | Heard |
| 2012/0204381 A1* | 8/2012 | Ingimundarson ........ A41F 1/04 24/71.1 |
| 2012/0228419 A1* | 9/2012 | Chen ................... A43C 11/165 242/395 |
| 2012/0246974 A1 | 10/2012 | Hammerslag et al. |
| 2012/0310273 A1 | 12/2012 | Thorpe |
| 2013/0012856 A1 | 1/2013 | Hammerslag et al. |
| 2013/0014359 A1* | 1/2013 | Chen ................... A43C 11/165 24/68 SK |
| 2013/0019501 A1 | 1/2013 | Gerber |
| 2013/0025100 A1* | 1/2013 | Ha ...................... A43C 11/165 24/712.9 |
| 2013/0091667 A1 | 4/2013 | Chen |
| 2013/0092780 A1 | 4/2013 | Soderberg et al. |
| 2013/0269219 A1 | 10/2013 | Burns et al. |
| 2013/0277485 A1 | 10/2013 | Soderberg et al. |
| 2013/0340283 A1 | 12/2013 | Bell et al. |
| 2013/0345612 A1 | 12/2013 | Bannister et al. |
| 2014/0082963 A1 | 3/2014 | Beers |
| 2014/0094728 A1* | 4/2014 | Soderberg ............... A61F 5/028 602/6 |
| 2014/0117140 A1 | 5/2014 | Goodman et al. |
| 2014/0123440 A1 | 5/2014 | Capra et al. |
| 2014/0123449 A1* | 5/2014 | Soderberg .............. A43C 1/003 24/712.1 |
| 2014/0208550 A1* | 7/2014 | Neiley ................. A43C 7/00 24/712.1 |
| 2014/0221889 A1* | 8/2014 | Burns ................... A61F 5/0102 602/5 |
| 2014/0290016 A1* | 10/2014 | Lovett ................. A43C 11/20 24/713.5 |
| 2014/0359981 A1* | 12/2014 | Cotterman ............. A43C 11/20 24/712.9 |
| 2015/0005685 A1 | 1/2015 | Chetlapalli et al. |
| 2015/0007422 A1* | 1/2015 | Cavanagh ............. A43C 11/165 24/68 SK |
| 2015/0014463 A1* | 1/2015 | Converse .............. A61F 5/0118 242/396.1 |
| 2015/0026936 A1 | 1/2015 | Kerns et al. |
| 2015/0033519 A1 | 2/2015 | Hammerslag et al. |
| 2015/0059206 A1* | 3/2015 | Lovett ................. A43C 11/165 36/50.1 |
| 2015/0076272 A1* | 3/2015 | Trudel .................. A43C 7/00 242/381.4 |
| 2015/0089779 A1* | 4/2015 | Lawrence ............... B60R 9/10 24/68 BT |
| 2015/0089835 A1 | 4/2015 | Hammerslag et al. |
| 2015/0101160 A1 | 4/2015 | Soderberg et al. |
| 2015/0150705 A1* | 6/2015 | Capra ................... A61F 5/01 602/6 |
| 2015/0151070 A1 | 6/2015 | Capra et al. |
| 2015/0190262 A1 | 7/2015 | Capra et al. |
| 2015/0223608 A1 | 8/2015 | Capra et al. |
| 2015/0237962 A1 | 8/2015 | Soderberg et al. |
| 2015/0313319 A1* | 11/2015 | Ha ....................... A43C 11/165 24/303 |
| 2015/0335458 A1 | 11/2015 | Romo |
| 2016/0058130 A1 | 3/2016 | Boney |
| 2016/0120267 A1* | 5/2016 | Burns .................. A44B 11/065 24/68 C |
| 2017/0303643 A1* | 10/2017 | Converse ............. A43C 11/165 |
| 2017/0304102 A1* | 10/2017 | Turrini ..................... A61F 5/01 |
| 2017/0311682 A1* | 11/2017 | Trudel ................. A43C 11/165 |
| 2017/0354207 A1* | 12/2017 | Signori ................... A43B 5/14 |

FOREIGN PATENT DOCUMENTS

| | | |
|---|---|---|
| CH | 199766 | 9/1938 |
| CH | 204 834 A | 5/1939 |
| CN | 2613167 | 4/2004 |
| CN | 201015448 | 2/2008 |
| DE | 641976 | 2/1937 |
| DE | 23 41 658 | 3/1974 |
| DE | 29 00 077 A1 | 7/1980 |
| DE | 31 01 952 A1 | 9/1982 |
| DE | 38 13 470 | 11/1989 |
| DE | 3838474 | 5/1990 |
| DE | 43 02 401 A1 | 8/1994 |
| DE | 43 05 671 A1 | 9/1994 |
| DE | 9308037 | 10/1994 |
| DE | 43 26 049 A1 | 2/1995 |
| DE | 9315776 | 2/1995 |
| DE | 29503552.8 | 4/1995 |
| DE | 196 24 553 | 1/1998 |
| DE | 19945045 A1 | 3/2001 |
| DE | 10335940 | 3/2005 |
| DE | 20 2010 00354 U1 | 6/2010 |
| DE | 11 2013 005273 T5 | 9/2015 |
| DE | 11 2014 003135 T5 | 4/2016 |
| EP | 0 056 953 | 8/1982 |
| EP | 0 099 504 | 2/1984 |
| EP | 0 123 050 | 10/1984 |
| EP | 0 155 596 | 9/1985 |
| EP | 0 201 051 | 11/1986 |
| EP | 0 255 869 | 2/1988 |
| EP | 0 393 380 | 10/1990 |
| EP | 0 589 232 A1 | 3/1994 |
| EP | 0 589 233 A1 | 3/1994 |
| EP | 0 614 625 A1 | 9/1994 |
| EP | 0 651 954 A1 | 5/1995 |
| EP | 0 679 346 | 11/1995 |
| EP | 0 693 260 B1 | 1/1996 |
| EP | 0 734 662 A1 | 10/1996 |
| EP | 0 848 917 | 6/1998 |
| EP | 0 923 965 | 6/1999 |
| EP | 0 937 467 | 8/1999 |
| EP | 1163860 | 12/2001 |
| EP | 1 219 195 | 7/2002 |
| EP | 1 236 412 | 9/2002 |
| EP | 2298107 B1 | 3/2011 |
| EP | 2359708 | 8/2011 |
| FR | 1 404 799 | 7/1965 |
| FR | 2 019 991 A | 7/1970 |
| FR | 2 598 292 A1 | 11/1987 |
| FR | 2 726 440 A1 | 5/1996 |
| FR | 2 770 379 A1 | 5/1999 |
| FR | 2 814 919 A1 | 4/2002 |
| GB | 189911673 | 7/1899 |
| GB | 216400 | 5/1924 |
| GB | 2 449 722 A | 12/2008 |
| IT | 1220811 | 6/1990 |
| IT | 2003 A 000197 | 3/2005 |
| IT | 2003 A 000198 | 3/2005 |
| JP | 51-121375 | 10/1976 |
| JP | 53-124987 | 3/1977 |
| JP | 54-108125 | 2/1978 |
| JP | H02-236025 | 9/1990 |
| JP | 6-284906 | 2/1996 |
| JP | 3030988 | 11/1996 |
| JP | 3031760 | 12/1996 |
| JP | 10-199366 | 7/1998 |
| JP | 2004-016732 | 1/2004 |
| JP | 2004-041666 | 2/2004 |

(56) References Cited

FOREIGN PATENT DOCUMENTS

| | | |
|---|---|---|
| JP | 2009-504210 | 2/2009 |
| KR | 20-0367882 | 11/2004 |
| KR | 20-0400568 | 8/2005 |
| KR | 10-0598627 | 7/2006 |
| KR | 10-0953398 | 4/2010 |
| KR | 10-1025134 B1 | 3/2011 |
| KR | 10-1028468 | 4/2011 |
| KR | 10-1053551 | 7/2011 |
| WO | WO 94/27456 | 12/1994 |
| WO | WO 1995/03720 | 2/1995 |
| WO | WO 95/11602 | 5/1995 |
| WO | WO 98/33408 | 8/1998 |
| WO | WO 98/37782 | 9/1998 |
| WO | WO 99/09850 | 3/1999 |
| WO | WO 99/15043 | 4/1999 |
| WO | WO 99/43231 | 9/1999 |
| WO | WO 00/53045 | 9/2000 |
| WO | WO 2000/76337 A1 | 12/2000 |
| WO | WO 01/08525 | 2/2001 |
| WO | WO 01/15559 | 3/2001 |
| WO | WO 02/051511 | 7/2002 |
| WO | WO 2004/093569 | 11/2004 |
| WO | WO 2005/013748 A1 | 2/2005 |
| WO | WO/2007/016983 | 2/2007 |
| WO | WO 2008/015214 | 2/2008 |
| WO | WO/2008/033963 | 3/2008 |
| WO | WO/2009/134858 | 11/2009 |
| WO | WO 2010/059989 A2 | 5/2010 |
| WO | WO 2012/165803 A2 | 12/2012 |
| WO | WO 2015/179332 A1 | 11/2015 |
| WO | WO 2015/181928 A1 | 12/2015 |

OTHER PUBLICATIONS

ASOLO® Boot Brochure Catalog upon information and belief date is as early as Aug. 22, 1997, 12 pages.
La Sportiva, A Technical Lightweight Double Boot for Cold Environments, 1 page. Accessed on May 27, 2015. Retrieved from http://www.sportiva.com/products/footwear/mountain/spantik.
"Strength of materials used to make my Safety Harnesses," Elaine, Inc. Jul. 9, 2012. Retrieved from <https://web.archive.org/web/20120709002720/http://www.childharness.ca/strength_data.html> on Mar. 17, 2014, 2 pages.
International Search Report and Written Opinion for PCT/US2013/032326 dated Jun. 14, 2013, 27 pages.
International Preliminary Report on Patentability for PCT/US2013/032326 dated Sep. 16, 2014, 6 pages.
International Search Report and Written Opinion for PCT/US2013/057637 dated Apr. 7, 2014, 34 pages.
International Preliminary Report on Patentability for PCT/US2013/057637 dated Mar. 3, 2015, 9 pages.
International Search Report and Written Opinion for PCT/US2013/068342 dated Apr. 7, 2014, 29 pages.
International Preliminary Report on Patentability for PCT/US2013/068342 dated May 5, 2015, 9 pages.
International Search Report and Written Opinion for PCT/US2014/014952 dated Apr. 25, 2014, 17 pages.
International Preliminary Report on Patentability for PCT/US2014/014952 dated Aug. 11, 2015, 9 pages.
International Search Report and Written Opinion for PCT/US2014/066212 dated Apr. 22, 2015, 16 pages.
International Search Report and Written Opinion for PCT/US2014/032574 dated Oct. 31, 2014, 19 pages.
International Search Report and Written Opinion for PCT/US2014/045291 dated Nov. 6, 2014, 12 pages.
International Preliminary Report on Patentability for PCT/US2014/045291 dated Jan. 5, 2016, 5 pages.

International Search Report and Written Opinion for PCT/US2014/013458 dated May 19, 2014, 12 pages.
International Preliminary Report on Patentability for PCT/US2014/013458 dated Jul. 28, 2015, 7 pages.
International Search Report and Written Opinion for PCT/US2013/068814 dated Jun. 9, 2014, 18 pages.
International Preliminary Report on Patentability for PCT/US2013/068814 dated May 12, 2015, 12 pages.
Notice of Reasons for Rejection from the Japanese Patent Office dated Feb. 26, 2015 for design application No. 2014-015570, 4 pages.
Receipt of Certificate of Design Registration No. 1529678 from the Japanese Patent Office for design application No. 2014-015570 dated Jun. 26, 2015, 1 page.
International Search Report and Written Opinion for PCT/US2014/055710 dated Jul. 6, 2015, 19 pages.
International Search Report and Written Opinion for PCT/US2014/054420 dated Jul. 6, 2015, 21 pages.
The Preliminary Rejections from the Korean Intellectual Property Office for Application No. 30-201434959 dated Aug. 7, 2015, is not translated into English. The document requests a renaming of the application to be in accordance with Korean patent law, 5 pages total.
The Preliminary Rejections from the Korean Intellectual Property Office for Application No. 30-201434959 dated Apr. 7, 2015, is not translated into English. The document requests a revision of the drawings to be in accordance with Korean patent law, 6 pages total.
Certificate of Design Registration No. 30-809409 dated Aug. 3, 2015 from the Korean Intellectual Property Office for Appln No. 30/2015-11475, 2 pages.
Certificate of Design Registration No. 30-809410 dated Aug. 3, 2015 from the Korean Intellectual Property Office for Appln No. 30/2015-11476, 2 pages.
European Search Report for EP 14168875 dated Oct. 29, 2014, 9 pages.
International Search Report and Written Opinion for PCT/US2014/020894 dated Jun. 20, 2014, 12 pages.
International Preliminary Report on Patentability for PCT/US2014/020894 dated Sep. 8, 2015, 7 pages.
International Search Report and Written Opinion for PCT/US2014/041144 dated Dec. 10, 2014, 13 pages.
International Preliminary Report on Patentability for PCT/US2014/032574 dated Oct. 6, 2015, 12 pages.
International Search Report and Written Opinion for PCT/US2014/046238 dated Nov. 21, 2014, 17 pages.
Office Action dated Oct. 8, 2015 from the German Patent and Trademark Office for Appln No. 402015100191.2, regarding the title of the invention, 2 pages.
Anonymous, "Shore durometer," Wikipedia, the free encyclopedia, Mar. 10, 2012, XP002747470, Retrieved from the Internet: URL: https://en.wikipedia.org/w/index.php?title=Shore_durometer&oldid=481128180 [retrieved on Oct. 20, 2015], 6 pages.
Notice of Reasons for Rejection from the Japanese Patent Office dated Oct. 5, 2015 for design application No. 2015-004923, 4 pages.
"Save Tourniquet," 3 pages. Copyright 2015. Accessed on Dec. 11, 2015. Retrieved from http://www.savetourniquet.com/.
Supplementary European Search Report for EP 13761841 dated Oct. 21, 2015, all pages.
International Search Report and Written Opinion for PCT/US2015/054530 dated Jan. 13, 2016, all pages.
U.S. Appl. No. 14/322,690, filed Jul. 2, 2014 Non-Final Rejection dated Aug. 23, 2016, all pages.
U.S. Appl. No. 14/322,690, filed Jul. 2, 2014 Notice of Allowance dated Dec. 19, 2016, all pages.
Office Action with cited art for German Patent Application No. DE112014003135 dated Jan. 17, 2018, all pages.

\* cited by examiner

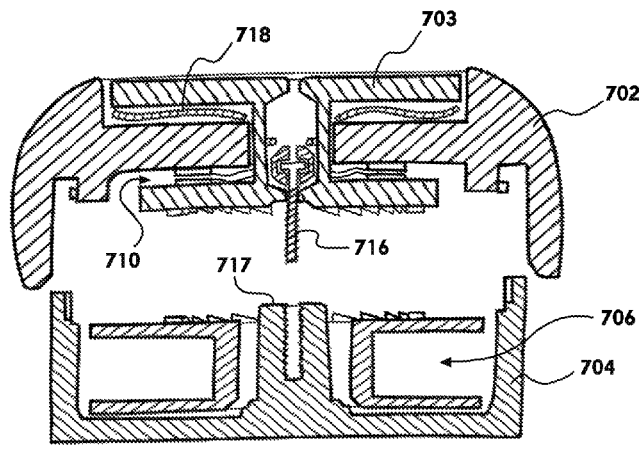
FIG. 7A
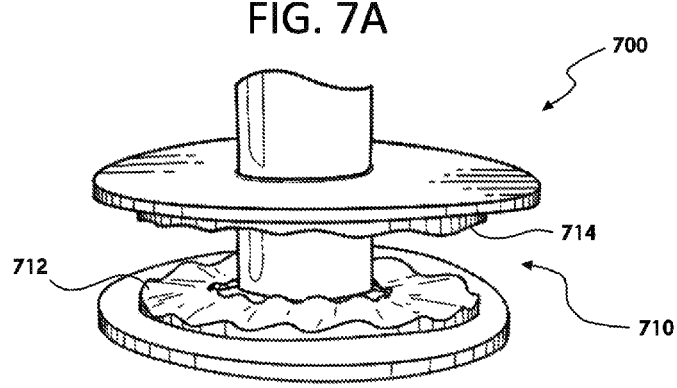
FIG. 7B
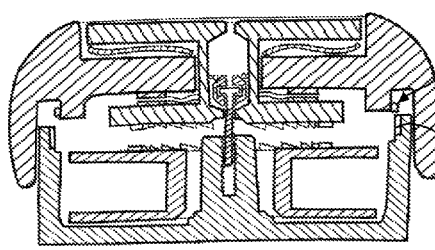 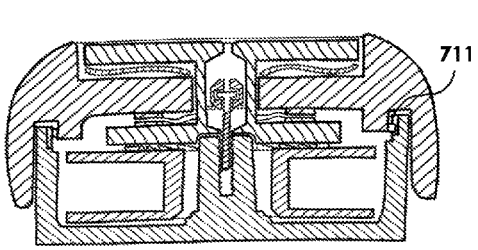
FIG. 7C  FIG. 7D

A-A

B-B

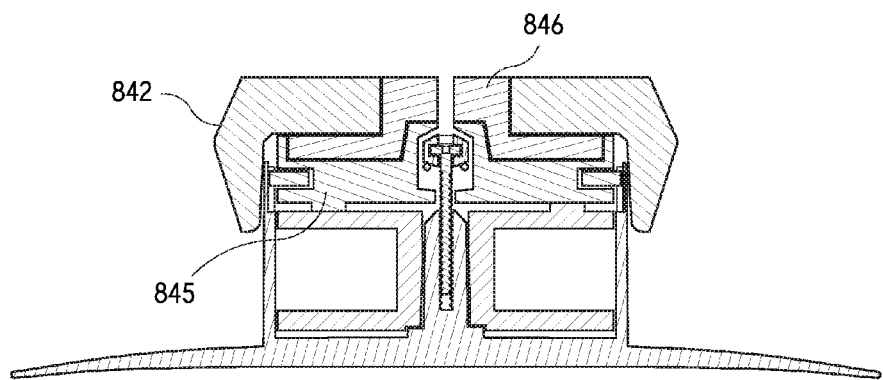
FIG. 8Q
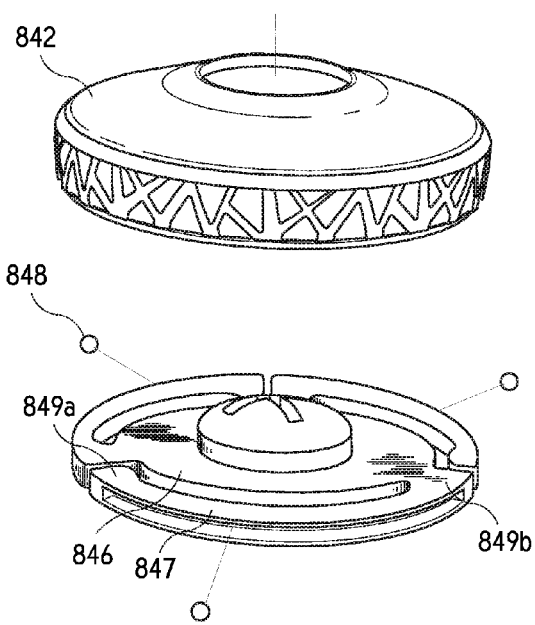
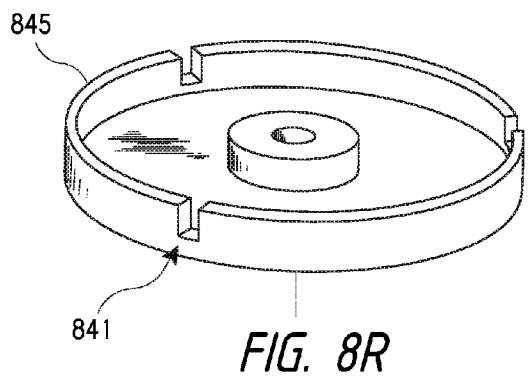
FIG. 8R

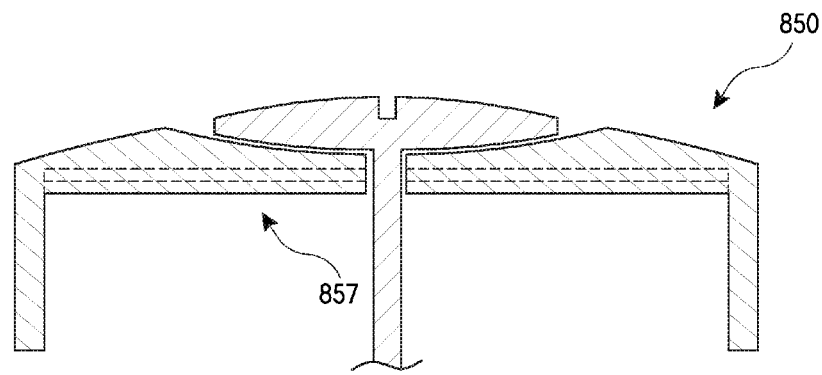
FIG. 8V
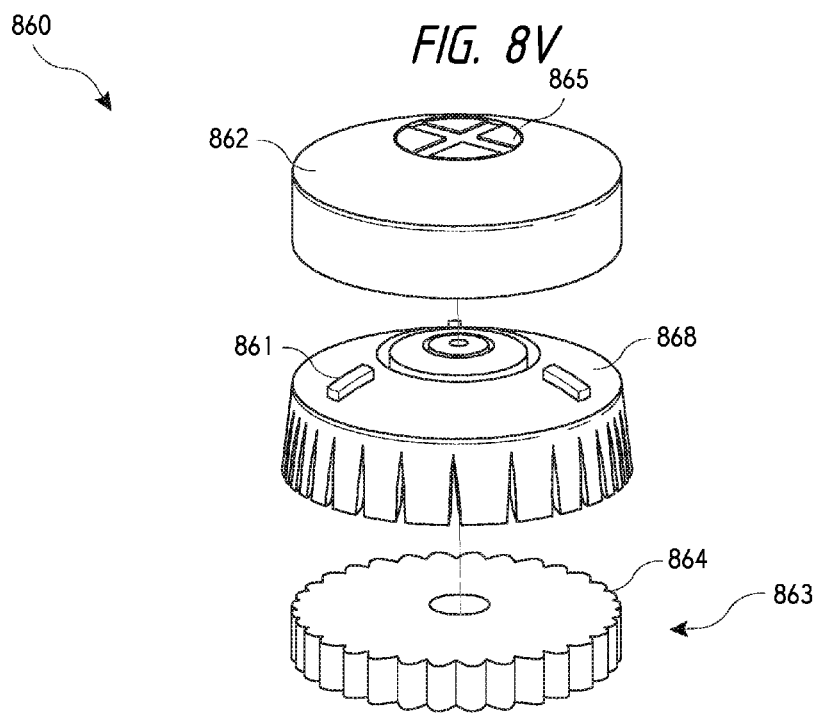
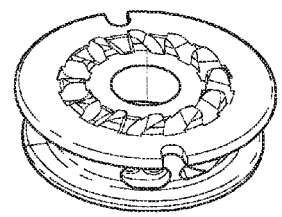
FIG. 8W

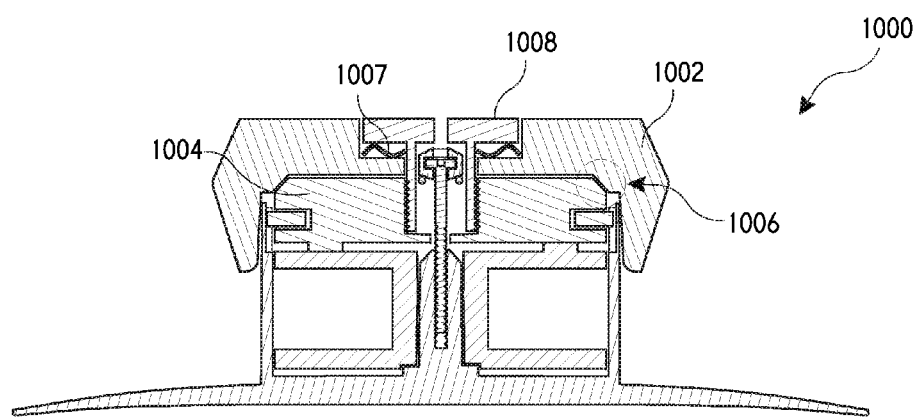
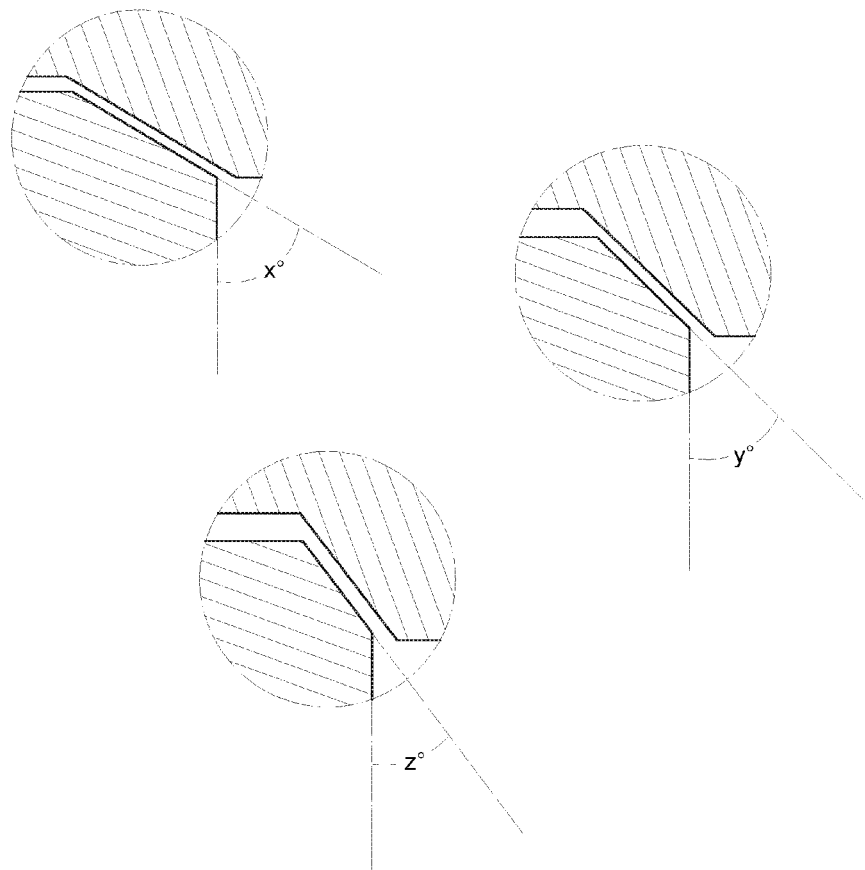
FIG. 10A

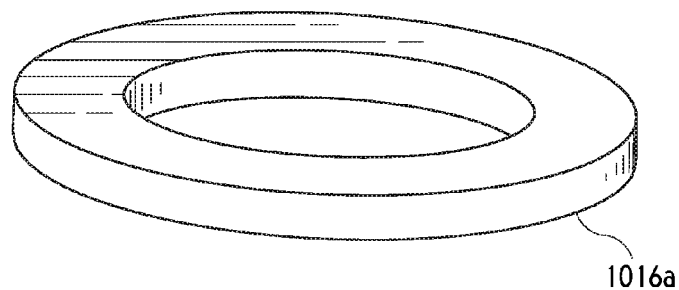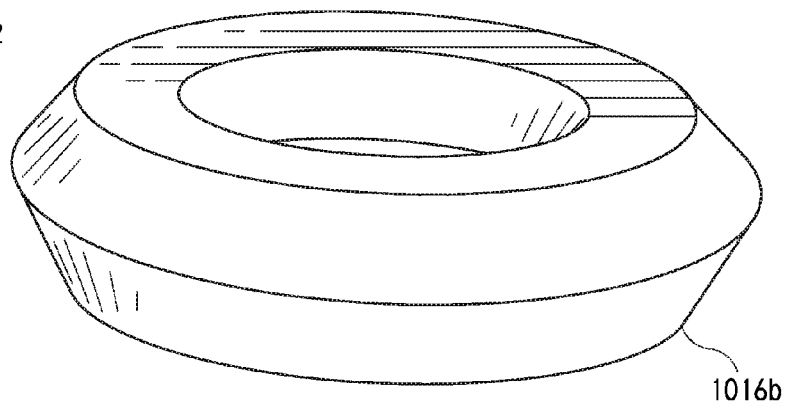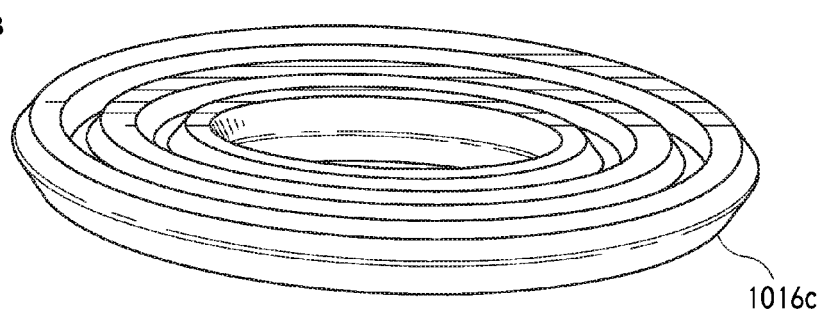
FIG. 10D

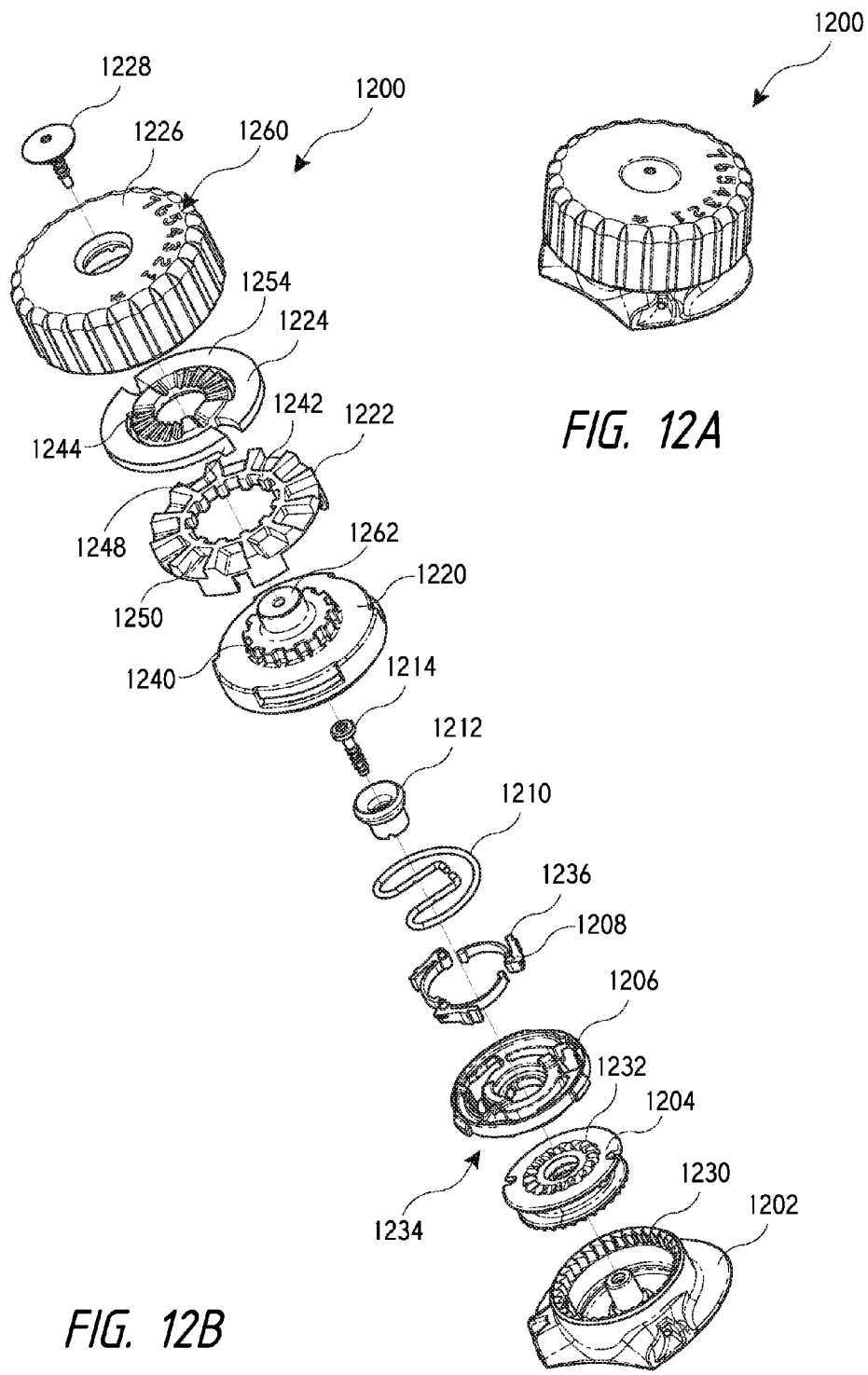

TENSION LIMITING MECHANISMS FOR CLOSURE DEVICES AND METHODS THEREFOR

CROSS-REFERENCES TO RELATED APPLICATIONS

This application is a continuation of U.S. Pat. No. 14/322,690 filed Jul. 2, 2014, entitled "Tension Limiting Mechanisms for Closure Devices and Methods Therefor," which claims priority to U.S. Patent Application No. 61/842,238 filed Jul. 2, 2013, entitled "Tension Limiting Mechanisms for Closure Devices and Methods Therefor," the entire disclosures of which are hereby incorporated by reference, for all purposes, as if fully set forth herein.

BACKGROUND OF THE INVENTION

The present invention is related to closure devices for various articles, such as braces, medical devices, shoes, clothing, apparel, and the like. Such articles typically include closure devices that allow the article to be placed and closed about a body part. The closure devices are typically used to maintain or secure the article to the body part. For example, shoes are typically placed over an individual's foot and lace is tensioned and tied to close the shoe about the foot and secure the shoe to the foot. Conventional closure devices have been modified in an effort to increase the fit and/or comfort of the article about the body part. For example, shoe lacing configurations and/or patterns have been modified in an attempt to increase the fit and/or comfort of wearing shoes. Conventional closure devices have also been modified in an effort to decrease the time in which an article may be closed and secured about the body part. These modifications have resulted in the use of various pull cords, straps, and tensioning devices that enable the article to be quickly closed and secured to the foot.

BRIEF SUMMARY OF THE INVENTION

The embodiments described herein provide closure systems having mechanisms that limit the tension that may be applied to a tension member (e.g., lace) in closing an article. The tension limiting mechanisms may prevent or limit the article from being over-tightened. Additionally or alternatively, in some embodiments the closure systems may include a mechanism that functions to substantially maintain a tension on the tension member. Stated differently, the closure system may include a mechanism that allows the tension member's tension to be released or loosened when a sudden spike in tension occurs, such as from swelling of a limb, dynamic movement of a body part, an impact of the article with surrounding objects, and the like. According to one aspect, a reel for use with a lacing system for tightening an article is described. The reel includes a housing having an interior region and a spool positioned within the interior region of the housing and rotatable relative thereto. The spool has having an annular channel formed therein. The reel also includes a knob that is rotatable relative to the housing and operably coupled with the spool to cause the spool to rotate within the interior region of the housing. A tension member is coupled with the spool and is tensioned by winding the tension member around the spool's annular channel upon rotation of the knob, The reel further includes a tension control mechanism that is configured to: enable tensioning of the tension member by rotation of the knob until a tension threshold is achieved, after which further rotation of the knob does not cause further tensioning of the tension member; and enable rotation of the spool within the housing's interior region upon tensioning of the tension member from a source other than the knob.

According to another aspect, a device for tightening an article is described. The device includes a housing having an interior region and a spool positioned within the interior region of the housing and rotatable relative thereto. The device also includes a tightening mechanism that is operably coupled with the spool to cause the spool to rotate within the interior region of the housing and a tension member that is coupled with the spool and configured to be tensioned upon rotation of the spool via the tightening mechanism. The device further includes a tension limiting mechanism that allows the tension member to be tensioned via the tightening mechanism until a tension threshold is achieved, after which further operation of the tightening mechanism does not substantially tension the tension member.

According to yet another aspect, a method for assembling a device for tightening an article is described. The method includes providing a housing having an interior region and positioning a spool within the interior region of the housing so that the spool is rotatable relative to the housing. The method also includes operably coupling a tightening mechanism with the spool so that the spool is rotatable within the interior region of the housing upon operation of the tightening mechanism. The method further includes coupling a tension member with the spool so that the tension member is tensionable upon rotation of the spool via the tightening mechanism. The method additionally includes operably coupling a tension limiting mechanism with the spool to enable the tension member to be tensioned via the tightening mechanism until a tension threshold is achieved, after which further operation of the tightening mechanism does not substantially tension the tension member.

According to yet another aspect, a device for tightening an article is described. The device includes a housing having an interior region and a spool positioned within the interior region of the housing and rotatable relative thereto. The device also includes a tightening mechanism that is operably coupled with the spool to cause the spool to rotate within the interior region of the housing and a tension member that is coupled with the spool and configured to be tensioned upon rotation of the spool via the tightening mechanism. The device further includes a force limiting mechanism that is configured to transfer tightening forces from the tightening mechanism to one or more internal components of the device until a tightening force threshold is achieved and that is further configured to not transfer tightening forces from the tightening mechanism to the one or more internal components of the device after the tightening force threshold is achieved.

BRIEF DESCRIPTION OF THE DRAWINGS

The present invention is described in conjunction with the appended figures:

FIGS. 7A-M illustrate embodiments of closure devices and/or tension limiting mechanisms that utilize a wave clutch or similar type clutch component.

FIGS. 9A-I illustrate embodiments of closure devices and/or tension limiting mechanisms that affect a user's grip on a knob portion of the closure device.

FIGS. 10A-G illustrate embodiments of closure devices and/or tension limiting mechanisms that utilize friction-based clutching system.

FIGS. 12A-E illustrate another embodiment of a closure system having a tension limiting component or mechanism.

Figure 1:
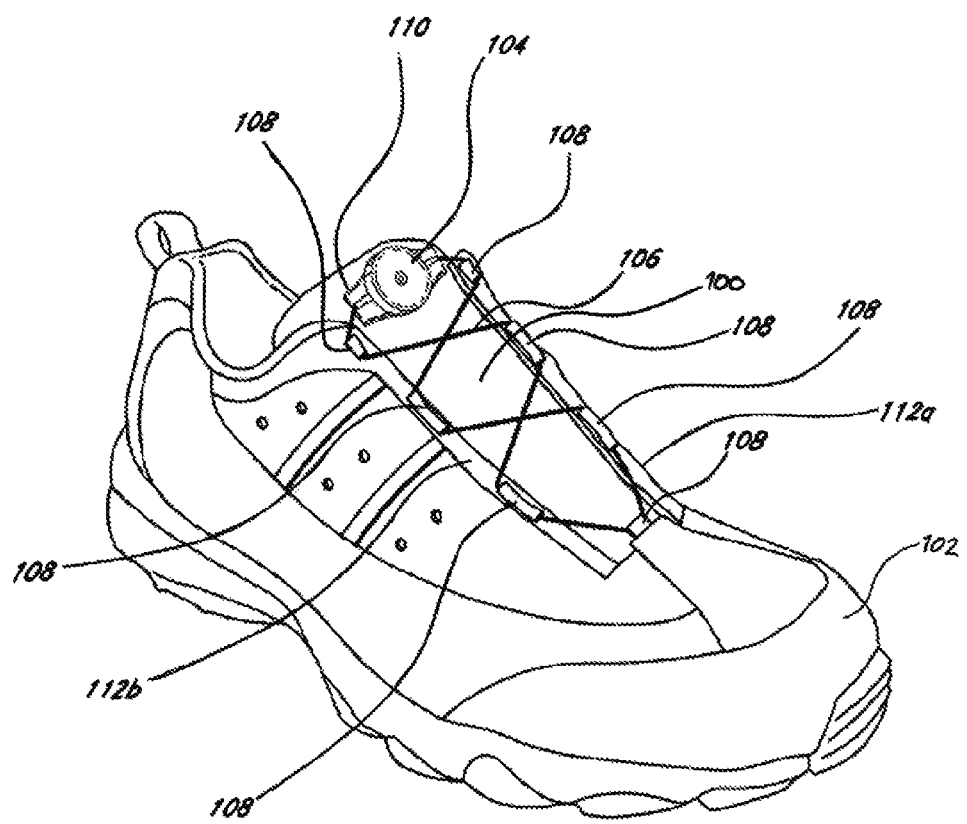
FIG. 1 illustrates a perspective view of a lacing system that may be used for tightening a shoe or other article.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

Embodiments described herein provide various tension limiting mechanisms that may be used for closure devices and/or other devices. A specific example of a closure device for which the input force limiting mechanisms may be used are rotary or reel based closure devices that typically include a knob that is grasped by a user and rotated to wind lace around a spool mounted within a housing. The lace is tensioned by the closure device as the lace is wound around the spool. Tensioning of the lace is used to close or tighten apparel, equipment, or some other component that the closure device is coupled with.

These types of closure device are used frequently to closure or tighten various apparel and equipment, such as standard footwear, athletic footwear, medical footwear, and the like. Some uses of these closure devices require the application of relatively large tension to the closure device's lace. To provide the relatively large tension forces, some closure devices include gearing that amplifies the input force applied by a user. The gearing, however, may allow a user to apply far greater tension than is required for a given application. For example, in snowboard boots, a geared system may be used to increase the lace tension that may be applied by the closure system. The increased lace tension may be required to completely close and properly tighten one or more layers of the snowboard boots. The geared system, however, may allow a user to tighten the lace beyond what would be expected in use and/or beyond a tension that may cause discomfort or pain if the boots are being worn. If the boots are not fit about a leg, a user may over-tighten the lace due to neglect, lack of attention, and the like.

Over-tensioning of the lace may damage or break the lace as well as damage or break internal components of the closure device and/or lace guides around which the lace is wound. Further, when the closure device is used to close apparel or equipment about a user's body part, over-tensioning the lace may result in the body part being squeezed too tightly, which may limit or restrict blood flow to and from the body part. Such over-tensioning, for example, can be a serious problem for diabetic patients wearing a brace (e.g., foot brace or boot) because these patients often lose sensation or feeling in the body part that is being supported by the brace. Loss of blood flow to a body part in diabetic patients can result in serious complications including amputation of the body part. The embodiments described herein provide mechanisms that limit the amount of tension that may be applied to the lace. This is often achieved by limiting the input force that is transferred from the closure device's knob to the spool or other component. As such, a user may not be able to over-tighten the closure device, thereby remedying many of the problems associated with over-tensioning a lace. Further, the embodiments described herein also allow a repeatable tension to be applied to the lace and thus to the footwear or other device. Repeatable tensioning as used herein means the ability to repeatedly tension the lace to a favorable or desired setting, such as to a desired lace tension and/or fit of the footwear about the body. The embodiments described herein allow a user to easily don footwear and operate a closure device (e.g., reel assembly) to tension the lace until a desired tension is achieved, after which the closure device will not further tension the lace. In this manner, donning and tensioning of the footwear is greatly enhanced.

Referring briefly now to FIG. 1, illustrated is a perspective view of an embodiment of closure device or system that is used for tightening a shoe. The shoe can be any suitable footwear that can be tightened around a wearer's foot. The closure device can be used to close or tighten various other articles as described herein, such as, for example, a belt, a hat, a glove, snowboard bindings, a medical brace, or a bag. The closure device can include a reel assembly 104, a lace 106, and one or more lace guides 108. In the illustrated embodiment, the reel assembly 104 can be attached to the tongue 110 of the shoe, although various other configurations are also possible. For example, the reel assembly 104 can be attached to a side of the shoe, which can be advantageous for shoes in which the shoe sides 112a-b are designed to be drawn closely together when tightened leaving only a small portion of the tongue 110 exposed. The reel assembly 104 can also be attached to the back of the shoe and a portion of the lace 106 can pass through the shoe using tubing for the lace to travel through. In some embodiments the tubing can be positioned on either side of the wearer's ankle such that the lace 106 can be engaged with the reel assembly 104 when back-mounted. In some embodiments, the reel assembly 104 may also be attached to the lateral side at or near the top of the lacing throat.

Figure 2:
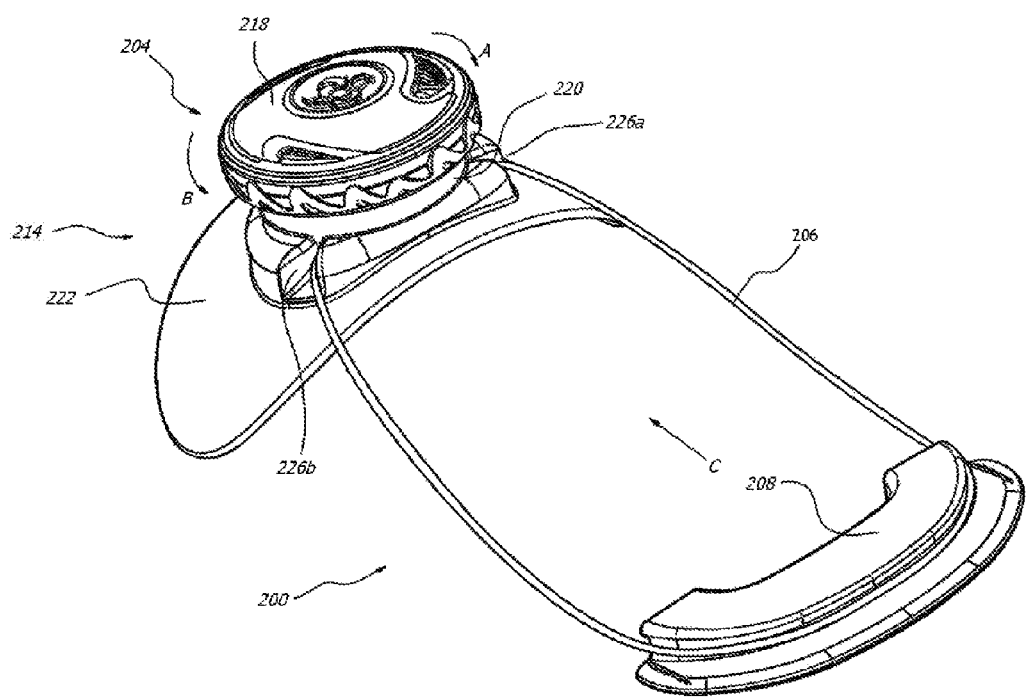
FIG. 2 illustrates a perspective view of another lacing system that can be used for tightening a shoe or other article.
Figure 3:
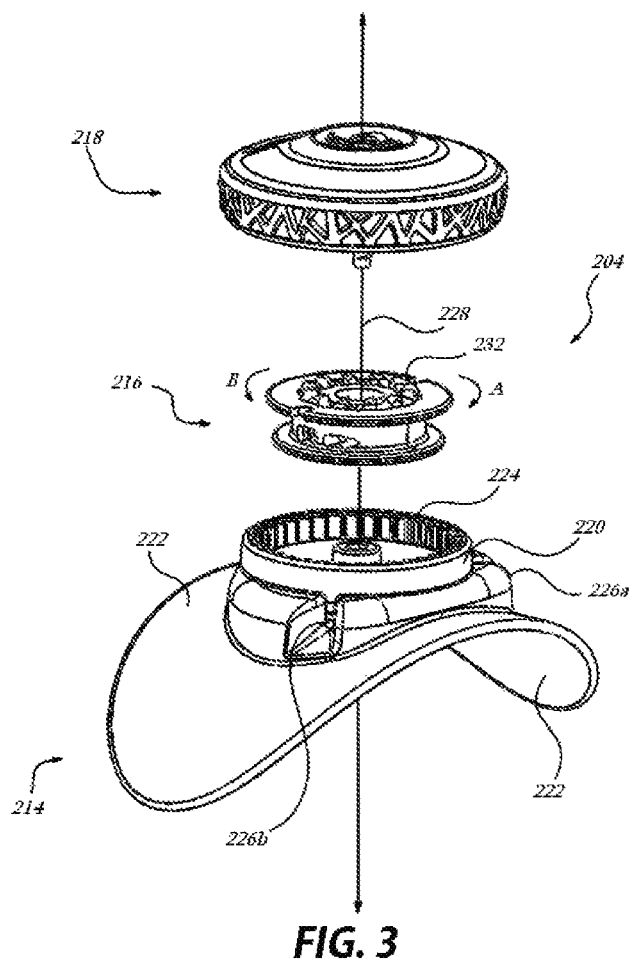
FIGS. 3 & 4 illustrate exploded perspective views of the lacing system of FIG. 2.
Figure 4:
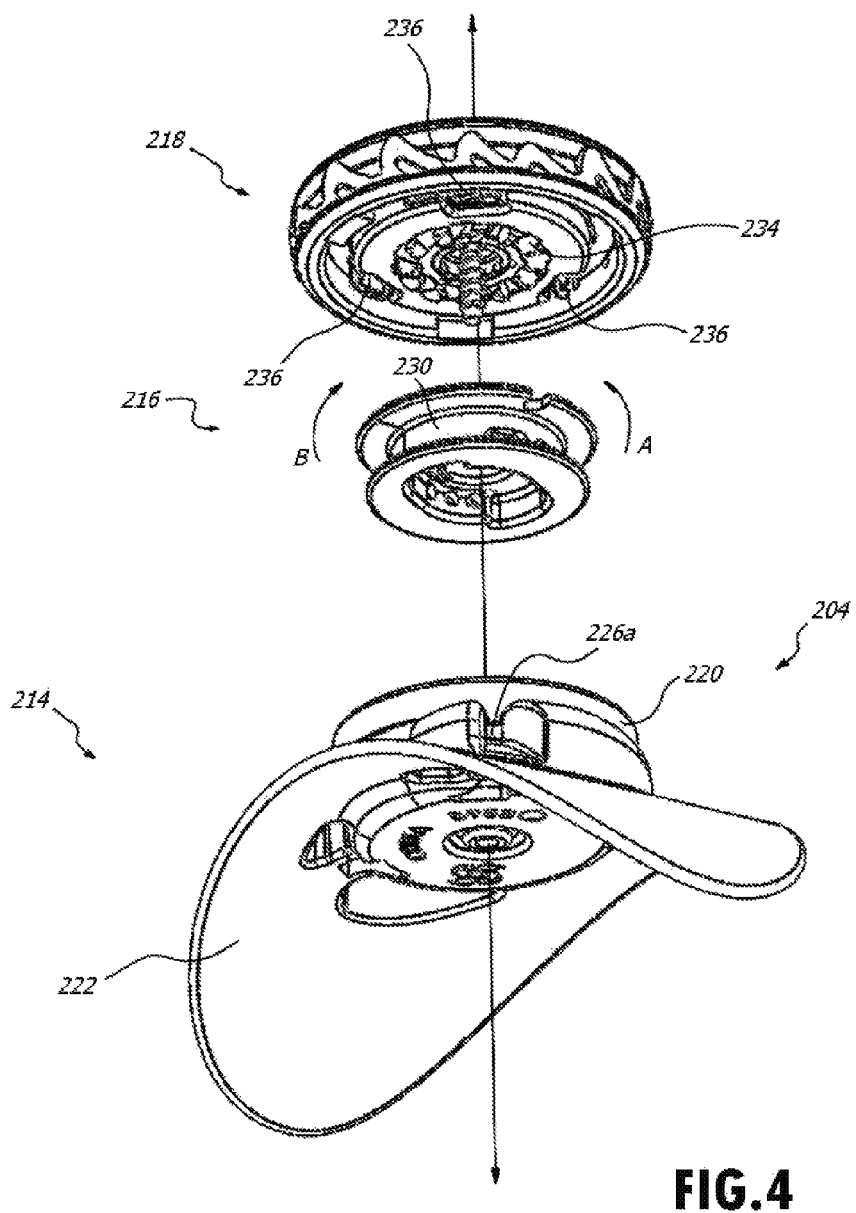

FIG. 2 is a perspective view of an embodiment of a closure device 200 that can be similar to the closure device of FIG. 1, or any other closure device described herein. The closure device can include a reel assembly 204 which can be similar to the reel assembly 104, or any other reel/knob assembly described herein. FIG. 3 is an exploded perspective view of the reel assembly 204. FIG. 4 is another exploded perspective view of the reel assembly 204. The closure device 200 that is illustrated in FIGS. 2-4 represents general reel based closure devices and illustrates common components of such devices. It should be realized that other reel based closure devices may include more or fewer components and/or have a modified configuration.

With reference to FIGS. 2 to 4, the reel assembly 204 can include a base member 214, a spool member 216, and a knob member 218. The base member can include a spool housing 22.0 and a mounting flange 222. The spool housing 220 can include a plurality of ratchet teeth 224, which can extend radially inwardly. The base member 214 can include lace holes (e.g., 226a) that allow the lace 206 to enter the spool housing 220.

The spool member 216 can be disposed within the spool housing 220 such that the spool member 216 is rotatable about an axis 228 with respect to the spool housing 220. The lace 206 can be secured to the spool member 216 such that when the spool member 216 rotates in a tightening direction (shown by arrow A) the lace 206 is drawn into the spool housing 220 and is wound around the channel 230 formed in the spool member 216, and when the spool member 216 rotates in a loosening direction (shown by arrow B) the lace 206 unwinds from the channel 230 of the spool member 216 and exits the spool housing 220 via the lace holes (e.g., 226a). The spool member 216 can also include spool teeth 232 formed thereon. It will be understood that the embodiments disclosed herein can be modified such that rotation in the direction shown by arrow B will tighten the lacing. In this particular embodiment, the knob member 218 may be raised axially to disengage from spool 230 to allow the spool to freewheel in direction B in order to release the lace. In other embodiments, rotation of the knob member 218 in the direction shown by arrow A may loosen the lacing system. In a specific embodiment, the knob member 218 may be rotated be a specific amount (e.g., ¼ to ½ turn) in a loosening direction (e.g., as shown by arrow A) to loosen the lacing system. Other user interfaces are possible for tightening, releasing, or adjusting lace tension.

The knob member 218 can be attached to the spool housing 220 such that the knob member 218 can rotate about the axis 228 with respect to the spool housing 220. The knob member 218 can include knob teeth 234 that can be configured to mate with the spool teeth 232 to couple the knob member 218 to the spool member 216 such that rotation of the knob member 218 in the tightening direction causes the spool member 216 to also rotate in the tightening direction. In some embodiments, the rotation of the knob member 218 in the loosening direction can also cause the spool member 216 to rotate in the loosening direction. The knob member 218 can also include one or more pawls 236 which can be biased radially outwardly so as to mate with the ratchet teeth 224. The pawls 236 and ratchet teeth 224 can be configured so that the ratchet teeth 224 can displace the pawls 236 radially inwardly when the knob member 218 is rotated in the tightening direction, thereby allowing the knob member 218 to rotate in the tightening direction. The pawls 236 and the ratchet teeth 224 can also be configured so that they engage one another when force is applied to twist the knob member 218 in the loosening direction, thereby preventing the knob member 218 from rotating in the loosening direction. In other arrangements, the ratchet teeth 224 may be oriented axially to engage knob pawl members (not shown) that are correspondingly arranged to mate axially.

Thus, a reel assembly such as reel assembly 204 can provide a one-way tightening system configured to allow a user to rotate the knob member 218 in the tightening direction, which causes the spool member 216 to rotate in the tightening direction, which in turn causes the lace 206 to be drawn into the spool housing 220 via the lace holes (e.g., 226a). As the lace 206 is drawn into the spool housing 220 the lacing system 200 can tighten, causing the lace guide 208 to be drawn in the direction toward the reel assembly 204 (shown by arrow C in FIG. 2). Although the lacing system 200 is shown with a single lace guide 208, any other suitable number of lace guides can be used. Other features of the reel and lacing system are described in U.S. Patent Application No. 2011/0266384, filed Apr. 29, 2011, and Titled "Reel Based Lacing System", the entire disclosure of which is incorporated herein by reference.

As described above, the embodiments described herein provide mechanisms that limit the tension that may be applied to a lace via a closure device, such as those illustrated in FIGS. 1-4. The mechanisms that provide tensioning limits typically include clutching mechanisms or components (hereinafter clutching mechanism) that may be placed within the closure device to limit the input force that is transferred from a user to one or more internal components of the closure device. Typically the clutching mechanism or component is designed to slip when a desired maximum input torque is achieved with the reel assembly—i.e., the lace reaches or attains a certain tension. In some embodiments, the tension limit at which the clutching mechanism slips may be set by a user of the device. In other embodiments, the tension limit at which the clutch mechanism slips may be predetermined or set by a third-party, such as by a physician or manufacturer.

In many applications the closure device is used in situations where the tension on the lace will be dynamic. For example, when the closure device is used to tighten shoes, the tension in the lace will vary as the user flexes and relaxes their foot, such as due to running, walking, jumping, flexing, and the like. This increase in lace tension is due to conditions other than the user operating the closure device's knob. in such embodiments, the tension on the lace may increase beyond an initially set tension threshold—i.e., a maximum tension limit that is set or desired for the closure device and/or clutching mechanism. In such instances, it may be desirable for the lace and closure device to withstand the higher tension loads that are placed on the lace in order to keep the shoe or other device closed. For example, if dynamic loads are being placed on the lace as a user runs or moves in a sporting event, it may be desirable to keep the shoe closed and tightened about the user's foot. In such instances, the closure device and clutching mechanism should be designed to withstand the higher dynamic loads, otherwise the user would have to continually retighten the shoe's lace. In many embodiments, the ability of the closure device to "withstand dynamic lace loading", and thus maintain a closure of an article, is achieved by preventing the closure device's spool from rotating in a direction that effects loosening of the lace (i.e., a loosening direction).

In other instances, it may be desirable for the lace and closure device to slip when relatively high tension loads are experienced in order to protect the user and/or device or components. For example, if dynamic loads are applied to the lace of a brace that is being worn by a patient, it may be desirable to allow the brace's lace and closure device to slip as the higher dynamic loads are applied. In such instances, slippage may keep the pressure applied by the brace to the patient's body part within a prescribed pressure range, which may reduce or eliminate loss of blood flow to the body part or the formation of scars or other damage to the body tissue. Slippage of the closure device in such instances may ultimately reduce damage to the body part and/or improve healing of the body part. In many embodiments, the ability of the closure device to "slip in response to dynamic lace loading" is achieved by allowing the closure device's spool to rotate in a direction that effects loosening of the lace (i.e., a loosening direction) when higher lace tensions are experienced. The embodiments of the closure devices described herein allow for the lace to withstand higher dynamic loads and/or slip when higher dynamic loads are applied as desired.

In some embodiments, the ability of the closure device and lace to withstand high dynamic loading of the lace, or to slip when higher dynamic loads are applied, may be achieved by varying the placement of a stop mechanism that prevents the closure device's spool for rotating in the loosening direction. In some embodiments, the stop mechanism includes a pawl mechanism, or pawl teeth, that engage with corresponding teeth of the closure device's housing (or a toothed plate or disc) in a ratchet like manner to allow the spool to rotate in a first direction (i.e., tightening direction) while preventing rotation of the spool in a second and opposite direction (i.e., loosening direction). Positioning of the stop mechanism relative to the clutching mechanism may prevent or allow slippage of the spool (i.e., rotation in the loosening direction) in response to dynamic lace tension loading as desired.

Figure 5:
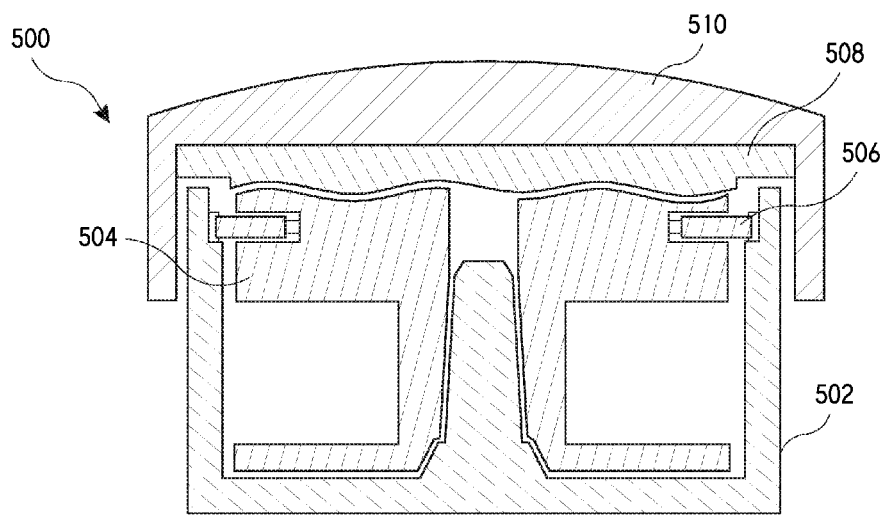
FIG. 5 illustrates an embodiment of a closure device having a tension limiting mechanism that is configured to withstand dynamic lace tension loading.

FIG. 5 illustrates one embodiment in which a closure device 500 is configured to withstand dynamic lace tension loading. As shown in FIG. 5, pawl teeth 506 (i.e., stop mechanism) are positioned such that they interact with the spool housing 502 and spool 504. In some embodiments, the pawl teeth 506 may be coupled directly with the spool 504 or be integral components thereof, while in other embodiments, the pawl teeth 506 may be coupled with a pawl disc (not shown) that is in turn coupled with the spool 504 via a spine, engaged teeth, or some other mechanism. A clutching mechanism 508 is positioned axially above the pawl teeth 506 and spool 504. Positioning of the pawl teeth 506 axially below the clutching mechanism 508 allows the closure device 500 to withstand dynamic loading or tensioning of the lace. Stated differently, because the pawl teeth 506 are positioned axially below the clutching mechanism 508, the slippage of the clutching mechanism 508 and knob 510 does not affect the interaction of the spool 504, pawl teeth 506, and spool housing 502. As such, the pawl teeth 506 hold or maintain the spool's position regardless of if dynamic lace loads are applied—i.e., the pawl teeth 506 prevent counter rotation or unwinding of the spool 504.

In some embodiments, a second clutch mechanism (not shown) may be used to allow slippage of the closure mechanism's spool, but at a tension greater than that provided by the clutch mechanism 508 that limits the input torque or tension. Stated differently, the closure device may include a first clutch mechanism that limits the input torque or tension applied by a user, and may include a second clutch mechanism that limits the dynamic lace tension loading that may occur. The second clutch mechanism may be configured to clip at a higher lace tension load than the first clutch mechanism in order to allow some dynamic lace tension loading to occur while preventing excessive lace tension loading that may damage the lace, closure device components, and/or damage bodily tissue. Accordingly, the user may use the article (e.g., shoe) for an activity (e.g., walking, running, and the like) without loosening the article's lace while being safeguarded from injury or other issues that may result from excessive lace tensioning.

Figure 6:
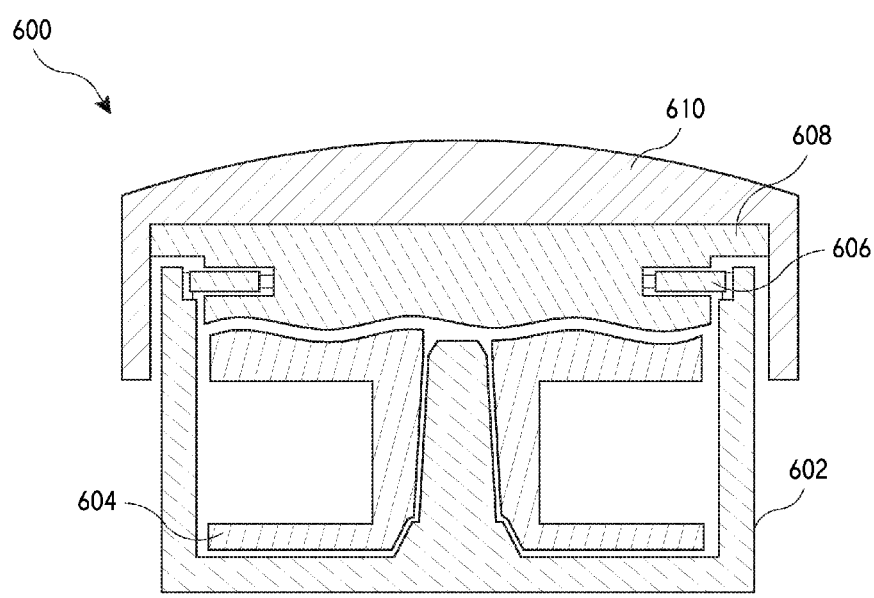
FIG. 6 illustrates an embodiment of a closure device having a tension limiting mechanism that is configured to slip when dynamic lace tension loads are applied or experienced.

In contrast, FIG. 6 illustrates one embodiment in which the closure device 600 is configured to slip when higher dynamic lace loads are applied or experienced. As shown in FIG. 6, the pawl teeth 606 are positioned such that they interact with the clutching mechanism 608 and spool housing 602. In some embodiments, the pawl teeth 606 may be coupled directly with the clutching mechanism 608 or be integral components thereof, while in other embodiments, the pawl teeth 606 may be coupled with a pawl disc (not shown) that is in turn coupled with the clutching mechanism 608. The spool 604 is positioned axially below the clutching mechanism 608. In this arrangement, the pawl teeth 606 do not directly affect the spool 604. Rather, the pawl teeth 606 indirectly affect the spool 604 via the clutch components of clutching mechanism 608 (e.g., wave like clutch teeth and the like). Because the clutch components of clutching mechanism 608 are used to hold the spool 604 in position (i.e., to prevent counter rotation or unwinding), the spool 604 will slip when a predetermined input torque is applied by a user and/or when the lace's tension level exceeds a threshold amount. In this manner, the closure device 600's "hold", or ability to prevent counter rotation, is limited to a predetermined input torque and lace tension threshold. As the lace experiences dynamic loading, the spool 604 counter-rotates within spool housing 602, which causes the lace to unwind slightly from around the spool thereby releasing or loosening the lace tension to some degree.

The configurations of FIGS. 5 and 6, or configurations similar to these embodiments, are provided to illustrate how the hold of a closure device may be modified based on a usage or need of the device. The remaining embodiments described herein (i.e., FIGS. 7A-11C) may employ similar pawl teeth, spool housing, spool, and/or clutch mechanism configurations in order to provide a limited or relatively infinite lace hold as desired. Stated differently, the embodiments of FIGS. 7A-11C may be modified as desired to allow the closure device to withstand higher dynamic loads or slip when such loads are applied. It should be noted that the interface between the clutch mechanism and spool in the cross section view of FIGS. 5-6 is illustrated having a wave like configuration. The wave like configuration is used merely to illustrate the positioning of the clutch/spool interface relative to the stop mechanism. In most embodiments, a cross section of the clutch/spool interface will not have a wave like configuration, but rather straight line or toothed configuration. As such, the wave like cross sectional clutch/spool interface is not physically representative of most of the embodiments described herein and such embodiments are not limited by illustration of FIGS. 5-6.

In other embodiments, the clutching mechanism may be designed to limit a user's input rather than directly limit the tension that may be applied. For example, the clutching mechanism may be configured to allow a user to rotate a knob of the closure device by only a specified amount. In this manner, the user's input to the knob is limited rather than the resulting tension that is applied to lace. In this manner, the clutching mechanism indirectly limits the lace tension that may be applied rather than directly limiting the lace tension via slippage of the clutch/spool interface. The tension that is ultimately applied to the lace may vary due to differences in a user's body part size, the closure device component configuration, and the like. In still other embodiments, the clutching mechanisms described herein may provide an audible feedback, tactile feedback, and/or visual feedback to indicate the amount of tension that is applied to lace and/or to indicate that a maximum amount of tension has been applied. In one embodiment, the audible feedback and/or tactile feedback may involve a clicking sound and/or sensation. The visual feedback may involve various indicators positioned on the knob that visually illustrates an amount of tension applied and/or that a tension limit has been reached. In some embodiments, the feedback indicator may be positioned on the lace, a knob, a lace guide, and the like. An indicator positioned on the lace may indicate a relative position of the lace with respect to the closure device rather than indicating an amount of tension applied to lace. These and other aspects of the tension limiting mechanisms will be more apparent with reference to the figures described below.

Referring now to FIGS. 7A-M, illustrated are embodiments of clutching mechanisms that utilize a wave clutch or similar type clutch component. For example, as illustrated in FIGS. 7A-D, a wave clutch mechanism 710 may be inserted between a knob 702 and a tension limiter component 703. The tension limiter component 703 may include a top member and a bottom member with a shaft member extending therebetween. The top member of clutch component 703 may be positioned axially above and/or within a recessed portion of a top surface of knob 702 while the bottom member is positioned axially below and/or within a recessed portion of a bottom surface of knob 702. A spring component 718 may be positioned between the top member of tension limiter component 703 and the top surface of knob 702. The wave clutch mechanism 710 may be positioned between the bottom member of tension limiter component 703 and the bottom surface of knob 702. Wave clutch mechanism 710 includes a top member 714 that is coupled with or otherwise integrally formed with the bottom surface of knob 702 and a bottom member 712 that is coupled with or otherwise integrally formed with the bottom member of tension limiter component 703.

The top member 714 and bottom member 712 each include teeth that have a wavelike or sinusoidal pattern. The wavelike teeth of bottom member 712 and top member 714 interact via friction to drive tension limiter component 703 as knob 702 is rotated by a user. As the tension in a lace (not shown) that is wound around spool 706 increases, an increased amount of friction between the wavelike teeth of bottom member 712 and top member 714 is required to drive spool 706. Eventually the friction required to drive bottom number 712 and spool 706 is sufficient enough that the wavelike teeth of bottom member 712 and top member 714 will being to slip, thereby preventing further tensioning of the lace. Spring 718 biases the top member 714 and bottom member 712 together and may be used to vary the frictional engagement of the teeth. Spring 718 may be removed and replaced with a stiffer or more flexible spring to bias the top member 714 and bottom member 712 together in a desired manner and thereby vary the frictional force required to cause slippage of the wavelike teeth, 714 and 712. Replacing the spring 718 in the manner may be used to increase or decrease the normal force, and thus the friction force, between the wave clutch mechanism 710 of top member 714 and bottom number 712. As can be readily understood, increasing or decreasing the frictional engagement of the top member 714 and bottom member 712 correspondingly increases or decreases the lace tension threshold at which the wave clutch mechanism 710 slips, thereby enabling more or less tension to be applied to the lace.

In some embodiments, a screw 716 may be threaded into a threaded protrusion 717 of housing 704 to couple the components together. In some embodiments, screw 716 may be accessible to a user to enable the user to remove one or more of the components, such as for repair or replacement. In other embodiments, the screw 716 may only be accessible by a physician, or other individual, using a specialized tool.

As shown in FIG. 7A, in one embodiment the pawl teeth 713 may be positioned on an interior surface of the knob 702. The pawl teeth 713 may interact with corresponding ratchet teeth 711 that are positioned on an interior surface of the housing 704. This configuration allows the spool 706 and tension limiter component 703 to slip within housing 704. Accordingly, in this configuration embodiment 700 would be unable to withstand dynamic lace tension loads. Instead, embodiment 700 would slip upon the application of dynamic lace tension loads. This configuration would be ideal for applications involving medical braces and/or any other application in which slippage due to dynamic tension loads is desired.

In other embodiments, the pawl teeth 713 may be positioned elsewhere to allow embodiment 700 withstand dynamic lace tension loads. For example, in some embodiments the pawl teeth 713 may be positioned on an outer surface of the spool 706 and configured to interact with corresponding ratchet teeth 711 positioned on an interior surface of housing 704. In this configuration, embodiment 700 would be able to withstand dynamic tension loads that are placed on the lace without slipping. This configuration would be ideal for applications involving shoes, boots, and other apparel or devices in which slippage due to dynamic tension loads is not desired.

Figure 7E:
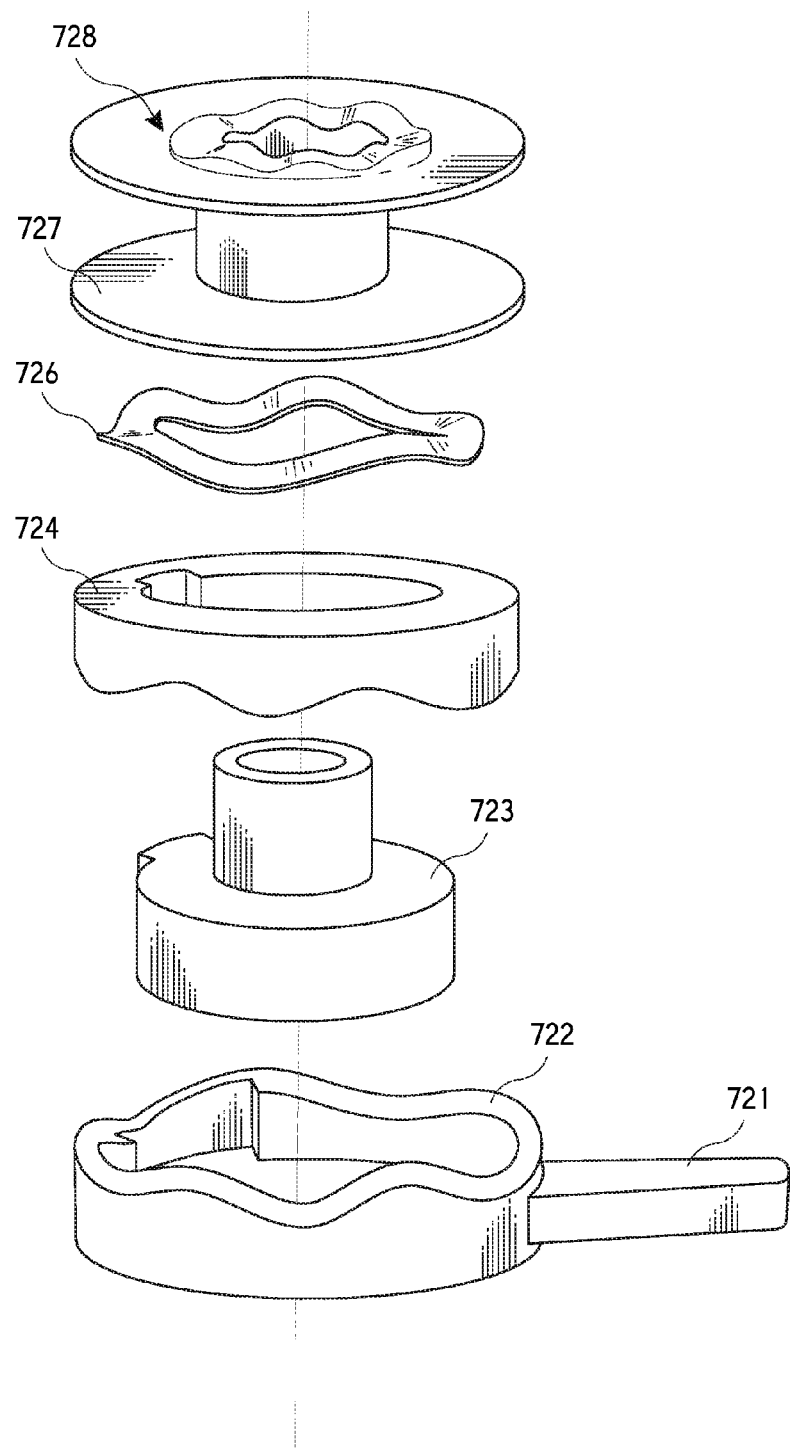
Figure 7F:
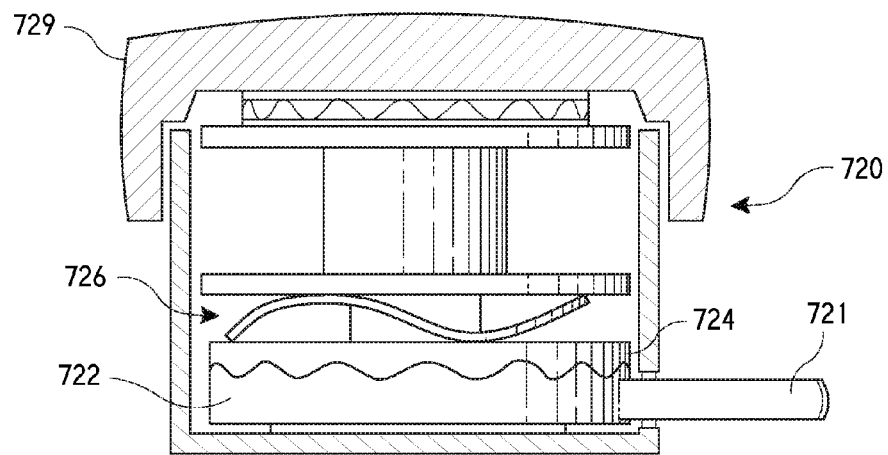
Figure 7G:
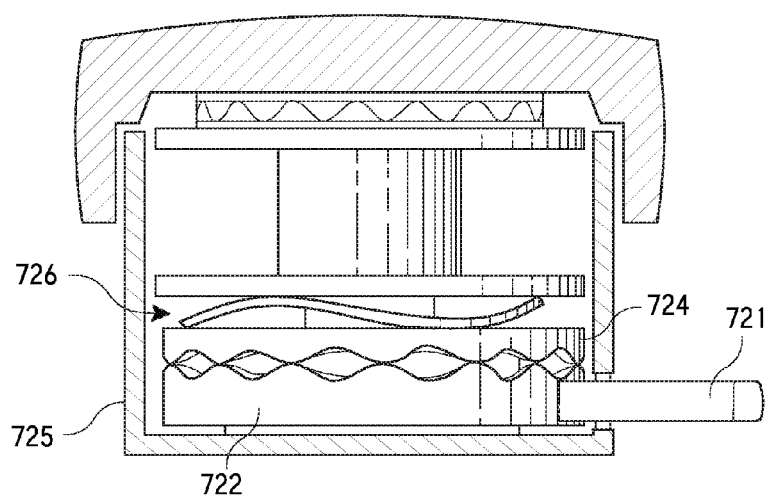

FIGS. 7E-G illustrate another embodiment of a closure device 720 that includes a clutching mechanism. Closure device 720 includes a housing 725 and knob 729 as previously described. Positioned on a bottom surface of knob 729 and on a top surface of the spool 727 is a tension limiting mechanism 728 (e.g., wave clutch). Tension limiting mechanism 728 may include a wavelike teeth pattern as previously described, or any other tooth pattern described herein, that allows a top and bottom component of the tension limiting mechanism 728 to slip relative to one another when a certain input torque and/or lace tension is achieved. A spring 726 is positioned on a bottom surface of spool 727 and on a top surface of a top cam component 724. Positioned axially below the top cam component 724 is a bottom cam component 722. The bottom cam component 722 includes a handle portion 721 that may be rotated by a user to cause the top cam component 724 and bottom cam component 722 two axially separate as shown in FIGS. 7F-G. The top cam component 724 and bottom cam component 722 include cam surfaces that causes the components to axially separate as handle 721 is rotated by a user. A post or protrusion 723 that is coupled with a bottom surface of housing 725 includes a key member that couples with top cam component 724 to prevent rotation of the top cam component 724 as bottom cam portion 722 is rotated via handle 721. This allows the cam surfaces of top cam component 724 and bottom cam component 722 to cause axial separation of the components as the handle portion 721 is rotated by a user. Bottom cam component 722 may include a slot (not numbered) within which the key member slides as bottom cam component 722 is rotated relative to the top cam component 724.

The axial separation of the top cam component 724 from the bottom cam component 722 compresses spring 726 positioned between the top surface of top cam component 724 and the bottom surface of spool 727. Compression of spring 726 increases the normal force, and thus frictional force or engagement, of tension limiting mechanism 728 such that tension limiting component 728 is prevented from slipping until a greater input torque and/or lace tension force is achieved. In this manner, a user is easily able to adjust the tension limiting properties or tension slippage threshold of closure device 720.

Figure 7H:
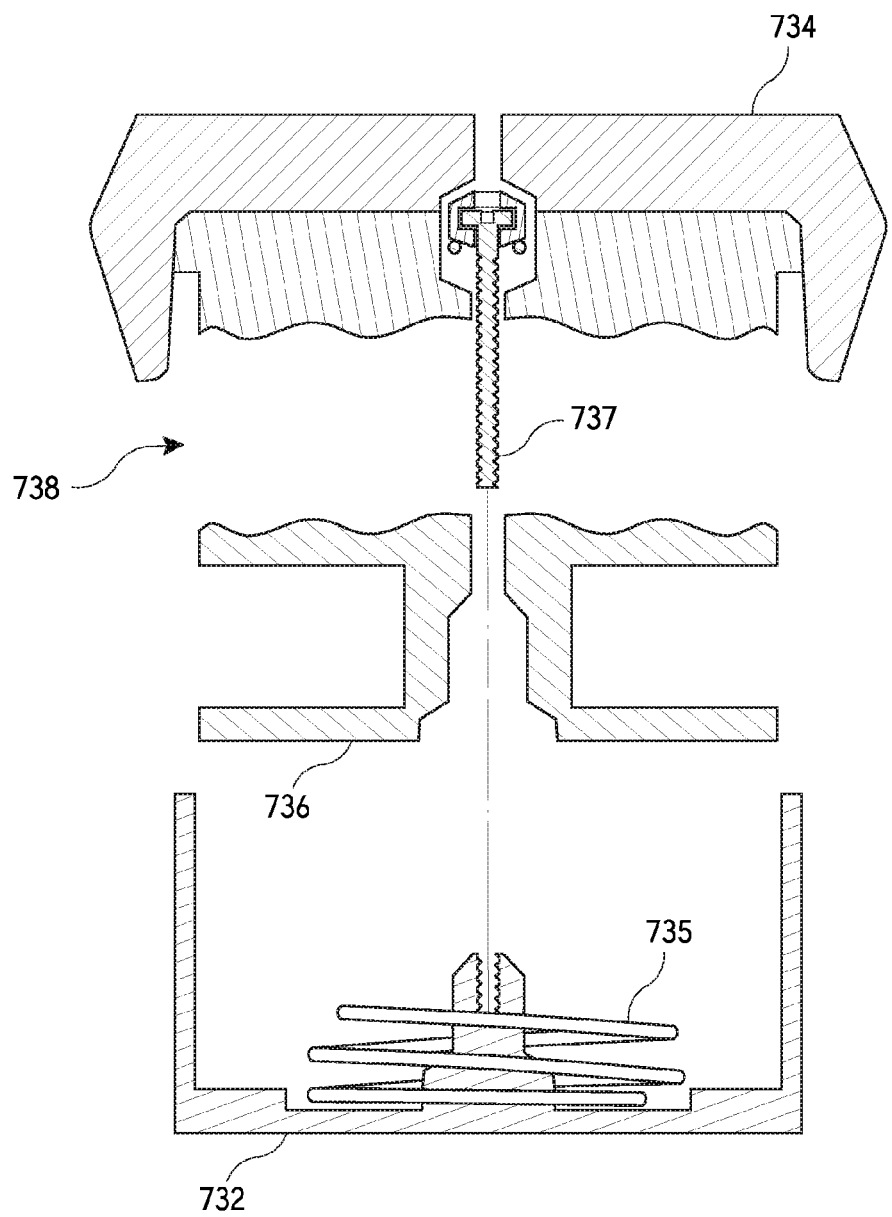
Figure 7I:
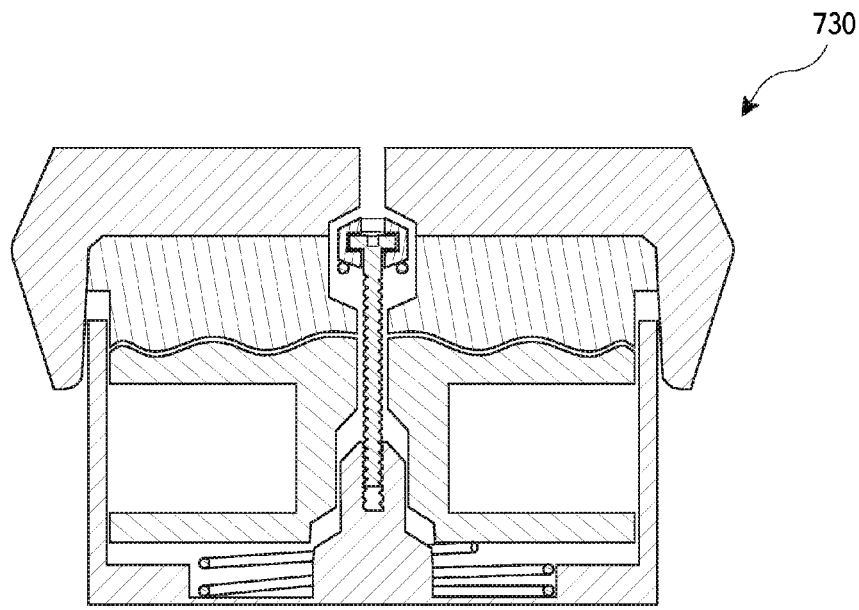
Figure 7J:
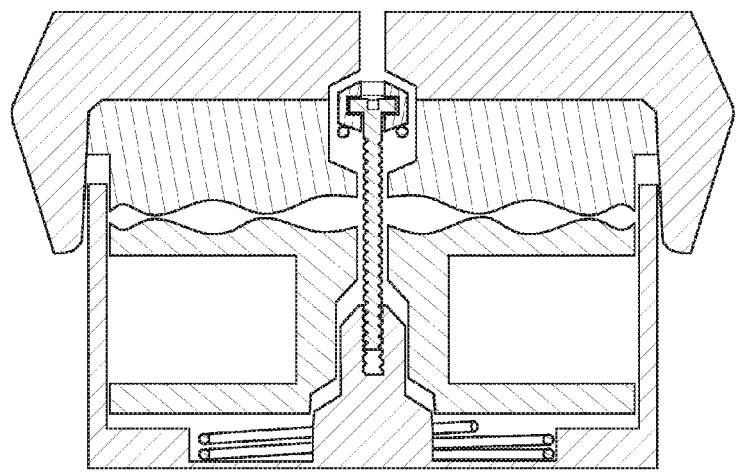

FIGS. 7H-J illustrate yet another embodiment of a closure device 730 comprising a clutching mechanism. Closure device 730 includes a knob 734, spool housing 732, and spool 736. The tension limiting mechanism 738 is positioned between a top surface of spool 736 and a bottom surface of knob 734. Tension limiting mechanism 738 may include a wavelike tooth pattern and/or any other pattern that allows slippage of the top component and bottom component of tension limiting mechanism 738. A spring 735 is positioned between the bottom surface of spool 736 and spool housing 732. Spring 735 biases spool 736 axially upward to apply a friction force between the bottom component and top component of tension limiting mechanism 738. A screw 737 or other closure component may be inserted through knob 734 and spool 736 and coupled with housing 732. Screw 737 may be adjusted to compressed spring 735 via tension limiting mechanism 738 and spool 736. Compressing spring 735 increases the normal force, and thus the frictional force or engagement, between the top component and bottom component of tension limiting mechanism 738. In this manner, the input torque and/or lace tension required to cause slippage of the tension limiting mechanism 738 may be varied. In some embodiments, a bottom portion of housing 732 may be adjusted (e.g., rotated) to compress spring 735 and thereby vary the normal force between the top and bottom components of tension limiting mechanism 738. In some embodiments, adjusting the bottom portion of the housing 732 may cause the screw 737 to move axially upward or downward and thereby compress spring 735. FIGS. 7I-J illustrate the operation of the tension limiting mechanism 738. Specifically, these figures illustrate the top and bottom components of tension limiting mechanism 738 in a fully engaged position and in a position in which the plates are slipping relative to one another.

Figure 7K:
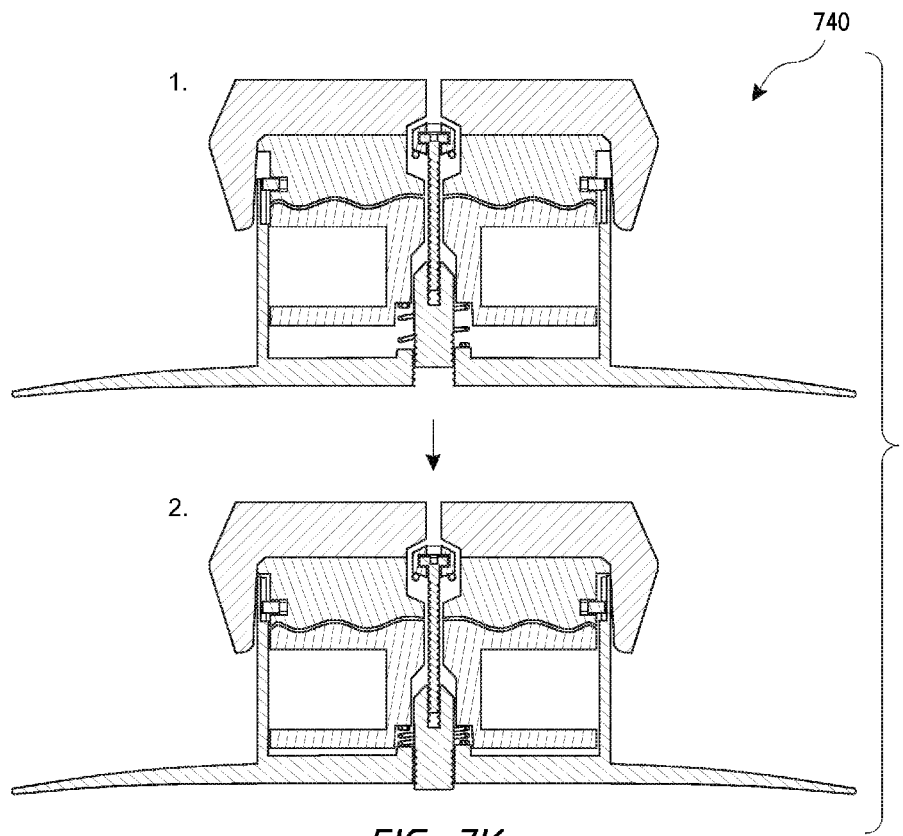
Figure 7L:
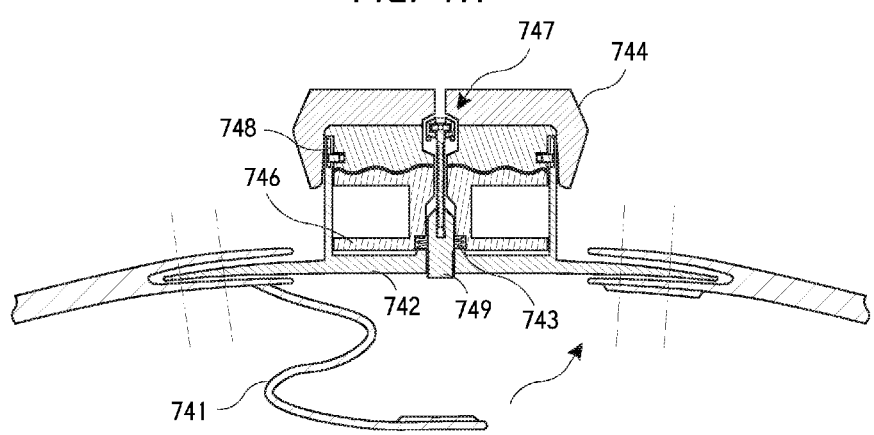

FIGS. 7K-L illustrate another embodiment of a closure device 740 that includes a clutching mechanism 748. The closure device 740 of FIGS. 7K-L is similar to the closure device 730 of FIGS. 7H-J, in that closure device 740 includes a knob 744, spool housing 742, spool 746, and spring component 743 having a similar arrangement to closure device 730. In some embodiments, the top surface of spool 746 of closure device 740 may function as the bottom component of tension limiting mechanism 748. In such embodiments, the top surface of spool 746 may interact with a top component of tension limiting mechanism 748 to provide slippage of the two components when a predetermined input torque and/or lace tension threshold is achieved. In some embodiments, the bottom surface of knob 744 may function as the top component of tension limiting mechanism 748.

FIGS. 7K-L further illustrate the top component of tension limiting mechanism including pawl teeth (not numbered) that interact with corresponding ratchet teeth of housing 742. This configuration allows the spool 746 to slip when a dynamic load is applied to the lace. In another configuration, spool 746 may include the pawl teeth interact with corresponding ratchet teeth of housing 742. This configuration would not allow slippage of the spool 746 as a dynamic load is applied. Rather, this configuration would provide an essentially infinite hold of the lace regardless of the dynamic lace tension applied.

In some embodiments, closure device 740 may be coupled with apparel or a device so that access to a bottom of the closure device is provided. In such embodiments, a strap 741 may be positioned across the bottom surface of the closure device 740 and coupled in a closed position over the bottom surface of closure device 740 via Velcro® or another fastening component. Strap 741 may be uncoupled to expose the bottom surface of closure device 740. Exposing the bottom surface of closure device 740 may allow a screw or other fastening component to be adjusted to compresses spring 743 and thereby vary the tension limiting capability of tension limiting component mechanism 748 as described herein.

Figure 7M:
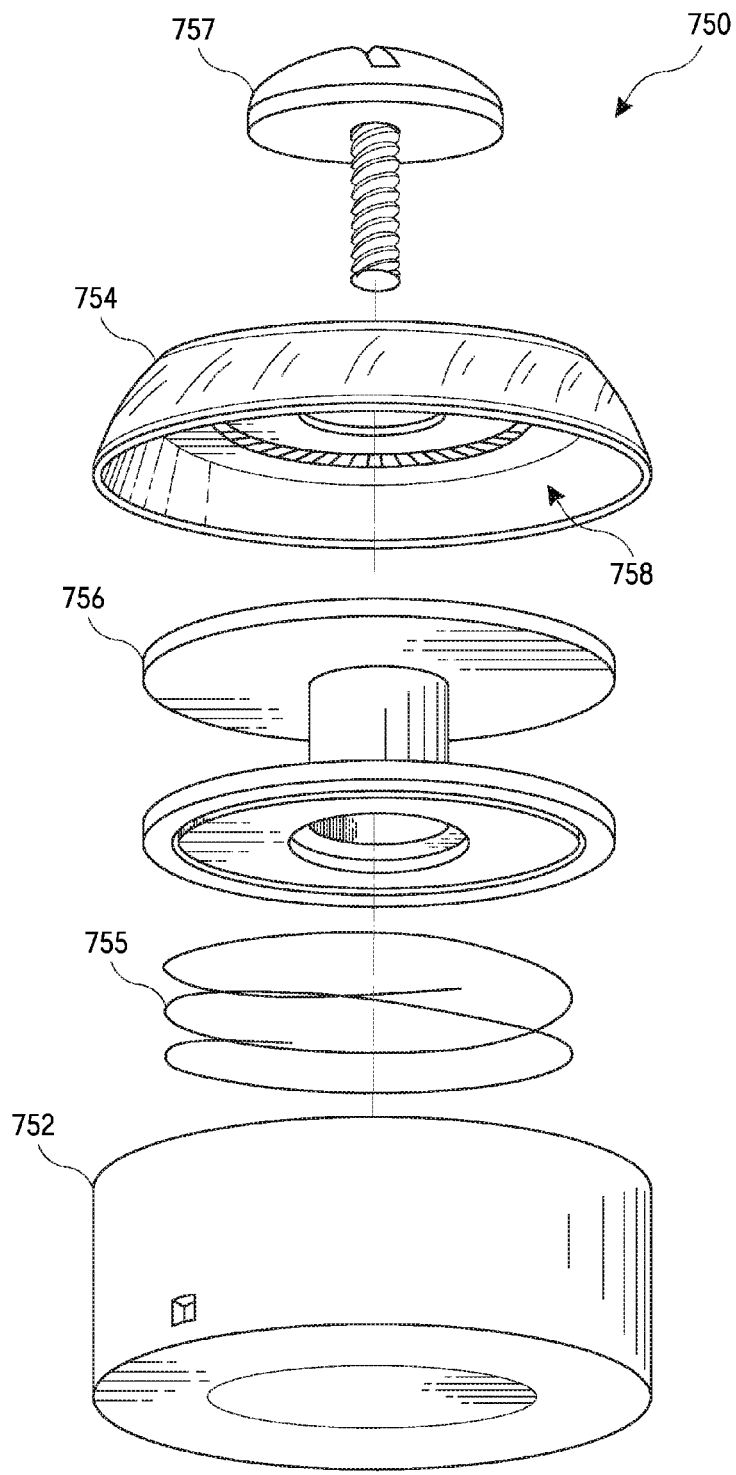

FIG. 7M illustrates another embodiment of a closure device 750 that includes a clutching mechanism. As in some of the previous embodiments, closure device 750 includes a spool housing 752, spool 756, knob 754, and tension limiting mechanism 758 positioned between the bottom surface of knob 754 and a top surface of spool 756. A spring 755 is positioned between a bottom surface of spool 756 and spool housing 752. Spring 755 may be compressed as previously described to vary the tension limiting capabilities of tension limiting mechanism 758. Tension limiting mechanism 758 may be similar to any of the tension limiting mechanisms described herein. In one embodiment, tension limiting mechanism 758 includes saw-like teeth that are positioned relative to one another to allow slippage of the teeth. Specifically, the saw-like teeth of tension limiting mechanism 758 are configured so that when the knob 754 is rotated in a tightening direction, the angled portions of the saw-like teeth press against one another. As the tension in the lace is increased, the angled or ramped portions of the saw-like teeth begin to slide relative to one another such that when a predetermined input torque and/or lace tension is achieved, the top teeth will slide relative to the bottom teeth without further tensioning the lace. As in some of the other embodiments, closure device 750 includes a screw 757 or other fastening mechanism that may be adjusted to increase or decrease the pressure applied to the saw-like teeth of tension limiting mechanism 758. As described previously, adjusting the pressure applied to the teeth varies the friction force between the teeth and, thus, varies the input torque and/or lace tension that must be achieved in order to cause slippage of the tension limiting mechanism 758.

Figure 8A:
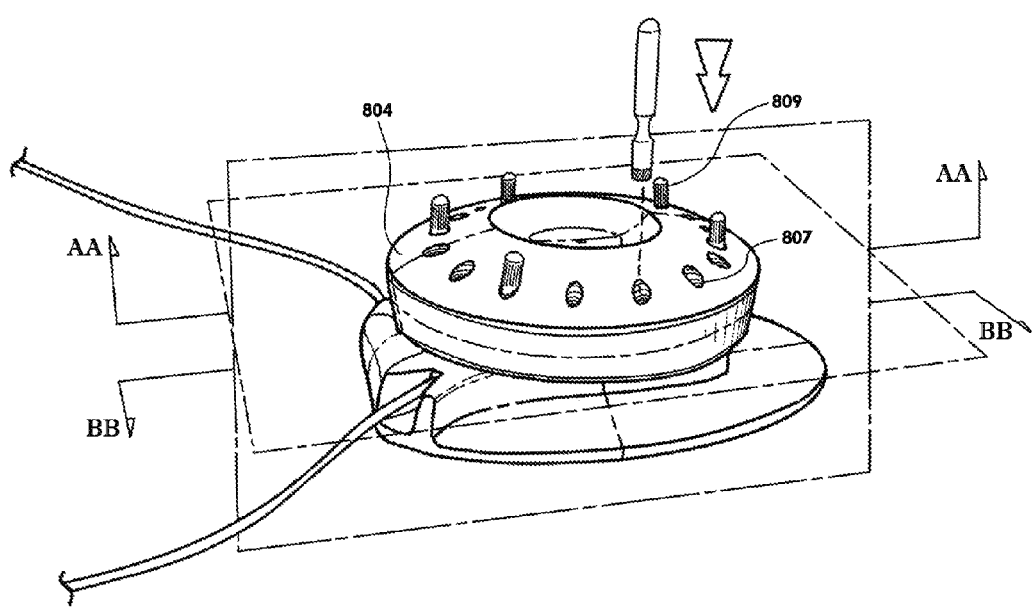
FIGS. 8A-II illustrate embodiments of closure devices and/or tension limiting mechanisms that utilize decent-like components or mechanisms.
Figure 8B:
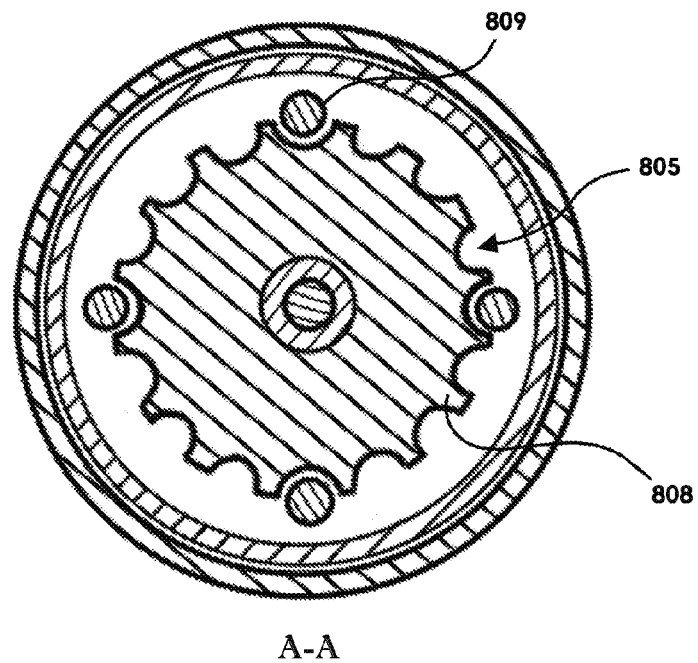

Referring now to FIGS. 8A-II, illustrated are embodiments of closure devices that include clutching mechanisms that utilize detent-like components to allow slippage of the closure device. For example, FIGS. 8A-E illustrate an embodiment of a closure device 800 that includes a spool housing 802, a knob 804, and a spool 806. As shown in greater detail in FIG. 8E and the cross section A-A of FIG. 8B, positioned on a top surface of spool 806, or integrally formed therewith, is a tension limiting component 808 that includes a plurality of notches 805 positioned circumferentially around an outer edge of the tension limiting component 808. In another embodiment, the notches 805 may be positioned on a top surface of the tension limiting component 808.

Figure 8C:
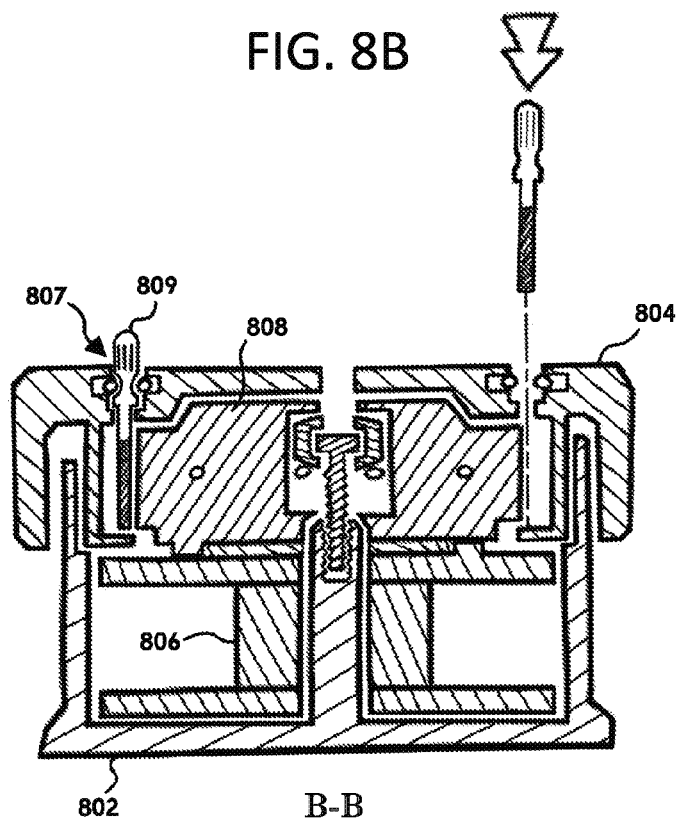
Figure 8D:
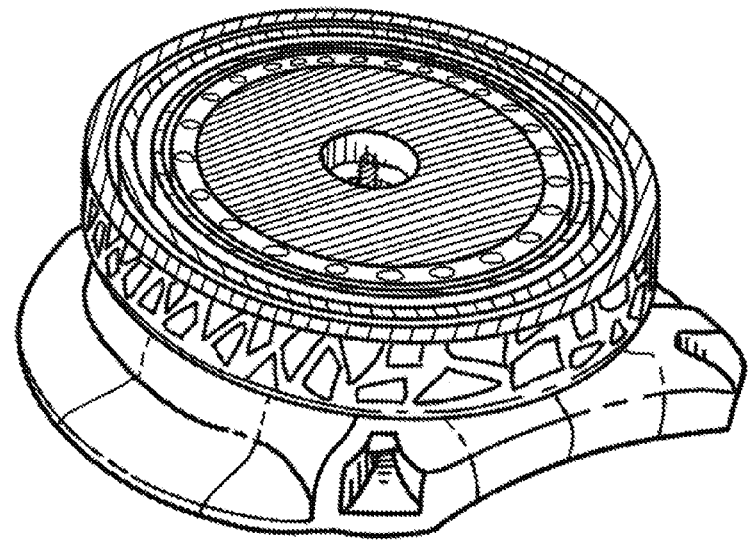
Figure 8E:
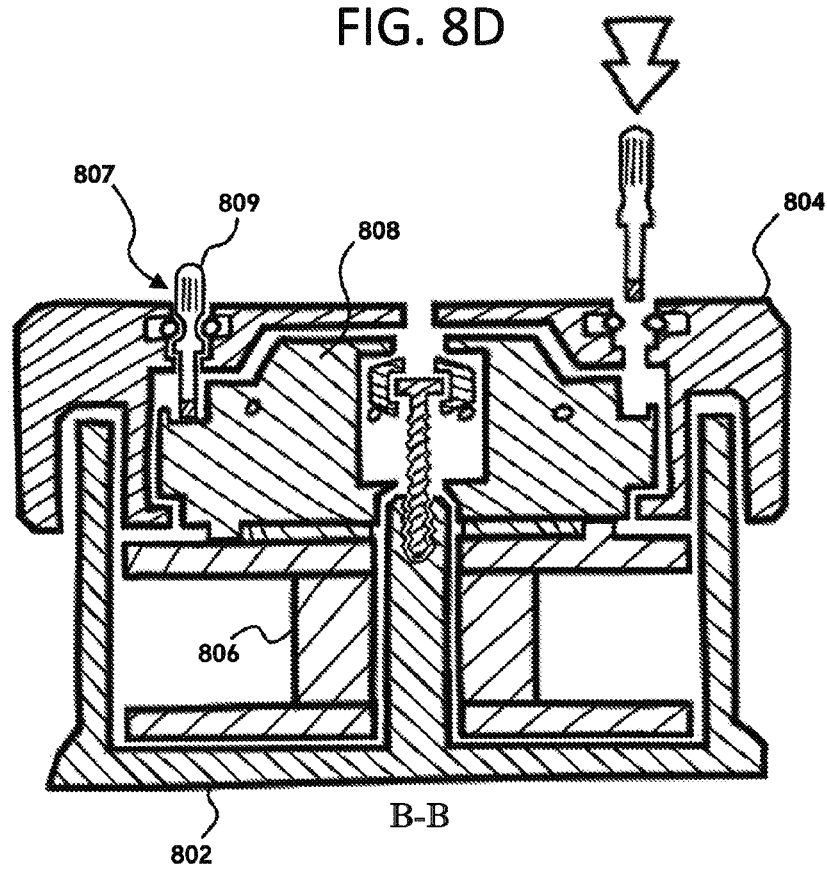

As shown in greater detail in FIGS. 8A and 8E and the cross section B-B of FIG. 8C, knob 804 includes a plurality of apertures 807 that are each arranged so as to be positioned axially above one of the notches 805 of tension limiting component 808. Pins 809 may be inserted through apertures 807 so that a portion of the pin 809 is positioned within a notch 805 of tension limiting component 808. In one embodiment, a distal end of the pin 809 may be positioned within a notch 805 that is positioned on a top surface of tension limiting component 808. In another embodiment, a main body or shaft of the pin 809 may be positioned within a notch 805 that is positioned on the outer edge of tension limiting component 808. The pins 809 mechanically resist slippage between the knob 808 and the tension limiting component 808 in a detent-like manner. Specifically, the pins 809 remain within the notches 805 until a predetermined input torque and/or lace tension threshold is achieved. After the predetermined input torque and/or lace tension threshold is achieved, the pins 809 deflect radially out of the notches 805 so that the knob 804 slips relative to tension limiting component 808.

A desired number of pins 809 may be inserted within the apertures 807 in order to achieve a desired slippage of the knob 804 and tension limiting component 808. For example, when slippage of the closure device 800 is desired at a relatively low input torque and/or lace tension threshold, only a few pins 809 may be inserted within apertures 807 to lower the overall mechanical resistance of the closure device 800. In contrast, when slippage of the closure device 800 is desired at a relatively high input torque and/or lace tension threshold, more pins 809 may be inserted within apertures 807 to increase the overall mechanical resistance of closure device 800. In some embodiments, the pins 809 may be provided to a user to allow the user to easily modify the input torque and/or lace tension limiting capabilities of the closure device 800. In another embodiment, only a physician or third-party may have access to the pins 809 to modify the closure device's input torque and/or lace tension limiting capabilities. As previously described, the arrangement of the closure device 800's pawl teeth may be selected so as to allow or prevent slippage of the spool 806 upon application of a dynamic lace tension loads as desired.

Figure 8F:
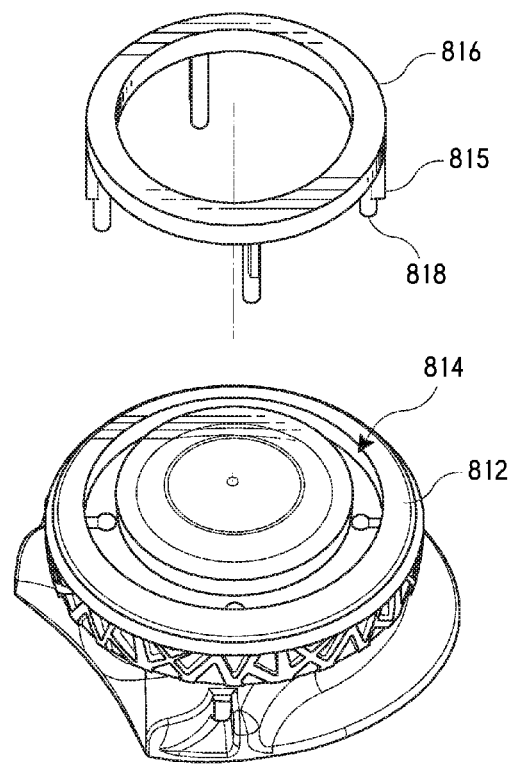
Figure 8G:
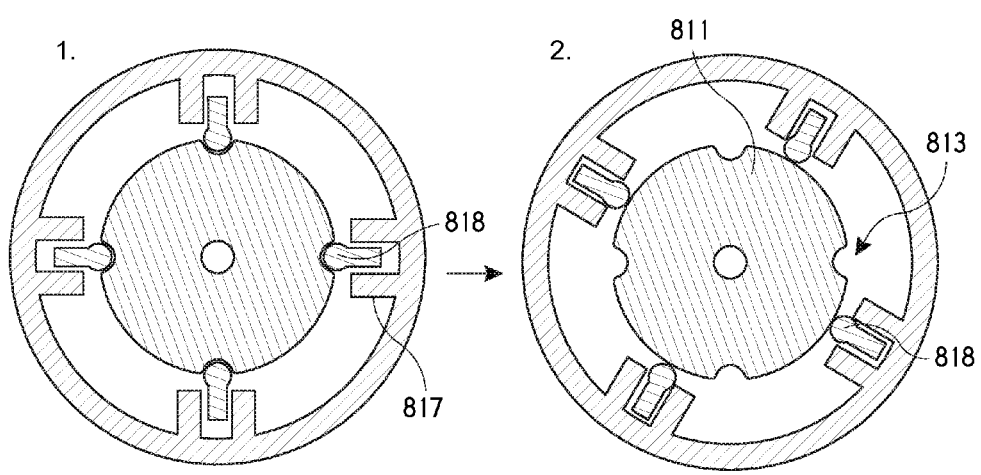
Figure 8H:
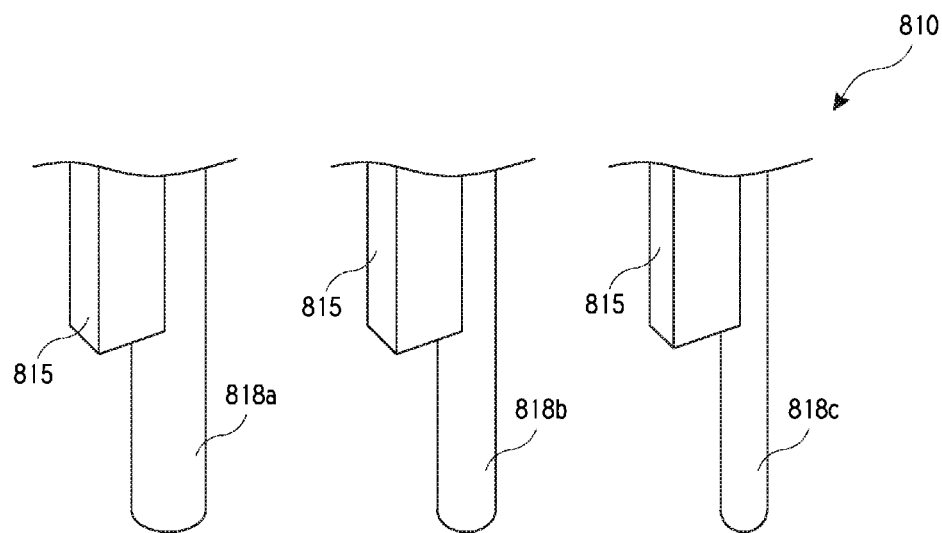

FIGS. 8F-H illustrate another embodiment of a closure device 810 having a clutching mechanism that functions in a detent-like manner. Specifically, closure device 810 includes a knob 812 having and annular slot 814 within which a flexible ring 816 is placed. Internally mounted within closure device 810 and under knob 812 is a tension limiting component 811 that includes a plurality of notches 813. Flexible ring 816 includes a plurality of shafts 818 that extend axially downward from the bottom surface of flexible ring 816. Shafts 818 are configured to be positioned within the notches 813 of tension limiting component 811. As previously described, shafts 818 remain within the notches 813 of tension limiting component 811 until a predetermined input torque and/or lace tension threshold is achieved. Shafts 818 are configured to flex radially outward and out of notches 813 when the predetermined input torque and/or lace tension threshold is achieved in order to allow slippage of the knob 812 relative to tension limiting component 811.

Knob 812 includes a plurality of drive components or keys 817 that press against corresponding drive components 815 of the shafts 818 in order to drive flexible ring 816 and tension limiting component 811 as knob 812 is rotated by a user. In some embodiments the drive components 817 may include rectangular members that extend axially downward and radially inward from knob 812. As shown in FIG. 8H, the corresponding drive components 815 of the shafts 818 may also be rectangular shaped members that are insertable between two drive components 817 of knob 812. The drive components 815 of the shafts 818 may be positioned on an upper end of the shafts to allow a lower end of the shafts 818 to flex radially outward and into and out of the notches 813. As also shown in FIG. 8H, a diameter of the shafts 818 may be varied to increase or decrease the stiffness of the shafts. For example, flexible ring 816 may include relatively large diameter shafts 818a, relatively small diameter shafts 818c, or mid-diameter shafts 818b. The large diameter shafts 818a may be stiffer than the mid-diameter shafts 818b and small diameter shafts 818c, which may allow a greater input torque and/or lace tension to be applied before the flexible ring 816 and knob 812 slip relative to tension limiting component 811. A user may select the appropriate flexible shaft 816 to achieve a desired input torque and/or lace tension threshold before slippage of the knob 812 and tension limiting component 811.

FIGS. 8I-L illustrate another embodiment of a closure device 820 having a clutching mechanism that functions in a detent-like manner. Specifically, knob 822 of closure device 820 includes a plurality of apertures 827 through which a U-shaped spring 828 is inserted. U-shaped spring 828 includes a pair of inwardly disposed shaft portions 826 that are configured to fit within notches 823 of a tension limiting member 821, which is disposed within closure device 820. The U-shaped spring 828 is inserted through apertures 827 until the inwardly disposed shaft portions 826 fit within the notches 823 of the tension limiting member 821. The inwardly disposed portions 826 of U-shaped spring 828 are used to drive the tension limiting member 821 as knob 822 is rotated by a user. As the tension of the lace of closure device 820 is increased, the U-shaped spring 828, and specifically the inwardly disposed shaft portions 826, begins to flex radially outward. Upon achieving or exceeding a predetermined input torque and/or lace tension threshold, the inwardly disposed shaft portions 826 flex radially outward sufficiently such that the inwardly disposed shaft portions 826 slide out of the notches 823 and the knob 822 slips relative to the tension limiting member 821.

Figure 8I:
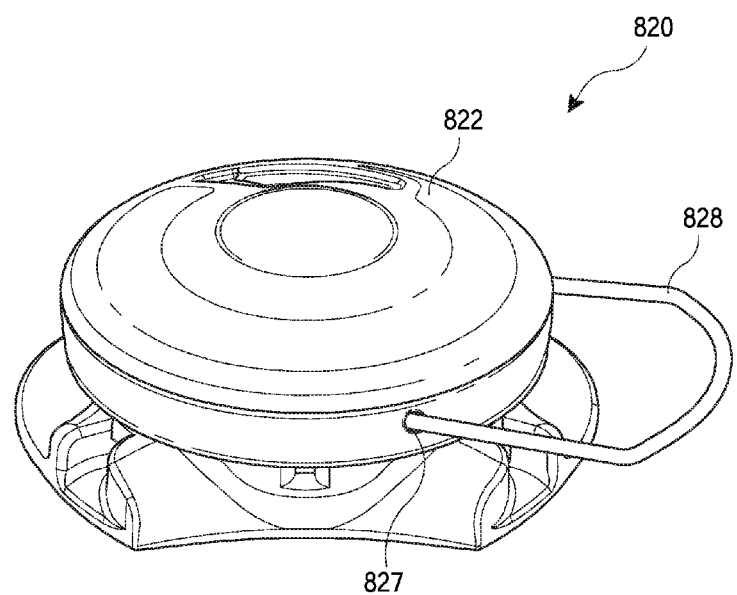
Figure 8J:
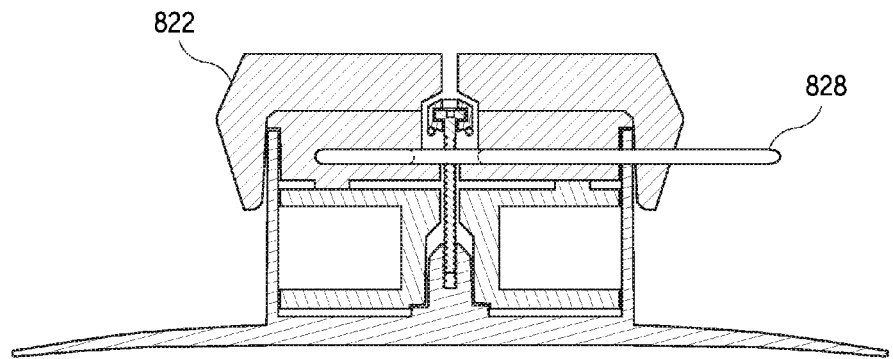
Figure 8K:
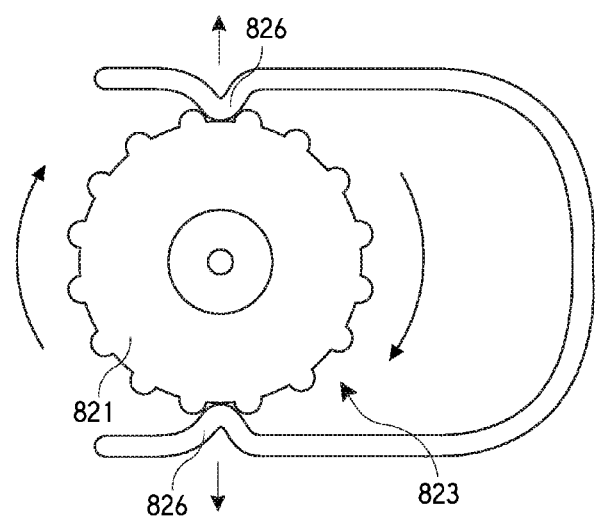
Figure 8L:
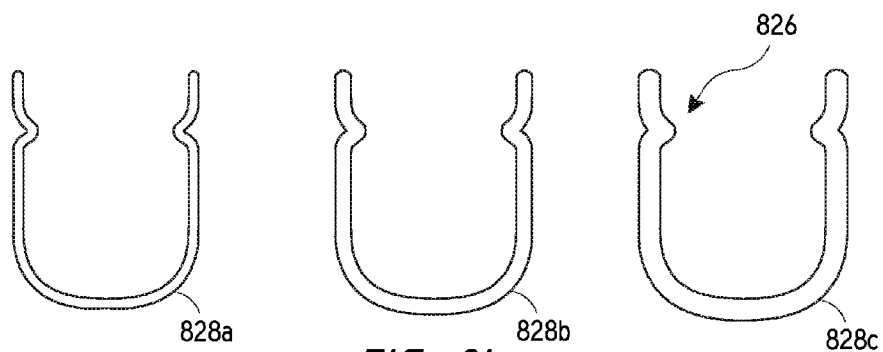

FIG. 8L illustrates that the diameter of the tension limiting member 828's shaft may be varied 828a-c so as to vary the spring force that presses the inwardly disposed shaft portions 826 into notches 823. In this manner, the input torque and/or lace tension limiting capabilities of the closure device 820 may be varied by selecting an appropriate tension limiting member 828a-c. For example, the tension limiting member 828 may be replaced with a stiffer or more flexible tension limiting member 828a-c as desired to achieve a desired amount of slippage between the knob 828 and tension limiting member 828.

Figure 8M:
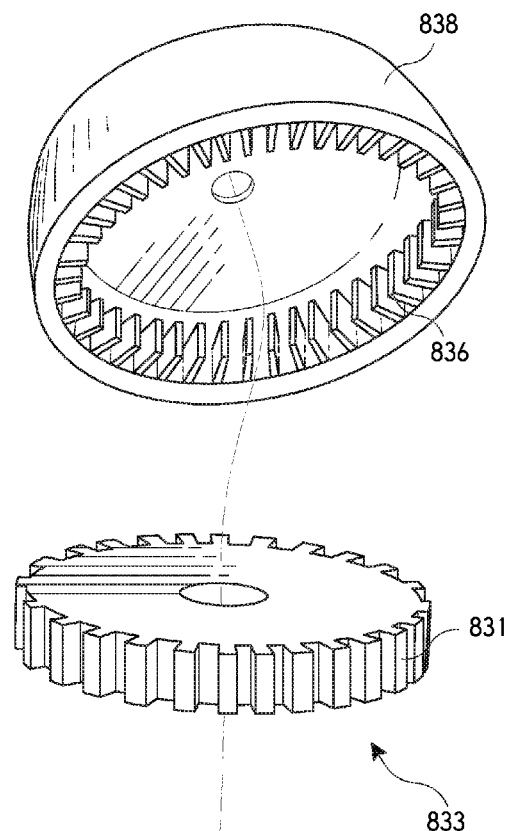
Figure 8N:
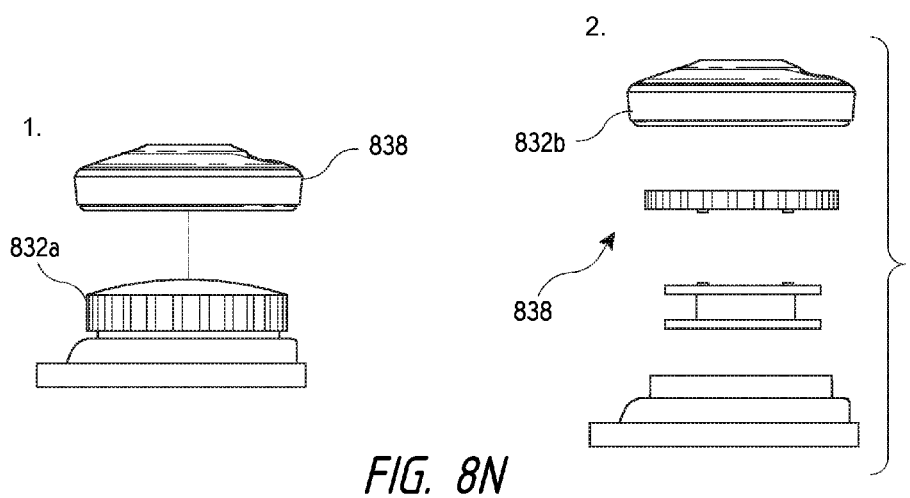
Figure 80:
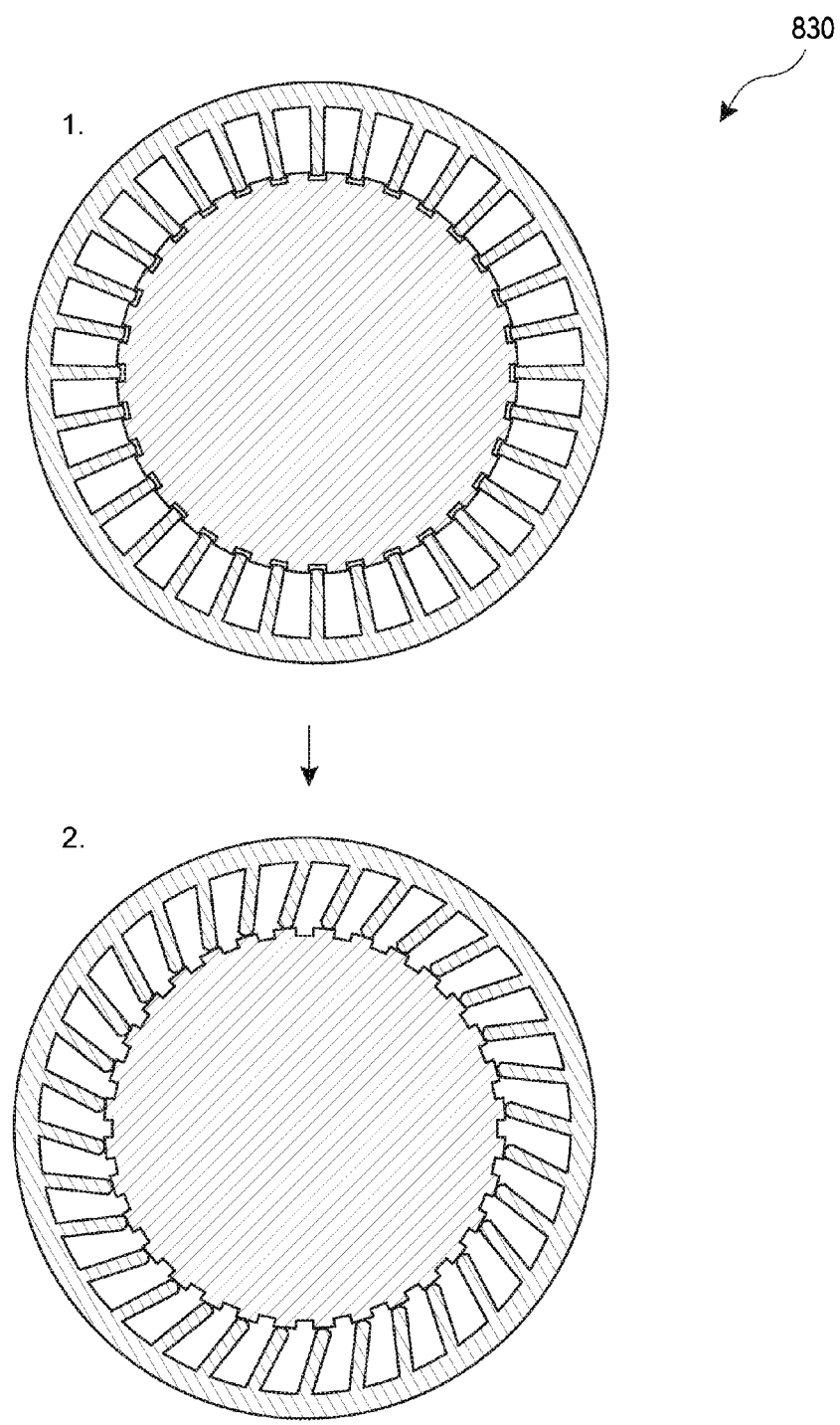

Referring now to FIGS. 8M-O, illustrated is another embodiment of a closure device 830 that includes a clutching mechanism that functions in a detent-like manner. Specifically, closure device 830 includes a cap member 838 that includes a plurality of protrusions 836 that protrude radially inward from and are positioned circumferentially around an inner surface of cap member 838. The protrusions 836 are configured to be positioned within notches 833 of a disc 831. The interaction of the protrusions 836 and notches 833 drive the disc 831 when the cap member 838 is rotated by a user, which in turn drives a spool and tensions the lace. Similar to the embodiments previously described, when the input torque and/or lace tension of closure device 830 reaches a predetermined threshold, the protrusions 836 flex and/or displace out of the notches 833 of disc 831 such that the cap member 838 slips relativity disc 831 (see FIG. 8O).

As shown in FIG. 8N, in one embodiment the cap member 838 may be positioned over a knob 832a of closure device 830. In this embodiment, the knob 832a would function as the disc 831 and include the notches 833. In such embodiments, a cap member 838 could be selected based on the stiffness of the protrusions 836 and used with knob 832a to appropriately tension the lace to near a desired tension threshold. In other embodiments, the cap member 838 may be positioned internally within closure device 830 and an external knob 832b may be rotated to rotate cap member 838 and disc 831.

Figure 8P:
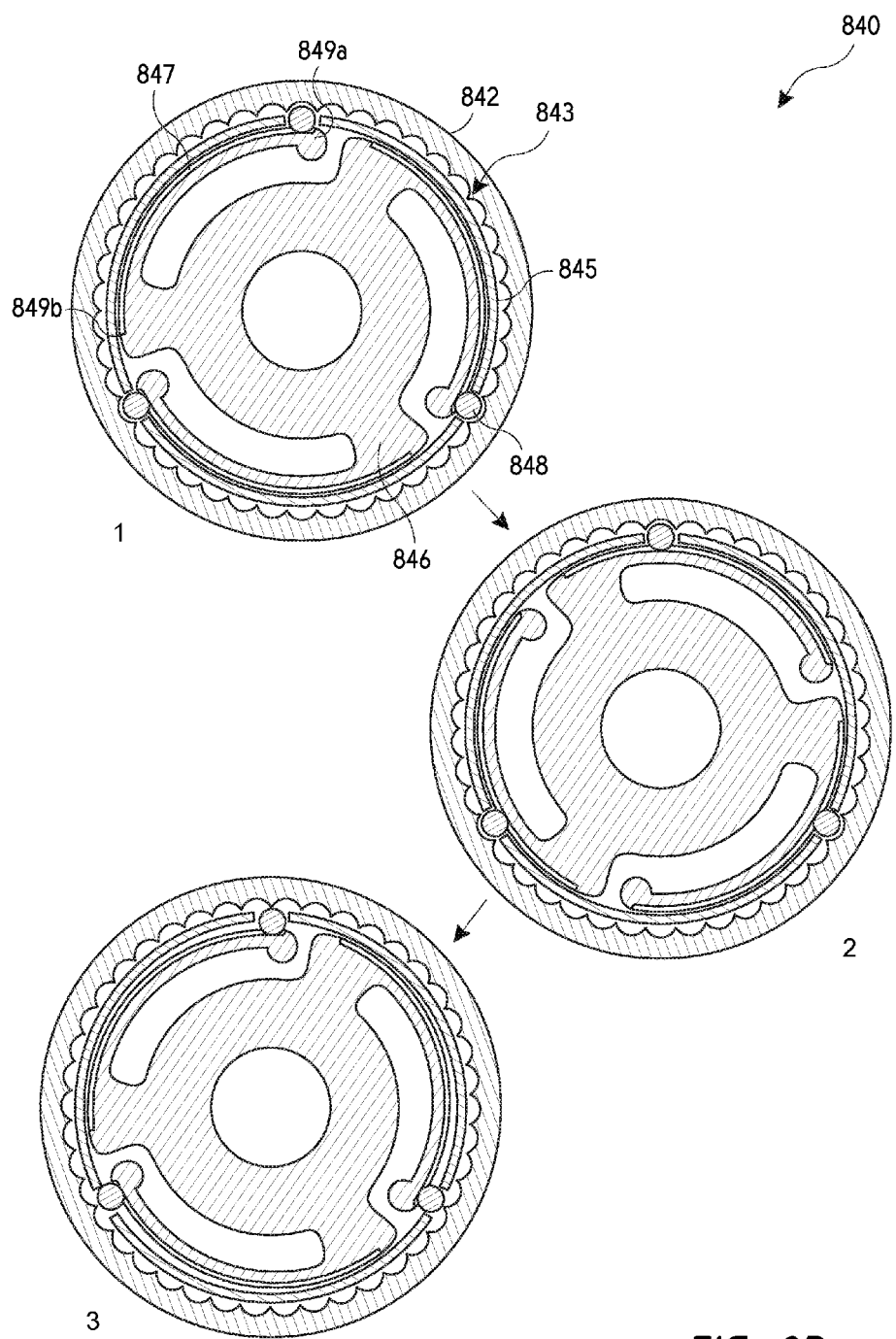
Figure 8S:
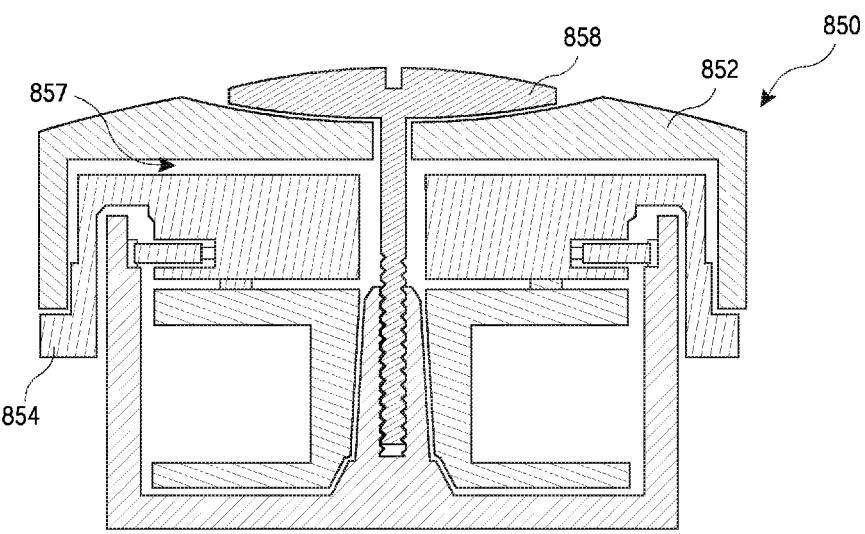

Referring now to FIGS. 8P-R, illustrated is another embodiment of closure device 840 that includes a clutching mechanism. In this embodiment, a knob 842 includes a plurality of notches 843 within which ball bearings 848 are positioned. The ball bearings 848 are used to drive a disc 845 as knob 842 is rotated. Disc 845 includes one or more slots 841 that are configured to receive the ball bearing 848. An adjustable spring plate 846 is positioned between the disc 845 and the knob 842. Adjustable spring plate 846 includes a plurality of arms 847 that each have a channel formed therein within which a respective ball bearing 848 is positioned.

The adjustable spring plate 846 is rotatable relative to disc 845 to move the ball bearing 848 within the channel of arm 847 between a distal end 849a and a proximal end 849b. The arm 847 is coupled with a body portion of adjustable spring plate 846 in a cantilever like manner with the proximal end 849b integrally formed with, or otherwise rigidly coupled to, the body portion of the spring plate 846 while the distal end 849a is free-floating or otherwise unconnected to the body portion of adjustable spring plate 846. Varying the position of the ball bearing 848 between the distal end 849a and the proximal end 849b of arm 847 varies the lever or moment arm, which varies the force required to deflect the ball bearing 848 out of one of the notches 843 of knob 842. For example, the lever/moment arm is increased as the ball bearing 848 is moved toward the distal end 849a, which increases the bending moment that is induced in the arm 847 by a force applied to the ball bearing 848. The increased bending moment allows the ball bearing 848 to more easily deflect out of one of the notches 843 in response to an applied force. In contrast, the lever/moment arm is decreased as the ball bearing 848 is moved toward the proximal end 849b, which decreases the bending moment that is induced in the arm 847 by a force applied to the ball bearing 848. The decreased bending moment requires an increased force to be applied to the ball bearing 848 to deflect the ball bearing 848 out of one of the notches 843. Stated differently, the arm 847 flexes more as the ball bearing 848 is moved closer to the distal end 849a, which allows the ball bearing 848 to more easily deflect out of one of the notches 843 in response to an applied force.

The arms 847 of adjustable spring plate 846 allows the ball bearings 848 to deflect radially inward when a predetermined input torque and/or lace tension threshold is achieved or exceeded, which allows the knob 842 to slip relative to disc 845. In this manner, adjustment of the adjustable spring plate 846, and thus the position of the ball bearings 848 relative to arm 847, varies the slippage of the knob 842 relative to disc 845. In some embodiments, when the ball bearings 848 are positioned at the proximal end 849b of the arms 847, inward deflection of the ball bearings 848 may be prevented thereby preventing slippage of the knob 842 relative to disc 845. In this manner, the slippage of the closure device 840 may be varied between essentially no slippage and slippage at a relatively low input torques and/or lace tension thresholds as desired.

In some embodiments, a top portion of the adjustable spring plate 846 may be accessible via an aperture of knob 842 to allow a user to rotate the adjustable spring plate 846 relative to knob 842 and disc 845 and thereby adjust the input torque and/or lace tensioning limit capabilities of closure device 840.

Figure 8T:
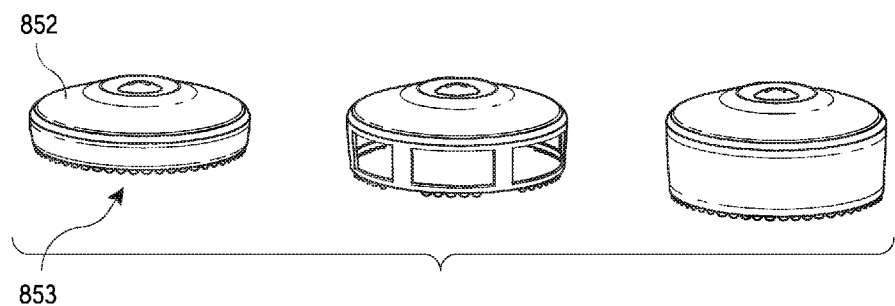
Figure 8U:
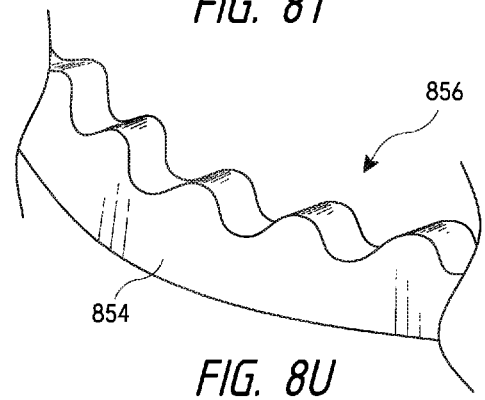

Referring now to FIGS. 8S-V, illustrated is another embodiment of a closure device 850 that includes a clutching mechanism. Specifically, a knob 852 of closure device 850 includes a plurality of protrusions 853 that extend axially downward from a bottom edge of knob 852. The protrusions 853 are configured to be positioned within notches 856 of a tension limiting component 854 that is assembled axially below and directly adjacent knob 852. The protrusions 853 drive tension limiting component 854 as knob 852 is rotated by a user. Tension limiting component 852 in turn drives the other internal components of the closure device 850, such as the spool (not numbered), a pawl disc (not numbered), lace (not shown), and the like. Similar to the other embodiments described herein, when the input torque and/or lace tension threshold is achieved or exceeded, the protrusions 853 of knob 852 will slip from the notches 856 of tension limiting component 854 to prevent further tensioning of the lace. In some embodiments, a screw 858 or other fastening mechanism may be axially displaceable to adjust a frictional engagement or force between the protrusions 853 and notches 856 and thereby vary the slippage of the knob 852 relative to tension limiting component 854. A spring 857 may be positioned internally between the knob 852 and tension limiting component 854. The spring 857 may be compressed as screw 856 is axially adjusted to vary the frictional force/engagement of the protrusions 853 and notches 856. The protrusions 853 and/or notches 856 may have a wavelike pattern, sawlike pattern, triangular pattern, and the like as desired. As shown in FIG. 8T, in some embodiments the knob 852 may include "windows" or cut out portions that are positioned axially above the protrusions 853. The windows may allow the protrusions 853 to more easily deflect axially upward and out of the notches 856 of tension limiting component 854.

Figure 8X:
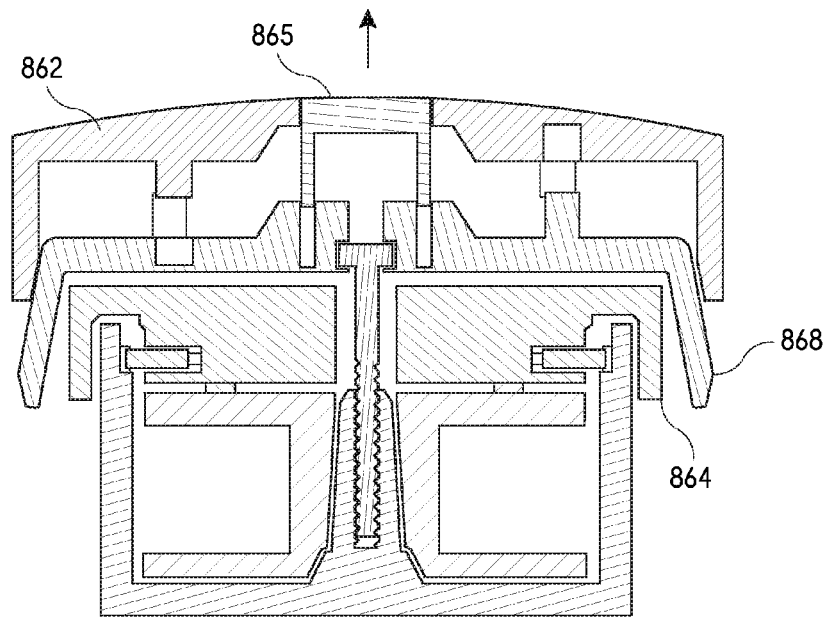
Figure 8Y:
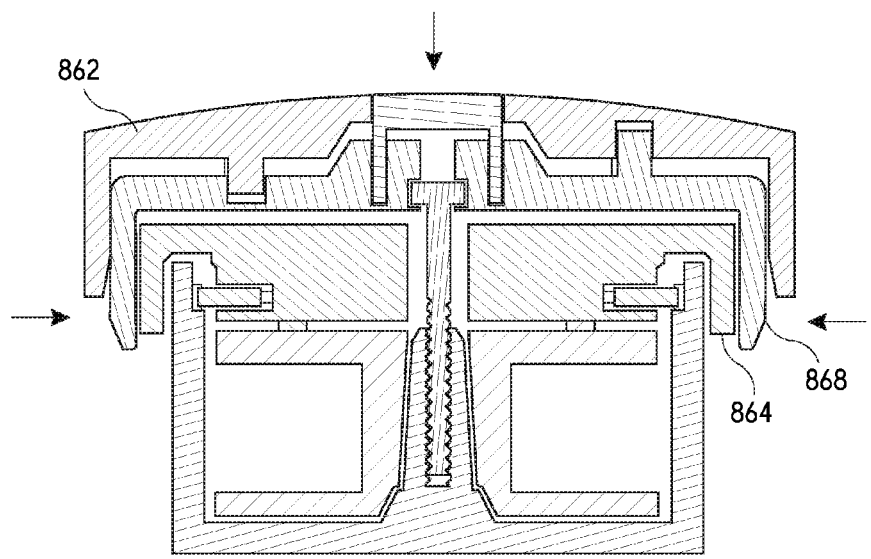

FIGS. 8W-Y illustrate another embodiment of the closure device 860 that includes a clutching mechanism. Specifically, closure device 860 includes an outer knob 862 that is axially adjustable relative to an inner knob 868 in order to vary a frictional engagement or force exerted between the inner knob 868 and a tension limiting component 864. Tension limiting component 864 includes a plurality of notches 863 that are positioned circumferentially around an outer edge of tension limiting component 864. The inner knob 868 includes inwardly directed protrusions (not shown) or other components that fit within the notches 863 of tension limiting component 864.

As shown in FIGS. 8X-Y, as the outer knob 862 is adjusted axially downward relative to inner knob 868, the protrusions or other components of inner knob 868 are pressed more firmly within the notches 863 of tension limiting component 864. This increases the frictional engagement or force between the inner knob 868 and tension limiting component 864, and thus increases an input torque and/or lace tension threshold that is required to achieve slippage between these two components. Likewise, as the outer knob 862 is adjusted axially upward relative to inner knob 868, the protrusions or other components of inner knob 868 are pressed less firmly within notches 863 of tension limiting component 864, which allows the inner knob 868 to more easily slip relative to tension limiting component 864. In some embodiments, axial adjustment of the outer knob 862 relative to the inner knob 868 may be achieved via a threaded shaft 865 or other component. A user may rotate the threaded shaft 865, such as via a screwdriver or other device, to axially adjust the outer knob 862 relative to the inner knob 868 and thereby vary the input torque and/or lace tension limiting capabilities of closure device 860.

Figure 8Z:
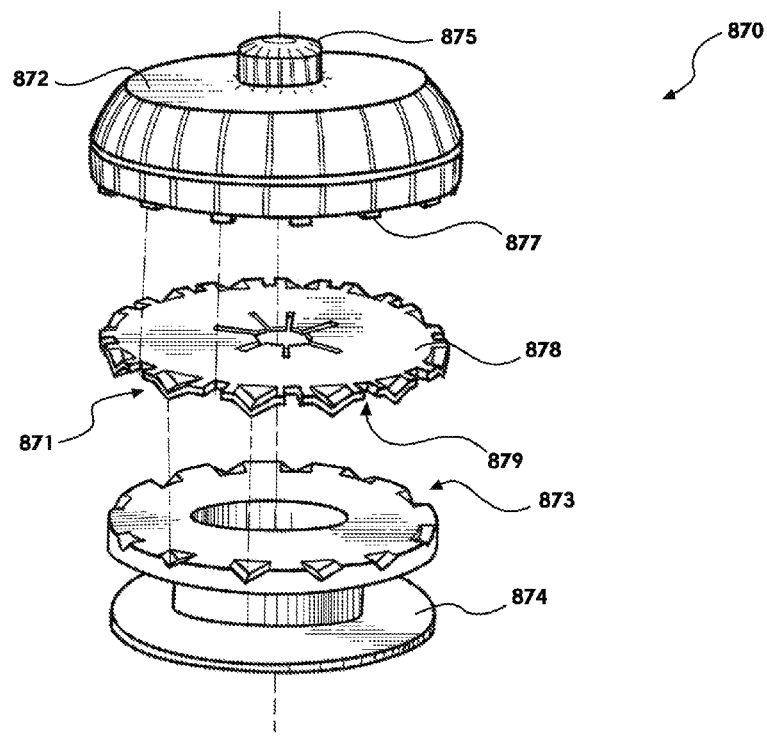
Figure 8A:
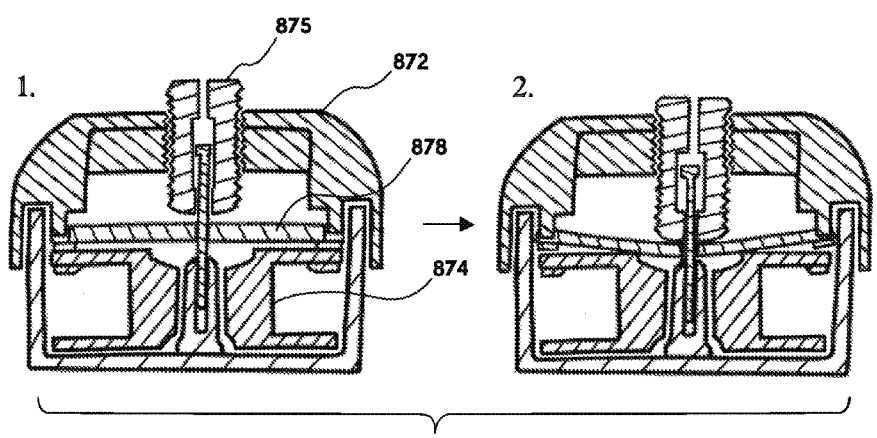
Figure 8B:
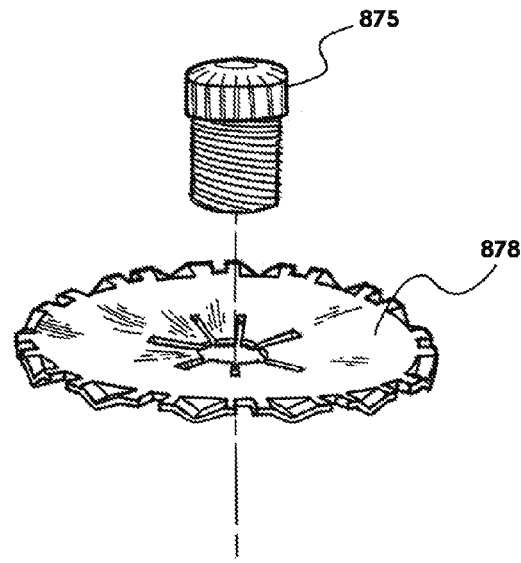
Figure 8C:
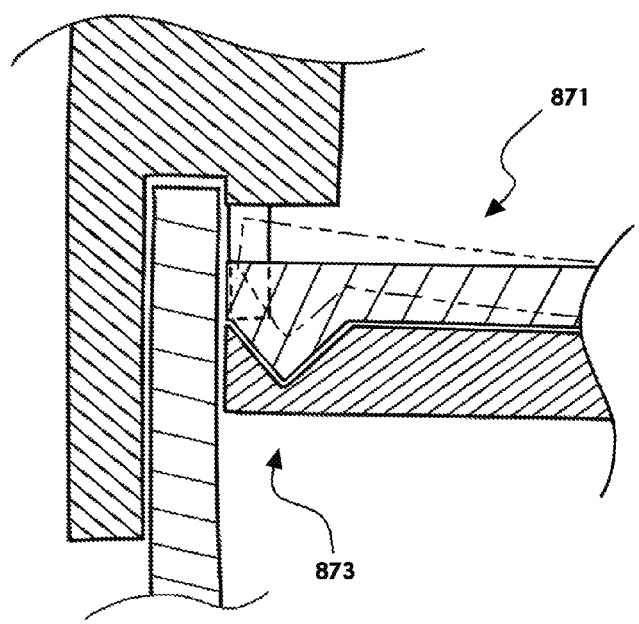
Figure 8D:
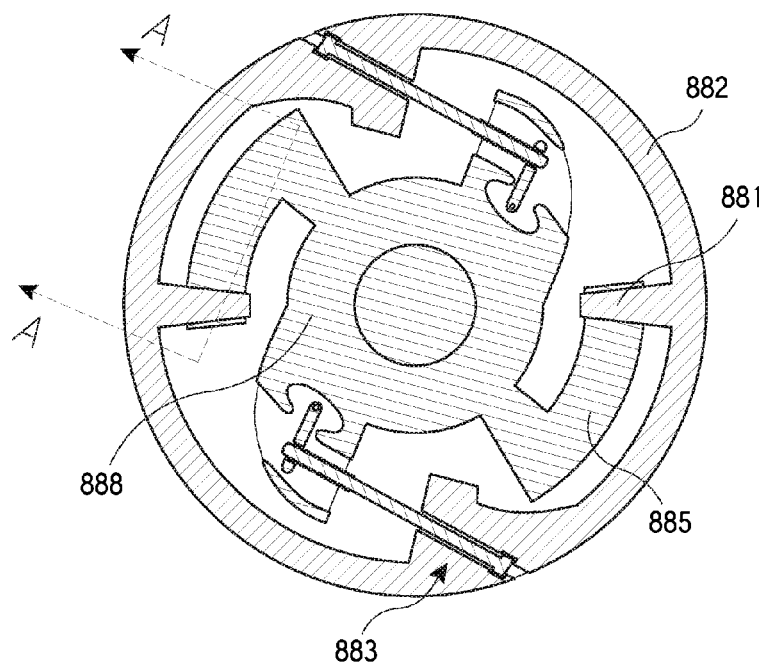
Figure 8E:
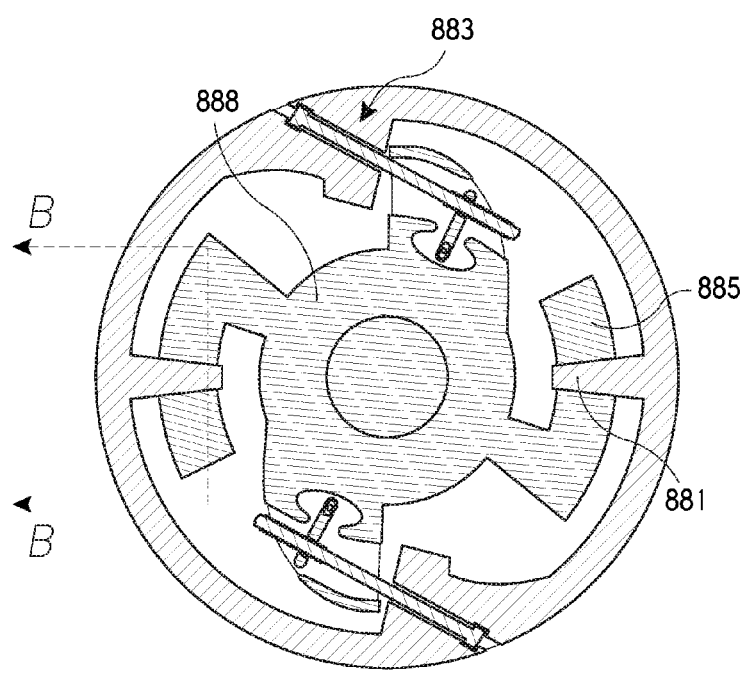
Figure 8F:
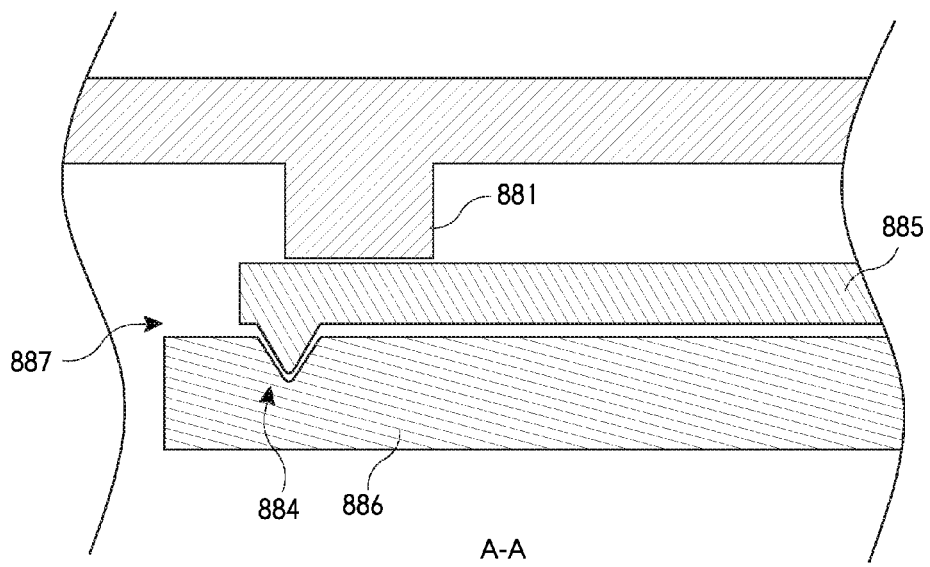
Figure 8G:
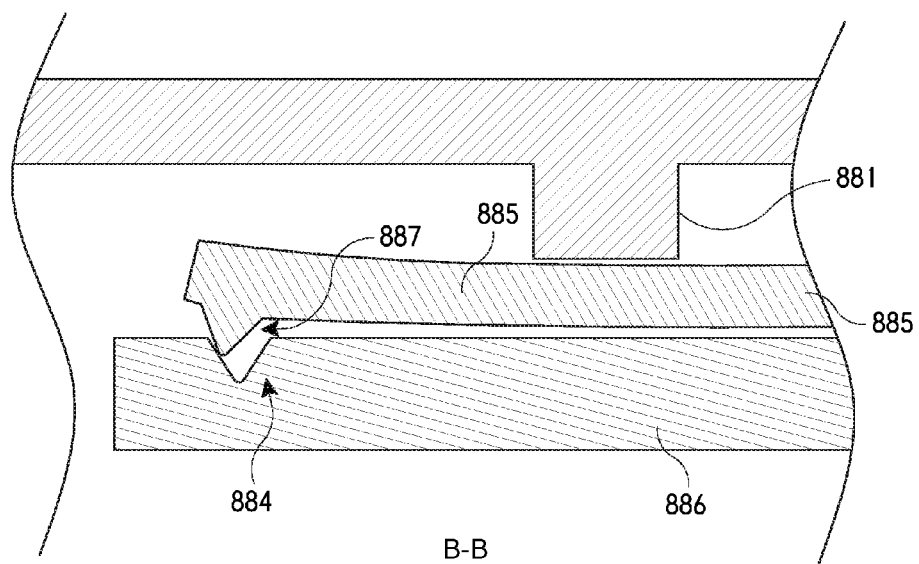
Figure 8H:
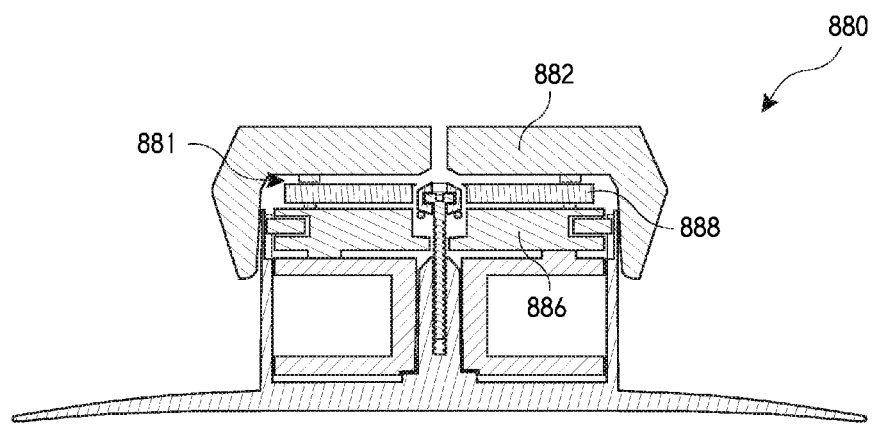
Figure 8I:
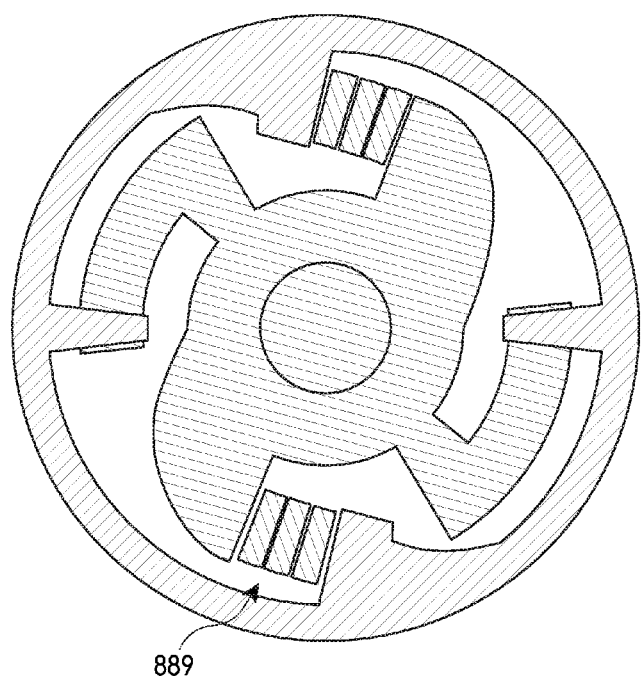

Referring to FIGS. 8Z-CC, illustrated is another embodiment of a closure device that may be used to limit the amount of tension applied to a lace. Closure device 870 includes a clutch plate 878 that is positioned between a knob 872 and a spool 874. Spool 874 includes a plurality of notches 873 within which corresponding teeth 871 of clutch plate 878 are positioned. Knob 872 includes a plurality of drive components 877 that are insertable within corresponding keyed portions 879 of clutch plate 878 and that function to drive the clutch plate 878 as knob 872 is rotated by a user. As the knob 872 and clutch plate 878 are rotated, teeth 871 drive spool 874 via notches 873. When a predetermined input torque and/or lace tension threshold is achieved or exceeded, the teeth 871 deflect axially upward and slip out of the notches 873 causing the clutch plate 878 and knob 872 to slip relative to spool 874.

A screw 875 or other component is threadingly coupled with knob 872 so as to be axially adjustable downward onto clutch plate 878. Threading screw 875 axially downward onto clutch plate 878 causes clutch plate 878 to bow which deflects teeth 871 partially out of notches 873 of spool 874. Deflection of the teeth 871 out of notches 873 varies the slippage of the clutch plate 878 and knob 872 relative to spool 874 by allowing a lesser input torque and/or lace tension threshold to be achieved before the teeth 871 will deflect axially upward and slip out of notches 873. As can be readily understood by one skilled in the art, the more that clutch plate 878 is caused to bow via screw 875, the more slippage will be achieved between clutch plate 878 and knob 872 relative to spool 875 at a lower input torque and/or lace tension threshold. In some embodiments, clutch plate 878 may include a central aperture and or radially extending slots to facilitate bowing of the clutch plate 878 as screw 875 is threaded axially downward onto clutch plate 878.

Referring to FIGS. 8DD-II, illustrated is another embodiment of a closure device 880 that may be used to limit the amount of tension applied to a lace. Closure device 880 includes a knob 882 having one or more radially inwardly extending flanges 881 that are positioned over arms 885 of a clutch plate 888. The position of the flanges 881 relative to the arms 885 may be adjusted to vary an input torque and/or lace tension threshold at which the closure device 880 will slip. Specifically as shown in cross section A-A of FIG. 8FF and cross section B-B of FIG. 8GG, the arms 885 include tab portions 887 that are insertable within notches 884 of a tension limiting component 886 that is in turn coupled with a spool (not numbered) or integrally formed therewith. As described herein, the tab portions 887 are configured to drive rotation of the tension limiting component 886 and spool, and to deflect out of the notches 884 in a detent-like manner when a predetermined input torque and/or lace tension threshold is achieved or exceeded to prevent further tensioning of the lace.

As shown in the cross-sections A-A and B-B, the flanges 881 are slidable along the arms 885 between a proximal end, in which the flanges 881 are positioned away from the tab portions 887, and a distal end, in which the flanges 881 are positioned adjacent or axially above the tab portions 887. When the flanges 881 are positioned near the proximal end, the flex of the arms 885 is increased due to an increase moment arm and bending moment, which allows the tab portions 887 to more easily deflect out of the notches 884 of tension limiting component 886. In contrast, when the flanges 881 are positioned near the distal end, the flex of the arms 885 is greatly decreased due to a decreased moment arm and bending moment, which requires an increased input torque and/or lace tension force to cause the tab portions 887 to deflect out of the notches 884. In some embodiments, the flanges 881 may be positioned axially above the tab portions 887 to prevent the tab portions 887 from deflecting out of the notches 884. In this manner, slippage of the closure device 880 may be essentially prevented.

In some embodiments, movement of the flanges 881 along the arms 885 may be provided via an tension varying mechanism 883, such as a screw that is threadingly coupled with the clutch plate 888. The tension varying mechanism 883 may be accessible by a user and/or physician as desired. The tension varying mechanism 883 allows the slippage of the closure device 880 to be varied between essentially no slippage and slippage at relatively low input torques and/or lace tension thresholds as desired. As shown in FIG. 8II, in some embodiments spacers 889 may be positioned between the clutch plate 888 and the knob 882 to position and maintain the flanges 881 at a desired position relative to arms 885. In some embodiments, the spacers 889 and/or tension varying mechanism 883 may drive rotation of the clutch plate 888 as the knob 882 is rotated by a user.

Figure 9A:
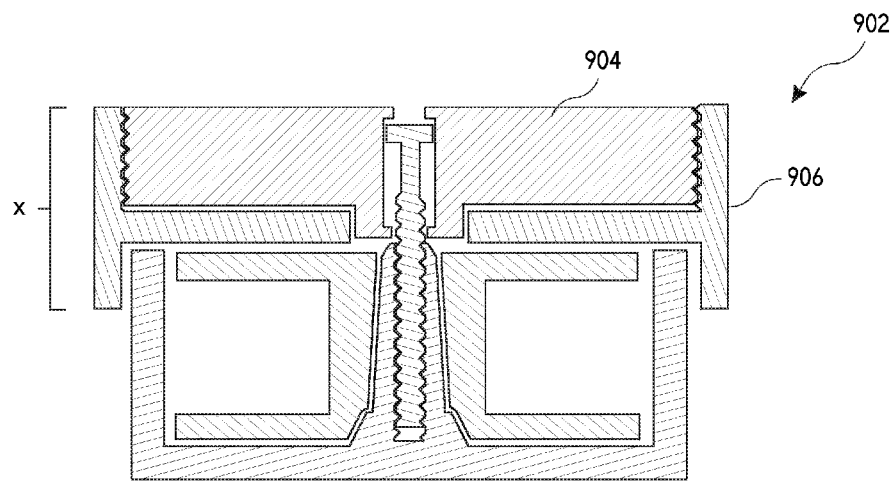
Figure 9B:
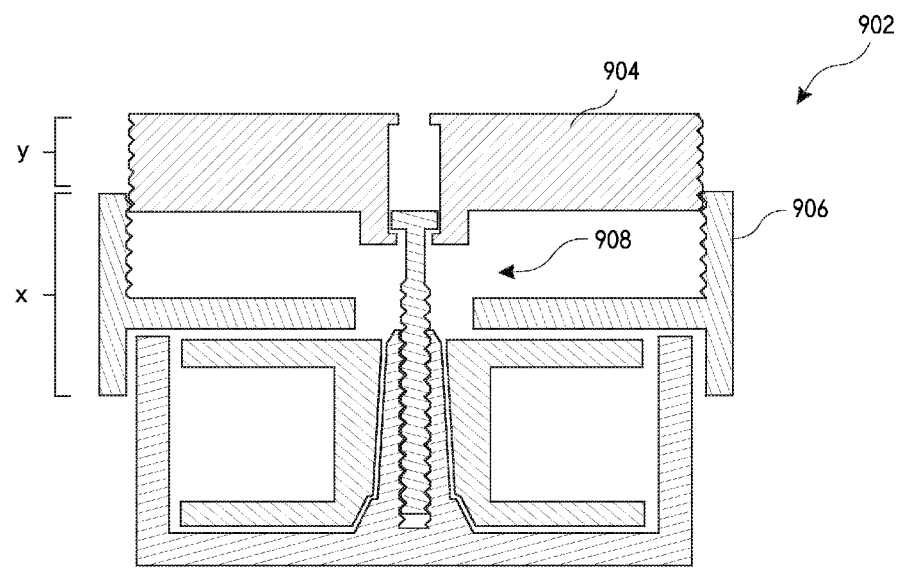
Figure 9C:
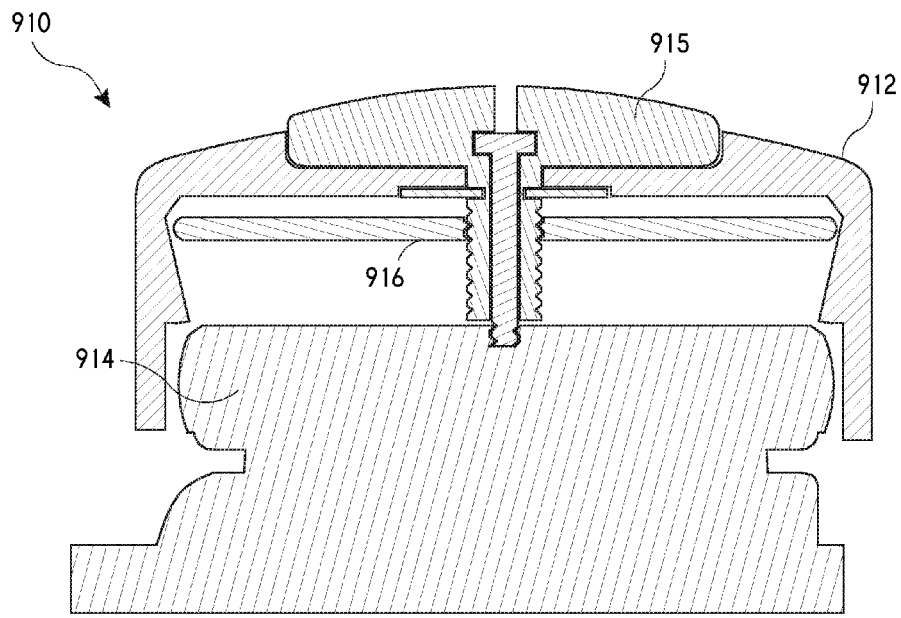
Figure 9D:
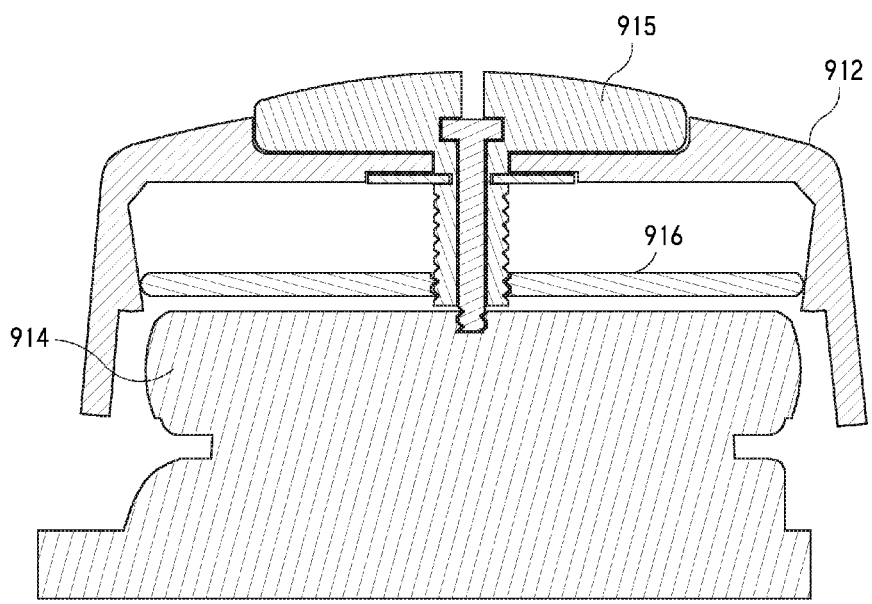
Figure 9E:
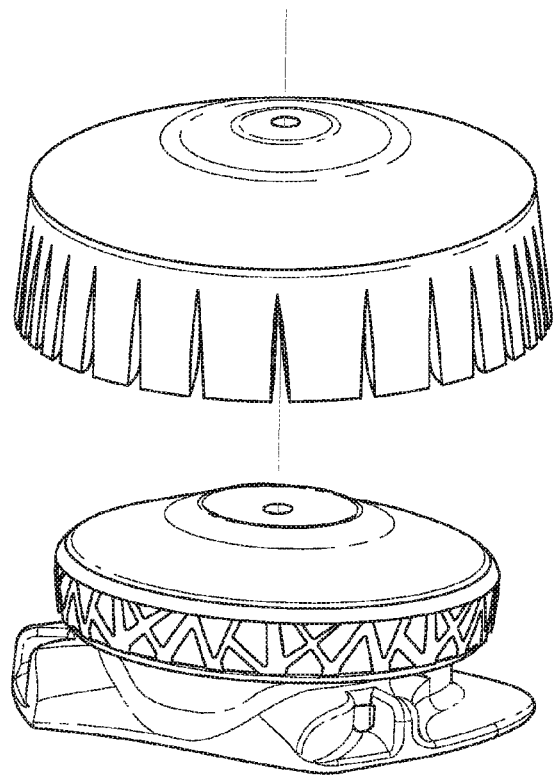
Figure 9F:
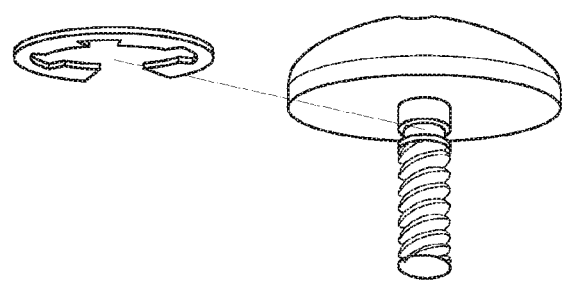

Referring now to FIGS. 9A-I, illustrated are embodiments of limiting an amount of tension that may be applied by affecting a user's grip on a knob portion of the closure device. For example, FIGS. 9A-B illustrate an embodiment of the closure device 900 where a knob component 902 includes an inner knob 904 and an outer knob 906. The inner knob 904 is axially adjustable relative to outer knob 906 so as to increase a grip surface of the knob component 902. In one embodiment, the inner knob 904 may be threadingly coupled with the outer knob 906 such that the inner knob 904 may be threaded axially upward or downward with respect outer knob 906. When the inner knob 904 is threaded fully axially downward, the grip surface of knob component 902 may have a height of approximately X as shown in FIG. 9A. In contrast, when the inner knob 904 is threaded fully axially upward, the grip surface of knob component 902 may have a height of approximately X+Y as shown in FIG. 9B. Because the overall grip of the knob component 902 is greater when the inner knob 904 is axially extended from outer knob 906, a user may more easily grip knob component 902 and rotate the knob component 902 to tension the closure device's lace. Similarly, when the inner knob 904 is retracted within the outer knob 906, a user's grip on knob component 902 is negatively affected making it more difficult for the user to grip knob component 902 and tension the closure device's lace. In some embodiments, the inner knob 904 may be axially adjustable along a shaft 908 that is centrally positioned within closure device 900.

Figure 9G:
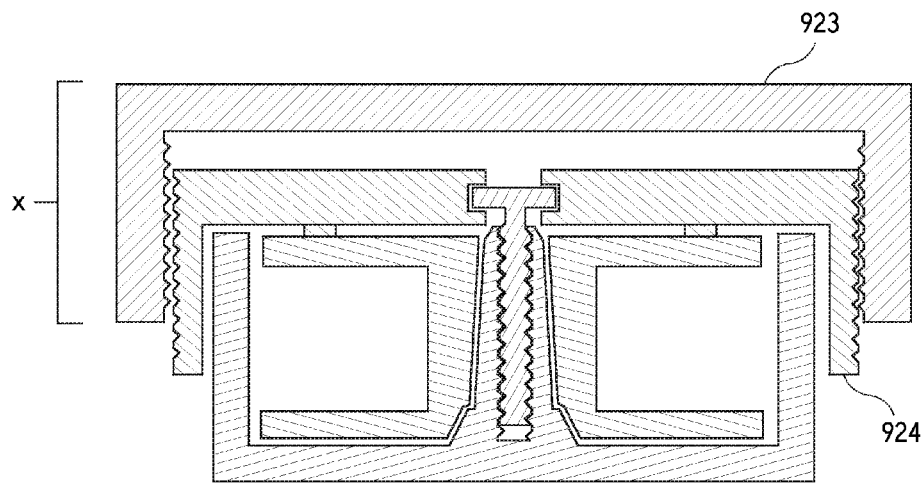
Figure 9H:
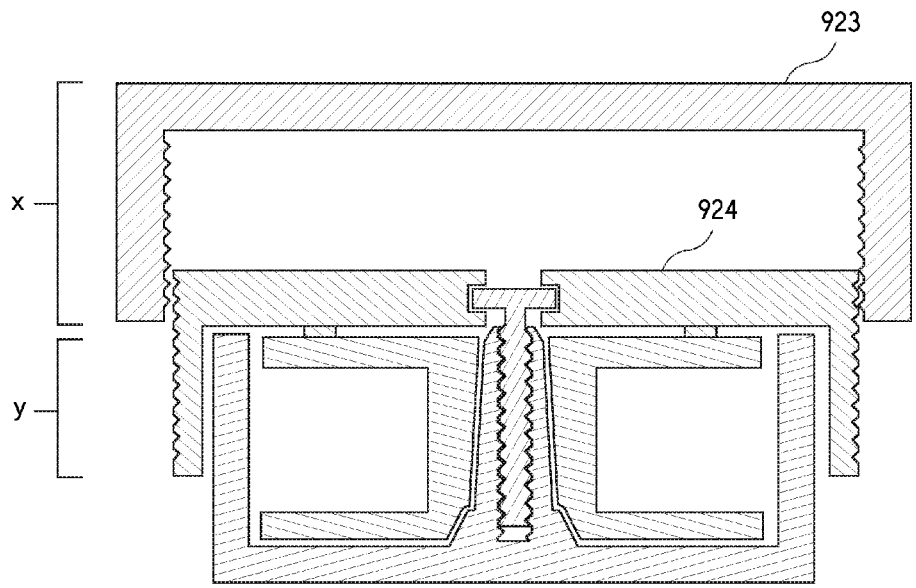
Figure 91:
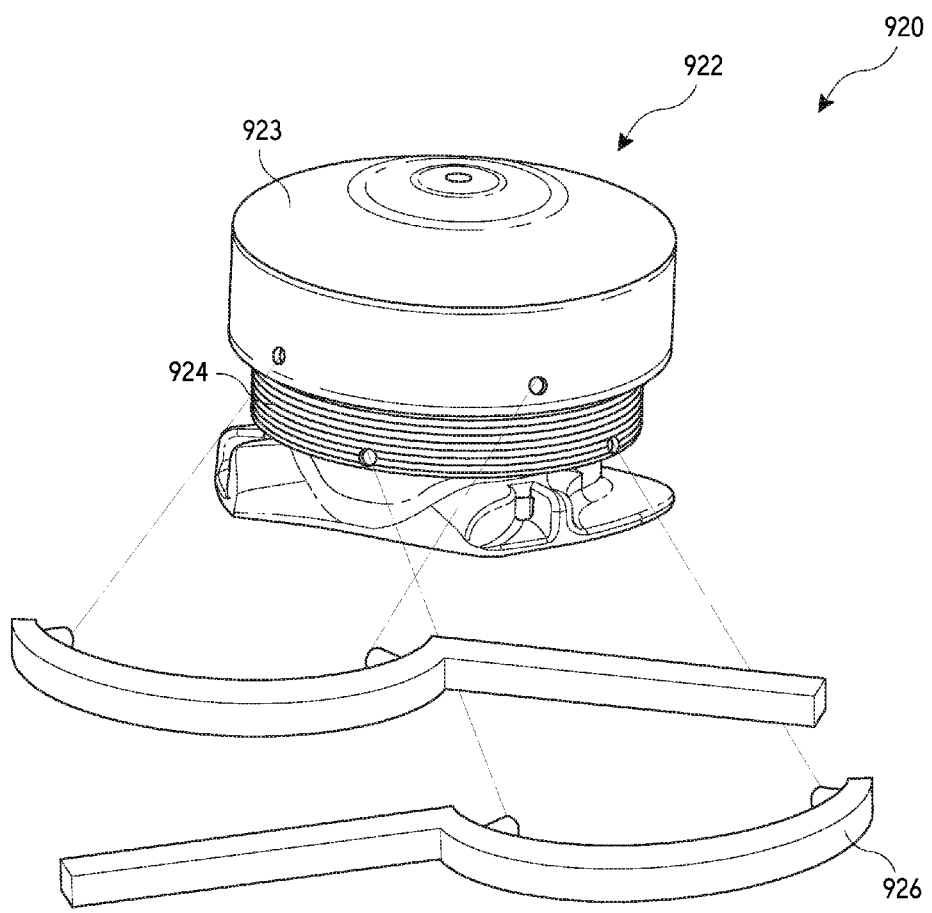

Referring now to FIGS. 9C-F, illustrated is another embodiment of a closure device 910 in which a user's ability to grip a knob 914 may be varied. Specifically, an outer cap 912 is positioned atop knob 914. A user presses radially inward on a cover portion of outer cap 912 which squeezes knob 914 and allows the user to rotate knob 914. Outer cap 912 includes an adjustment mechanism 915, such as a threaded screw, that may be adjusted (e.g., rotated) to axially adjust a disc 916 positioned within outer cap 912. Axially adjusting disc 916 within outer cap 912 varies the user's ability to squeeze the cover portion of outer cap 912 about knob 914. For example, when disc 916 is positioned adjacent an inner surface of outer cap 912, the cover portion of outer cap 912 is flexible and may be easily squeezed by a user against the outer surface of knob 914. When disc 916 is axially adjusted downward so that disc 916 is adjacent a top surface of knob 914, the cover portion of outer cap 912 is relatively rigid thereby making it more difficult for a user to squeeze the cover portion of outer cap 912 against knob 914. In this manner the ability of a user to grip knob 914 may be varied which affects the user's ability to tension a lace via closure device 910 and/or allows outer cap 912 to slip relative to knob 914, Referring now to FIGS. 9G-I, illustrated is another embodiment of the closure device 920 the may be used to affect a user's ability to grasp a knob component 922 of the closure device 920. Similar to the closure device 900 described previously, the knob component 922 of closure device 920 includes an outer knob 923 and an inner knob 924. Outer knob 923 is rotatable relative to enter knob 924 so as to very a grip surface of the knob component 922. For example, when outer knob 923 is adjusted fully axially downward relative to inner knob 924, a grip surface of knob component 922 may have a height of approximately X as shown in FIG. 9G. When outer knob 923 is adjusted fully axially upward relative to inner knob 924, a grip surface of knob component 922 may have a height of approximately X+Y as shown in FIG. 9H. As previously described, the increased grip surface of knob component 922 may make it considerably easier for a user to grip the knob component 922 and tension the closure device's lace. As shown in FIG. 9I, in some embodiments a tool 926 may be used to hold inner knob 924 stationary relative to outer knob 923 in order to allow the outer knob 923 to be rotated relative to inner knob 924. In other embodiments, tool 926 may be used to provide additional torque that may be required to rotate outer knob 923 relative to inner knob 924. In some embodiments, a pair of tools similar to tool 926 may be used to hold one of the knobs stationary while the other knob is rotated in order to axially adjust the outer knob 923 relative to the inner knob 924.

Referring now to FIG. 10A, illustrated is an embodiment of a closure device 1000 that includes a clutching mechanism 1006. Clutching mechanism 1006 functions via friction between a bottom surface of knob 1002 and a top surface of a tension limiting member 1004. Specifically, the bottom surface of knob 1002 and the top surface of tension limiting member 1004 are angled and these angled portions of the knob 1002 and tension limiting member 1004 engage to effect tensioning of the lace via friction. Closure device 1000 also includes a screw 1008 or other fastening component that is coupled with knob 1002. Positioned between a bottom surface of screw 1008 and within a recess of knob 1002 is a spring washer 1007. Screw 1008 may be adjusted axially relative to knob 1002 so as to compress spring washer 1007. Screw 1008 is also connected to tension limiting member 1004 such that compression of the spring washer 1007 causes increased engagement or contact, and thus friction, between the angled portions of the knob 1002 and tension limiting member 1004. In this manner, the friction force between the knob 1002 and tension limiting member 1004 may be increased or decreased as desired to affect tensioning of the closure device 1000's lace.

Further, as shown in FIG. 10A, the angle of the knob 1002 and the tension limiting member 1004 may be modified as desired to increase or decrease the friction between the knob 1002 and tension limiting member 1004. For example, increasing the angled portions to have a steeper profile typically increases the friction between the two components while decreasing the angled portions typically decreases the friction between the two components. In operation, the frictional force between the angled portions of the knob 1002 and tension limiting member 1004 drives rotation of the tension limiting member 1004 as the knob 1002 is rotated. The spool 1009 is rotated to wind lace via teeth between the spool 1009 and tension limiting member 1004. When the input torque and/or lace tension reaches a predetermined threshold, the frictional force between the angled portions of the knob 1002 and tension limiting member 1004 is insufficient to cause further rotation of the spool 1009, which causes the tension limiting member 1004 to slip upon subsequent rotation of the knob 1002. In this manner, the lace may be tensioned to a predetermined threshold before the lace is no longer tensionable via rotation of the knob 1002.

Figure 10B:
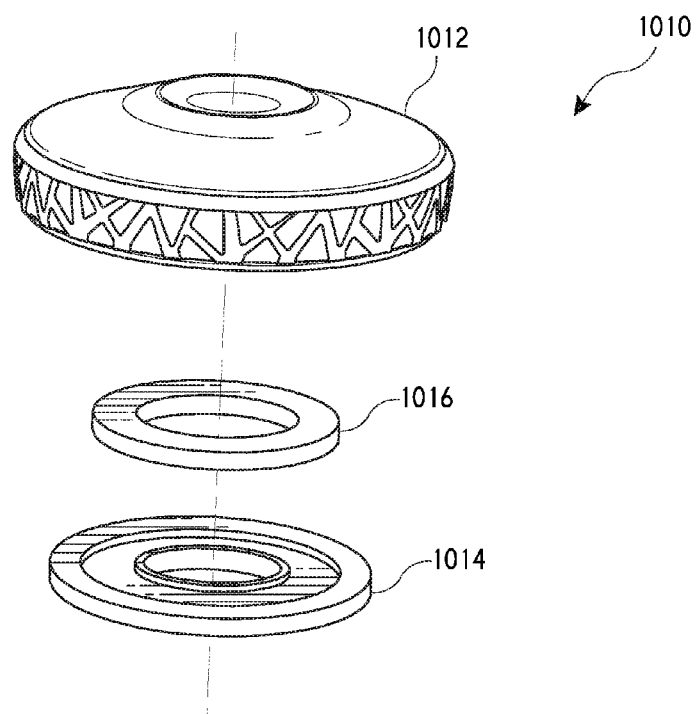
Figure 10C:
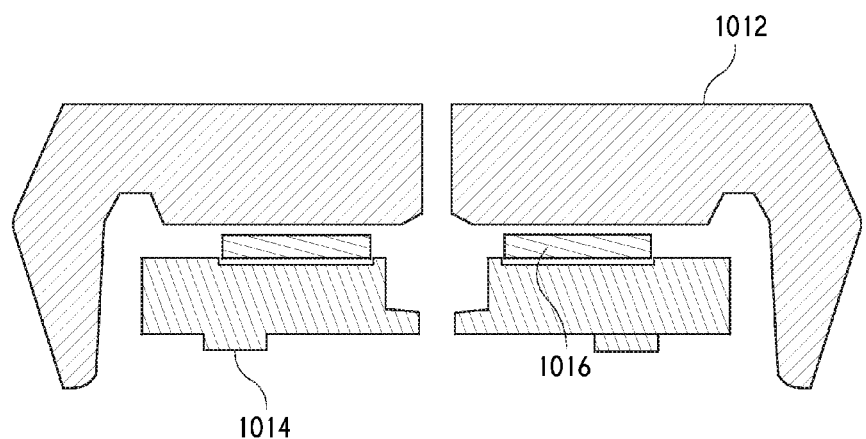

Referring now to FIGS. 10B-D, illustrated is an embodiment of a closure device 1010 that includes another embodiment of a friction-based clutching system. Specifically, closure device 1010 includes a knob 1012 and a tension limiting component 1014. A friction disc 1016 is positioned between the knob 1012 and the tension limiting component 1014. The tension limiting component 1014 includes a groove or channel within which the disc 1016 is positioned. Frictional contact between the disc 1016, tension limiting component 1014, and knob 1012 drives rotation of these components as the knob 1012 is rotated by a user. Closure device 1010 may also include an adjustable spring (not shown) that may be adjusted to increase or decrease the frictional engagement or contact between the knob 1012, disc 1016, and or tension limiting component 1014, and thereby increase or decrease a slippage threshold of these components. In some embodiments, disc 1016 may be integrally formed with knob 1012 so that the closure device 1010 only includes two components (i.e., knob 1012 and tension limiting component 1014).

As described previously, the frictional engagement/force between the knob 1012, disc 1016, and/or tension limiting component 1014 allows tensioning of the closure device 1010's lace until a predetermined input torque and/or lace tension threshold is achieved. After the predetermined input torque and/or lace tension threshold is achieved, one or more of these components (i.e. knob 1012, disc 1016, and/or tension limiting component 1014) will slip so that further tensioning of the lace is not possible or is greatly reduced.

FIG. 10D illustrates other embodiments of disc 1016. In sonic embodiments, the frictional disc may be relatively flat 1016a, conically shaped 1016b, have multiple conical sections 1016c, and/or have any other desired configuration so as to provide a desired amount of frictional engagement/contact between the knob 1012, disc 1016, and/or tension limiting component 1014. Likewise, the material of the disc 1016 may be varied (e.g., polymer material, metal material, and the like) to vary the coefficient of friction and thereby provide a desired amount of frictional force. Depending on the activity or other use of the closure device 1010, disc 1016 may be replaced with an appropriate disc having desired frictional properties for a given activity or usage.

Figure 10E:
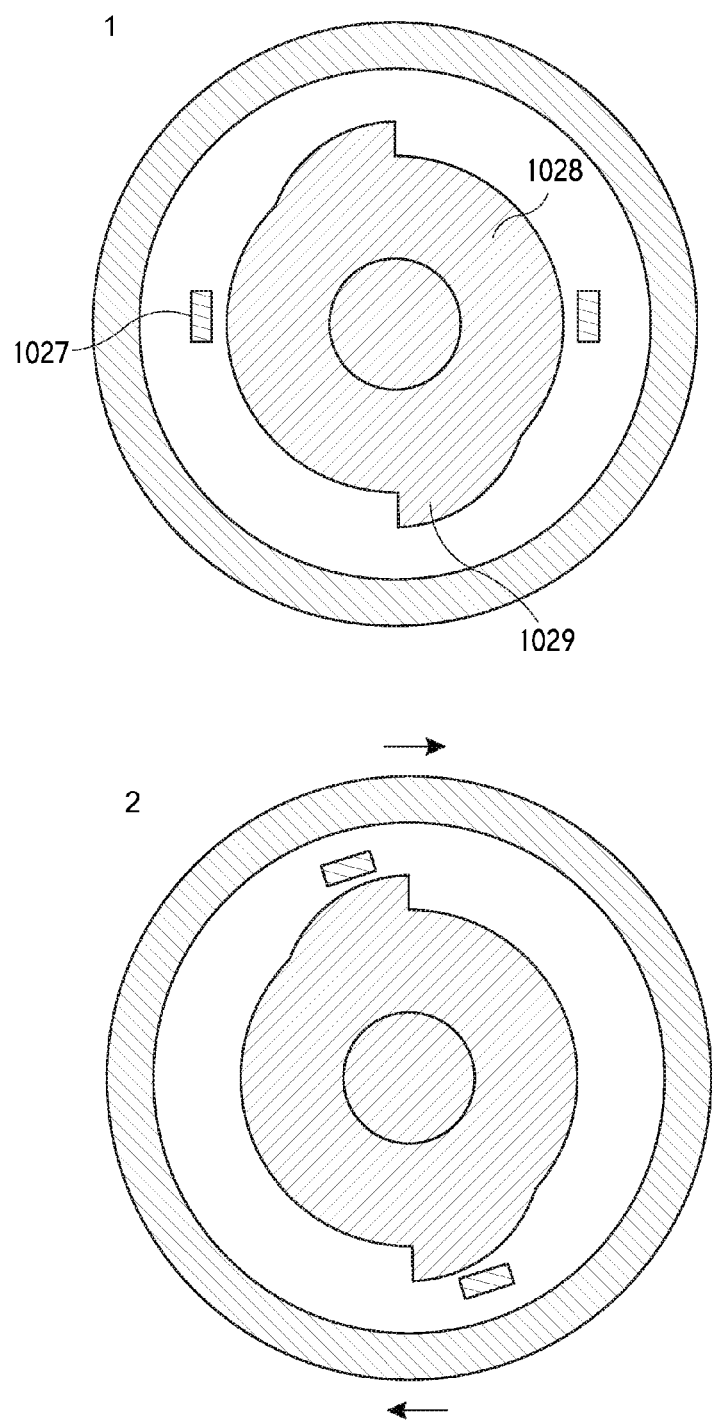
Figure 10F:
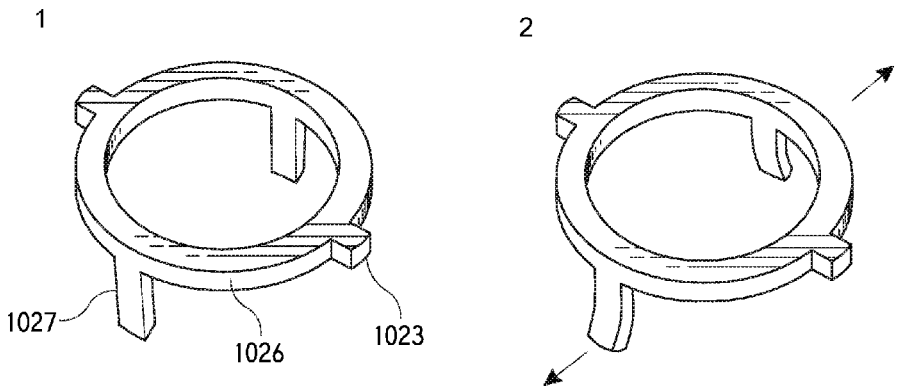
Figure 10G:
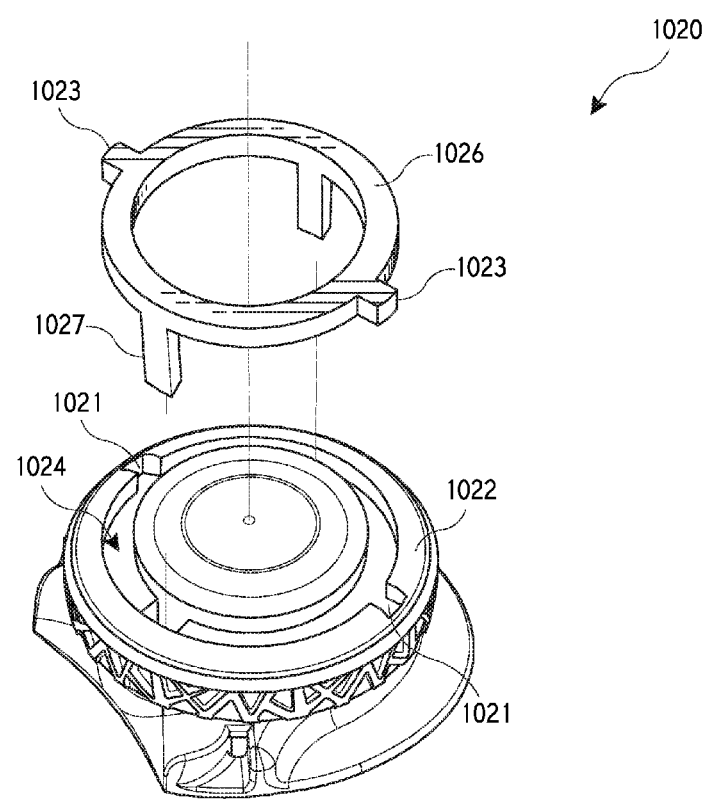

FIGS. 10E-G illustrate another embodiment of a closure device 1020 that includes a friction-based clutching system. Specifically, closure device 1020 includes a knob 1022 having a channel 1024 formed in its top surface. A friction ring 1026 may be placed within the channel 1024 of knob 1022. Closure device 1020 also includes a tension limiting member 1028 that is positioned internally of the knob 1022. The friction ring 1026 includes a pair of axially extending flanges 1027 that contact the tension limiting member 1028 as the knob 1022 is rotated. Knob 1022 is configured to drive rotation of friction ring 1026 as the knob 1022 is rotated by a user. To drive rotation of the friction ring 1026, knob 1022 may include a pair of slots 1021 within which radially extending flanges 1023 of friction ring 1026 are inserted. In some embodiments, tension limiting member 1028 includes a cam surface 1029 that increases the frictional contact between the flanges 1027 and the tension limiting member 1028 as the knob 1022 and friction ring 1026 are rotated relative to tension limiting member 1028.

The frictional engagement/contact between the friction ring 1026 and tension limiting member 1028, and more specifically engagement/contact between the flanges 1027 and cam surface 1029, causes rotation of the tension limiting member 1028 and a spool (not numbered) coupled therewith, which in turn winds lace around the spool. When a predetermined input torque and/or lace tension threshold is achieved or exceeded, the frictional force between the flanges 1027 and the cam surface 1029 is overcome such that the friction ring 1026 and flanges 1027 slip relative to tension limiting member 1028 and cam surface 1029. In this manner, the lace may be tensioned only until a predetermined input torque and/or lace tension is approximately achieved. The friction ring 1026 may be removed from knob 1022 and replaced with a different friction ring in order to achieve more or less frictional resistance as desired. Friction ring 1026 may include any number of flanges 1027, any flange thickness or width, and/or any material to provide a desired amount of friction.

Figure 10H:
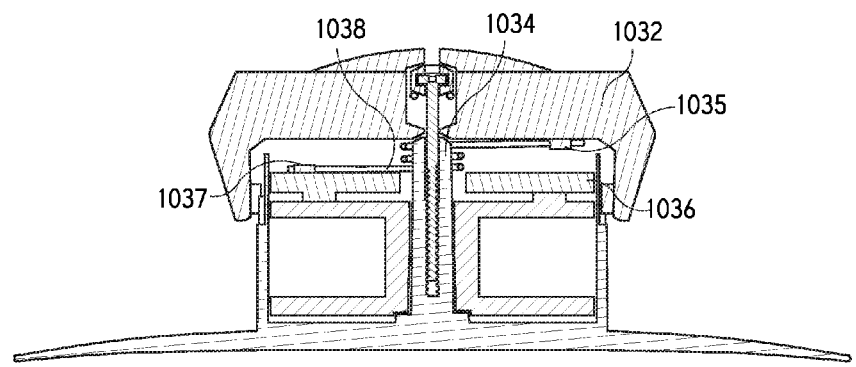
FIGS. 10H-I illustrate an embodiment of a closure device and/or tension limiting mechanism that utilizes a torsion spring to create a friction-based clutching mechanism.
Figure 10I:
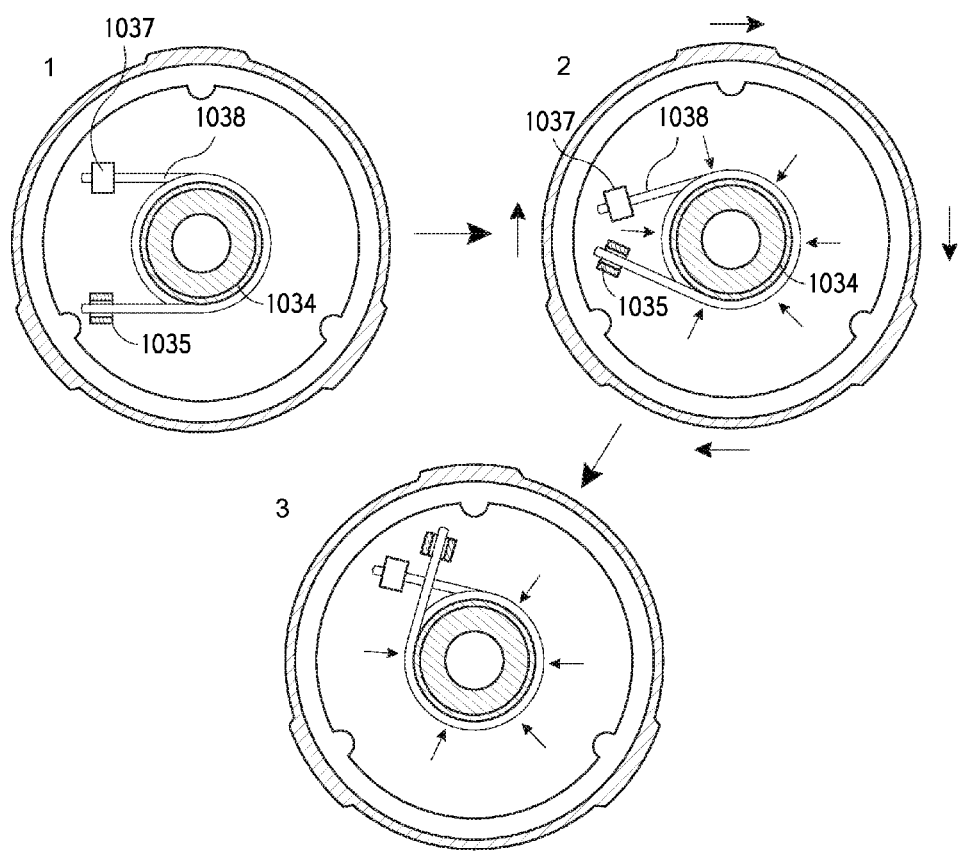
Figure 10J:
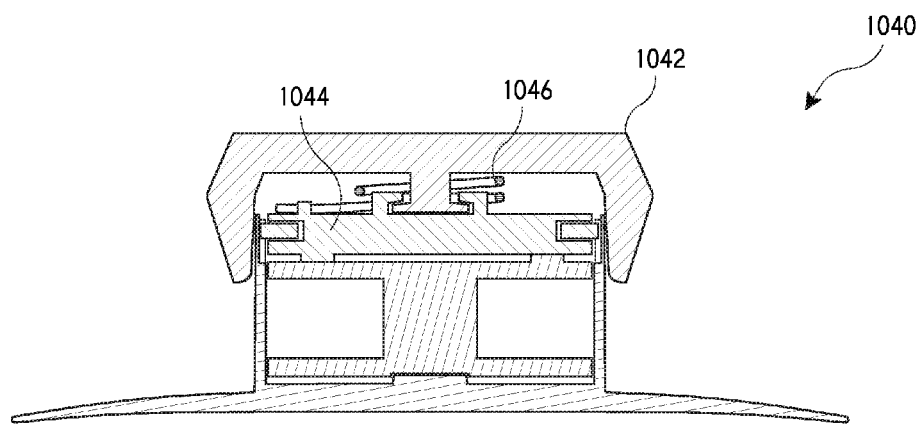
FIGS. 10J-M illustrate an embodiment of a closure device that includes a tension level indicator.
Figure 10K:
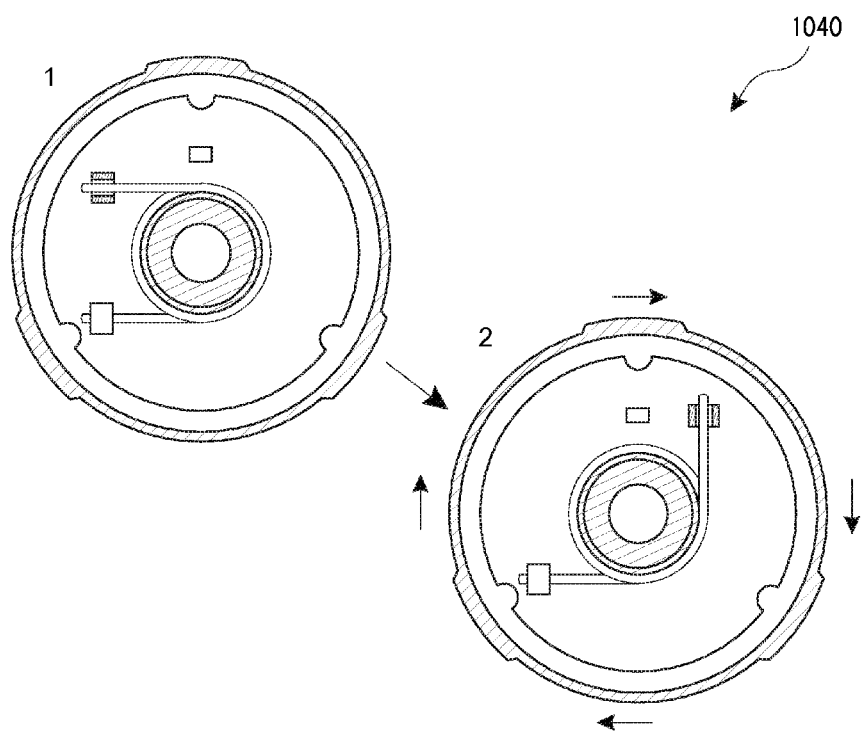
Figure 10L:
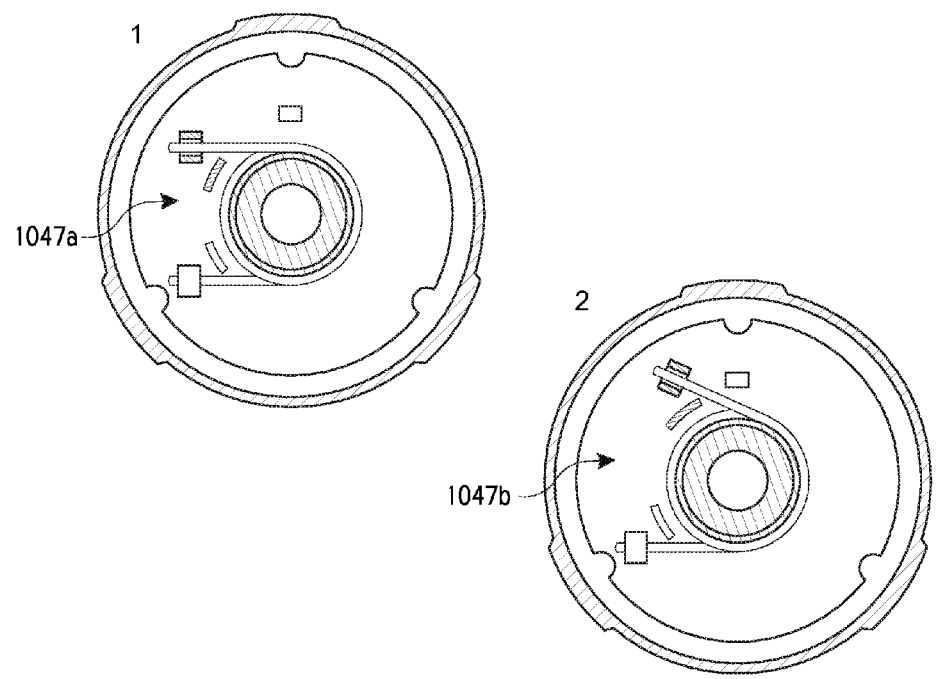
Figure 10M:
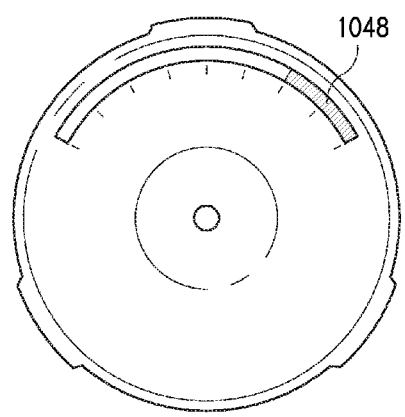

As shown in FIGS. 10H-I, illustrated is another embodiment of a closure device 1030 that uses a friction-based clutching mechanism. Specifically, closure device 1030 includes a knob 1032 and a tension limiting component 1036 that is positioned internally of the knob 1032. A coil spring 1038 is positioned between a bottom surface of the knob 1032 and a top surface of the tension limiting component 1036. The coil spring 1038 is loosely coiled around a post 1034 of spool housing 1033. The bottom surface of the knob 1032 includes a coupling member 1035 that an end of the coil spring 1038 attaches to. Similarly, a top surface of the tension limiting component 1036 also includes a coupling member 1037 that an opposite end of the coil spring 1038 attaches to. As the knob 1032 is rotated, the torque is transferred through coil spring 1038 and to the tensioning limiting component 1036 via coupling members 1035 and 1037. The torque causes the tension limiting component 1036, and a spool (not numbered) coupled therewith, to rotate, which winds lace around the spool. As the tension in the lace increases, the coil spring 1038 begins to constrict about the post 1034. At some point during rotation of the knob 1032, such as when a predetermined amount of input torque and/or lace tension threshold is achieved or exceeded, the coil spring 1038 will constrict about the post 1034 such that further rotation of the tension limiting component 1036 and knob 1032 is prevented. In this manner, the lace may be tensioned only until a predetermined amount of input torque and/or lace tension threshold is achieved.

Referring now to FIGS. 10J-M, illustrated is an embodiment of a closure device 1040 that includes a tension level indicator. Closure device 1040 includes a knob 1042. and a tensioning component 1044 that is similar to the components previously described. A coil spring 1046 is positioned between a bottom surface of the knob 1042 and a top surface of the tensioning component 1044. Coil spring 1046 is different than the coil spring 1038 previously described, in that rotation of the knob 1042 causes the coil spring 1046 to uncoil rather than constrict about a post. As previously described, torque is transferred from knob 1042 to tensioning component 1044 via coil spring 1046. As the input torque and/or lace tension increases, coil spring 1046 will begin to uncoil.

In some embodiments, one end of the coil spring 1046 may be coupled with a visual indicator that is positioned under a tensioning window 1048 of knob 1042. Uncoiling of the coil spring 1046 causes the visual indicator to rotate within the tensioning window 1048, which produces a visual indication of the tension level applied to the lace. In another embodiment, one end of the coil spring 1046 may be coupled with a component that is configured to rotate past a sensor as the coil spring 1046 uncoils. Closure device 1040 may be configured to alert a user when component 1041 rotates past the sensor. The alert may be a visual and/or audio alert as desired, such as an audible alarm or a flashing light that indicates that a predetermined input torque and/or lace tension threshold has been reached. In this manner, a user may recognize when the closure device 1040's lace has been appropriately tensioned.

Figure 11A:
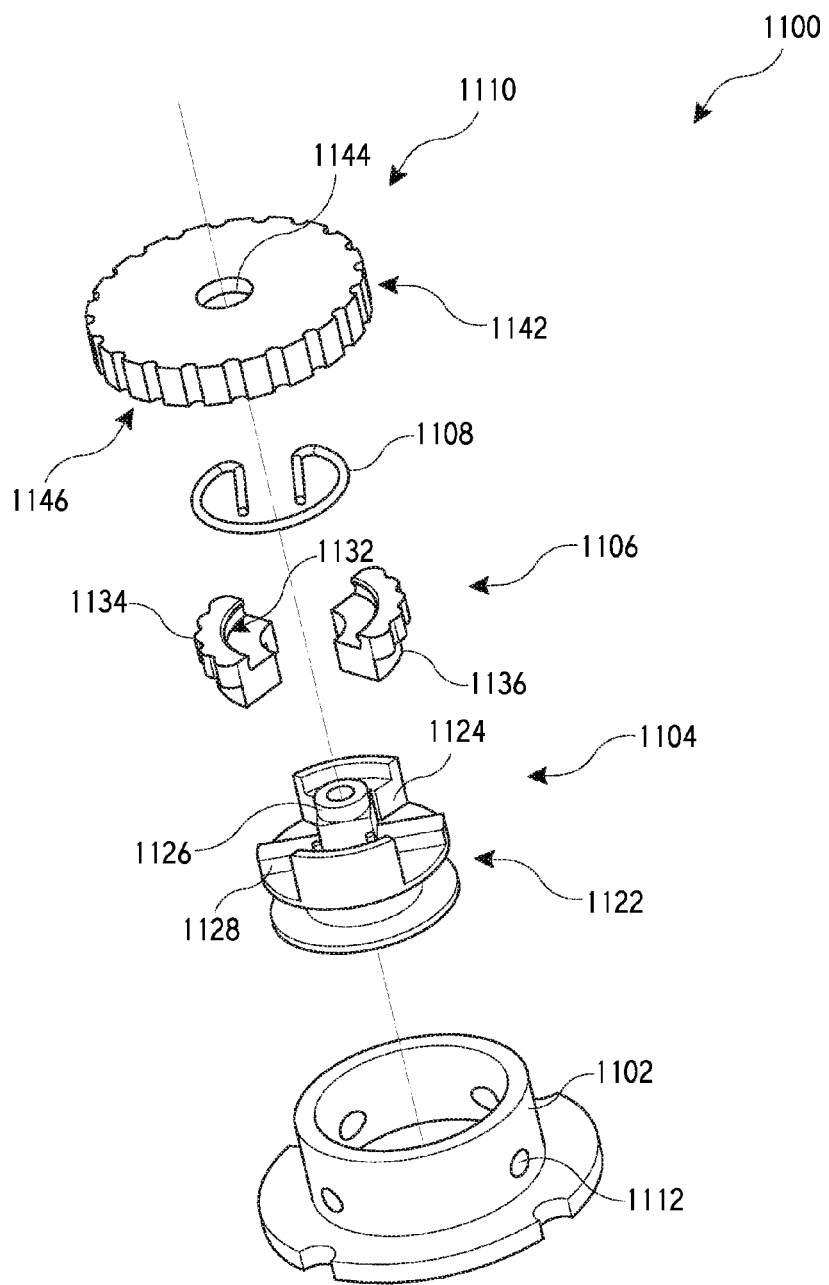
FIGS. 11A-C illustrate another embodiment of a closure device having a tension control mechanism that includes a pair of radially displaceable clutch components.
Figure 11B:
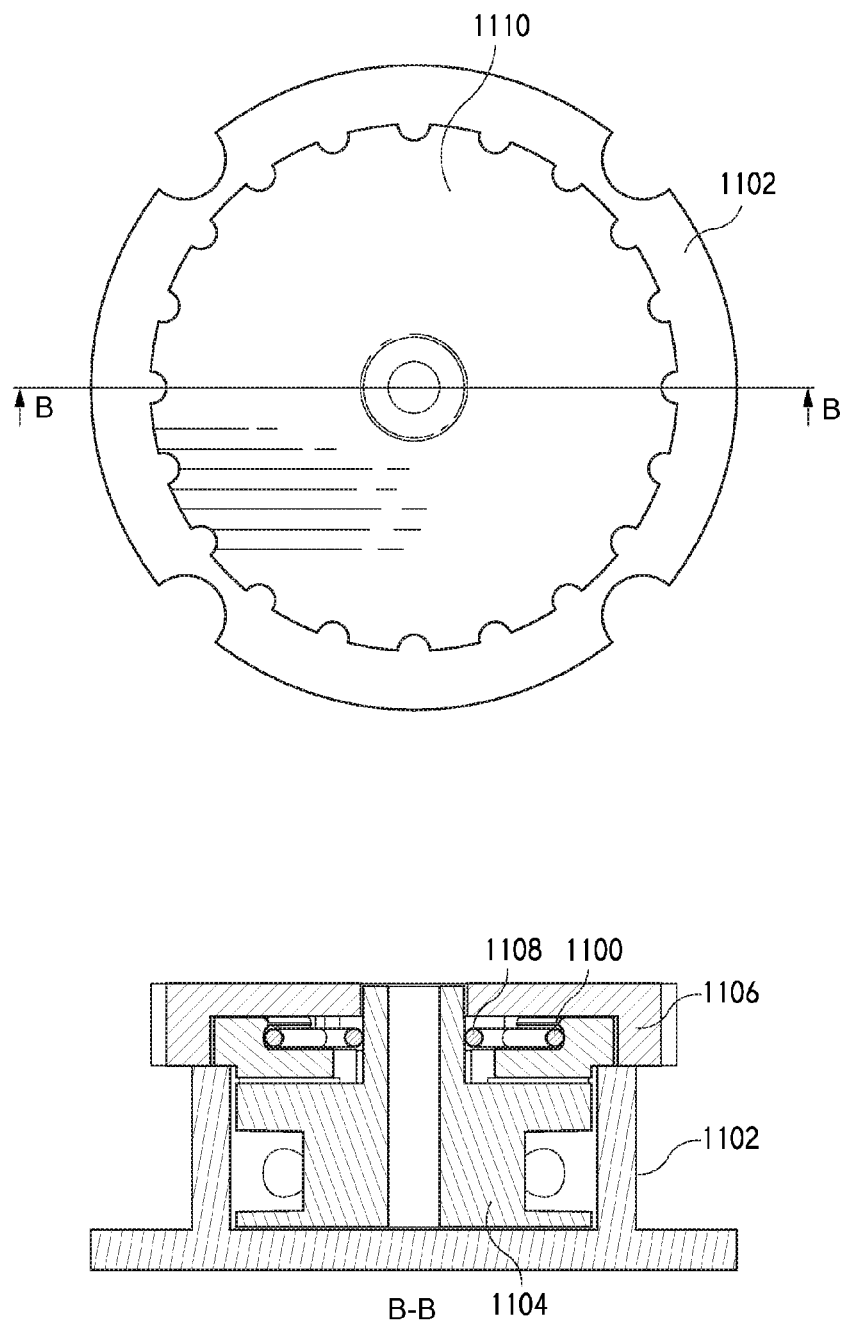
Figure 11C:
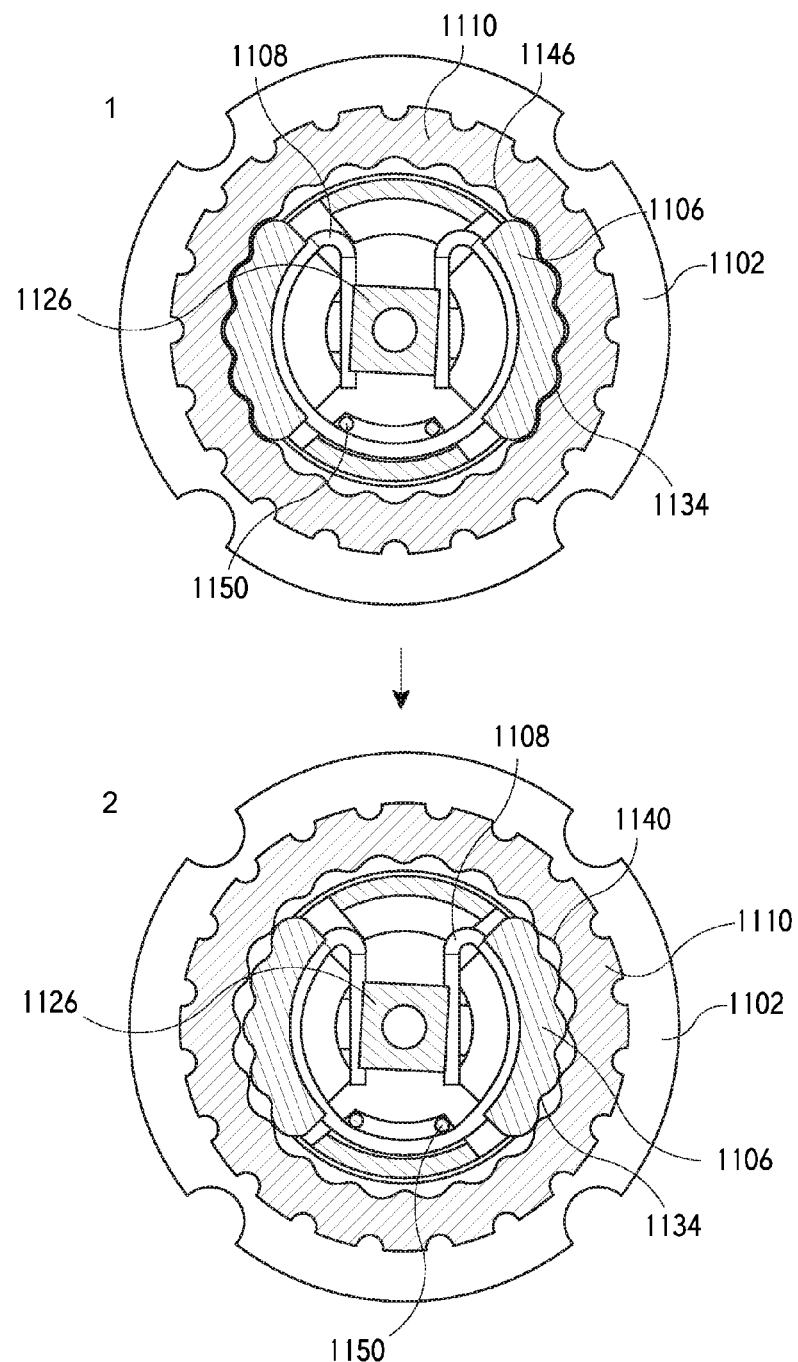

As shown in FIGS. 11A-C, illustrated is another embodiment of a closure device 1100 that includes a clutch or tension control mechanism. In some embodiments, device 1100 may be used to control the amount of torque that may be input or transferred to internal components of a closure system. Over-torqueing internal components of a closure device or system can lead to breakage of one or more of the internal components. To alleviate this problem, the internal components of closure systems are often designed and manufactured as relatively robust components. Stated differently, the components are designed and manufactured larger than needed merely to ensure that the components can handle the stress and/or fatigue associated with over-torqueing (i.e., the transfer of too much rotational stress to the internal components). Because device 1100 can reduce or prevent issues associated with over-torqueing, the components of closure systems can be designed and manufactured smaller than the components currently used, which may allow the closure system to exhibit improved performance and/or have a smaller size and profile.

Device 1100 is able to reduce or prevent issues associated with over-torqueing by using clutch components 1106 as described herein below. An advantage of the clutch components 1106 is that the components are configured or designed to work with conventional closure device systems. For example, the clutch components 1106 operably couple with spring 1108, which is a spring that is commonly used in conventional closure device systems. In the conventional closure systems, spring 1108 may function as the open and close mechanism that allows the system to be fully opened to release or loosen tension on the system's lace. In such embodiments, spring 1108 may expand and contract around a bushing to hold or maintain the closure system in an open configuration. The clutch components 1106 have a relatively low profile or configuration that allows the components 1106 to fit within an existing void or cavity of conventional closure systems. Further, the clutch components 1106 prevent or limits over-torqueing issues regardless of how the closure system's knob or tightening mechanism is rotated. Stated differently, the clutch components 1106 prevent over-torqueing when the closure system's knob is rotated in a tightening direction (e.g., clockwise) and when the knob is rotated in a loosening direction (e.g., counterclockwise). Exemplary closure systems in which the clutch components 1106 may be used are further described in U.S. patent application Ser. No. 11/263,253, filed Oct. 31, 2005, entitled "Reel Based Closure System," and U.S. patent application Ser. No. 13/098,276, filed Apr. 29, 2011, entitled "Reel Based Lacing System," the entire disclosures of which are incorporated by reference herein.

Referring again to FIGS. 11A-C, device 1100 includes a housing 1102 having an interior region within which one or more components of the device are positioned. Housing 1102 also includes a pair of lace ports 1112 through which lace (not shown) is inserted. A spool 1104 is positioned within the interior region of housing 1102. Spool 1104 is a simple representation of the internal components of a closure system and is not necessarily illustrative of all the internal system components that may be included. For example, closure systems often include a stop mechanism, such as a pawl disc or component, which is not illustrated in FIGS. 11A-C. Exemplary internal closure system components are described in U.S. application Ser. No. 11/263,253 and U.S. application Ser. No. 13/098,276 incorporated by reference herein above. The inclusion of spool 1104 is to represent such various internal mechanisms or components (e.g., stop mechanism and the like) of a closure system.

Spool 1104 includes an annular channel or recess 1122 around which the lace is wound as the device 1100 is operated by a user. Spool 1104 includes a central protrusion or bushing 1126 about which a spring 1108 is positioned. Spring 1108 includes two straight opposing ends that abut opposing planar surfaces of central protrusion 1126. The midsection of spring 1108 extends from the opposing straight ends in a semicircular or oval-like fashion. The midsection of spring 1108 is positioned between two pins 1150 and an opposing wall or axial protrusion 1124 of spool 1104 (see FIG. 11C), which function to hold the spring 1108 in position as the spring flexes radially inward and outward during operation of the device 1100.

A pair of clutch components 1106 are positioned atop spool 1104 and positioned on opposing sides thereof. Clutch components 1106 each include a central channel 1136 which is positioned atop a corresponding track 1128 of spool 1104. The tracks 1128 extends radially from the central protrusion 1126 and function to guide the clutch component 1106 in moving radially inward and outward during operation of the device 1100. The tracks 1128 also function to transfer rotational forces from the clutch components 1106 to the spool 1104 when a knob 1110 is rotated by a user. When the clutch components 1106 are positioned on top of the spool 1104, the spring 1108 is positioned on a top surface of the clutch components and within a channel or groove 1132. The spring 1108 biases the clutch components 1106 radially outward relative to spool 1104. The spring 1108 ensures that teeth 1134 of the clutch components 1106 are biased toward an engaged position with corresponding teeth 1146 of the knob component 1110, which is positioned atop and coaxially aligned with the housing 1102, spool 1104, and clutch components 1106.

Knob 1110 includes a central aperture 1144 through which a coupling component, such as a screw and the like, may be positioned to couple the various components of the device 1100 together. Knob 1110 also includes an outer surface 1142 that is configured to be gripped by a user. The outer surface 1142 may include a textured configuration that increases these friction between a user's hand and the knob 1110 or may include one or more materials, such as rubber, plastic, and the like, that increases the frictional resistance between the user's hand and the knob 1110. In some embodiments, the frictional material may be included as an over mold that is coupled with the knob 1110.

FIG. 11B illustrates a top and cross-sectional view of the assembled components of device 1100. FIG. 11C illustrates the device 1100 during operation. Specifically, as shown in the top view of FIG. 11C, with the teeth 1134 of clutch component 1106 engaged with the corresponding teeth 1146 of the knob 1110, rotation of the knob 1110 causes the spool 1104 to rotate via clutch components 1106 and tracks 1128. As the lace is tensioned via rotation of the spool 1104, the tension in the lace begins to counteract the rotational force input to knob 1110 by a user. As shown in the bottom figure of FIG. 11C, when a lace tension threshold is achieved or exceeded, the force exerted by the lace tension and the wave-like configuration of the teeth, 1134 and 1146, causes the clutch components 1106 to displace radially inward and out of engagement with the teeth 1146 of knob 1110. Spring 1108 then functions to bias the clutch components 1106 back into engagement with adjacent teeth 1146 of knob 1110. Further operation of the knob 1110 causes the clutch component 1106 to continually displace radially inward and outward, causing the clutch components teeth 1134 to skip into and out of engagement with the teeth 1146 of knob 1110. Counter-rotation of the knob 1110 will cause the lace tension to release or loosen.

In some embodiments, the clutch components 1106 may be incorporated into a device or conventional closure system that is configured to tighten an article, such as a shoe. In such embodiments, the device may include a housing having an interior region and a spool that is positioned within the interior region of the housing and rotatable relative thereto. A tightening mechanism, such as a knob, may be operably coupled with the spool to cause the spool to rotate within the interior region of the housing. A tension member, such as lace, may be coupled with the spool and configured to be tensioned upon rotation of the spool via the tightening mechanism. The clutch components 1106 may function as a force limiting mechanism that is configured to transfer tightening forces from the tightening mechanism to one or more internal components of the device, such as the spool, until a tightening force threshold is achieved. As described above, the clutch components 1106 may be further configured to not transfer tightening forces from the tightening mechanism to the one or more internal components of the device after the tightening force threshold is achieved.

As described herein, the clutch component may operationally engage with a spring that is positioned around a central protrusion or bushing. The spring may bias the clutch component toward an engaged position in which tightening forces are transferred to the one or more internal components. The clutch component may radially engage with the knob via the spring to transfer the tightening forces from the knob to the one or more internal components until the tightening force threshold is achieved, after which the clutch component may radially disengage from the knob so that the tightening forces are not transferred from the knob to the one or more internal components. The spring may be configured to maintain the device in an open position in which the tension member's tension is released or loosened. In some embodiments, the knob may be pulled axially upward and the spring may flex around the central protrusion or bushing to maintain the device in the open configuration. The clutch component may be positioned within a void or cavity axially below the knob.

Referring now to FIGS. 12A-E, illustrated is another embodiment of a device or closure system 1200 having a tension limiting component or mechanism. As shown in the exploded perspective view of FIG. 12B, system 1200 includes a housing 1202 having an interior region and a plurality of housing teeth 1230. In some embodiments the housing 1202 may have an open top end and an open bottom end while in other embodiments the housing 1202 may have a closed bottom end. A spool 1204 is positioned within the interior region of the housing 1202 and is rotatable relative thereto. Spool 1204 includes an annular channel (not numbered) around which a tension member or lace (not shown) is wound to tension the tension member. Spool 1204 also includes a plurality of axially oriented teeth 1232 that engage with corresponding axially oriented teeth 1234 of a core 1206 positioned axially above the spool 1204. Engagement of the teeth, 1232 and 1234, transfers rotational forces between the two components.

A plurality of pawl components 1208 are operationally coupled with the core 1206. Each pawl component 1208 includes pawl teeth 1236 that engage with the housing teeth 1230 of housing 1202 in a ratchet like fashion to allow the spool 1204 to be rotated within the housing's interior region in a first direction while preventing rotation of the spool 1204 in a second and opposite direction. In some embodiments, the core 1206 and pawl component 1208 may be replaced by a single component, such as a pawl disc. In other embodiments, the arrangement of the various teeth may be different. For example, radially oriented teeth may have an axial orientation and/or axially oriented teeth may have a radial orientation. In some embodiments, housing teeth 1230 may be replaced by a toothed component or disc that couples with the housing 1202.

A spring component 1210 is positioned axially above the pawl components 1208. Spring 1210 is similar to spring 1108 described above. Spring 1210 couples with a central bushing 1212 and is configured to maintain the system 1200 in an open configuration. System 1200 can be positioned in the open configuration by pulling axially upward on a knob component 1226, by pressing a button (not shown), by counter-rotating the knob component 1226 by a defined amount (e.g., ¼ to ½ counter-rotation), and the like. In some embodiments, spring 1210 may be replaced with a washer or other component having two or more stable positions, A screw or other fastener 1214 may couple the various components together. A further description of these components is included in U.S. application Ser. No. 13/098,276, which is incorporated by reference herein.

A cap component 1220 is positioned axially above the previously described components. The cap component 1220 is configured so that the core 1206 may couple with the cap component 1220. For example, various features of the core 1206 may snap into engagement with the cap component 1220 to couple the two components together. Because the core 1206 and cap component 1220 snap into engagement, or otherwise couple together, rotational forces input to the cap component 1220 are transferred to the core 1206. A toothed disc 1222 couples with the cap component 1220, such as by snapping together. The toothed disc 1222 includes radially inward oriented drive teeth 1242 that engage with corresponding radially outward oriented drive teeth 1240 of cap component 1220. Engagement of the drive teeth, 1242 and 1240, aids in transferring rotational forces between the two components.

A drive disc 1224 is positioned axially above the toothed disc 1222. Drive disc 1224 includes a pair of cantilevered arms 1254 that extend circumferentially from a main body of the disc 1224. Each cantilevered arm 1254 includes a tooth 1248 positioned on a distal end that is positioned within a corresponding axially oriented tooth 1250 or notch of toothed disc 1222. Engagement of the teeth, 1248 and 1250, of disc 1224 and 1222, respectively, transfers rotational forces between the two components. As described in greater detail below, the cantilevered arms 1254 are configured to axially flex when the tension threshold is achieved or exceeded to prevent further tensioning of the tension member or lace. Although FIG. 12B illustrates drive disc 1224 having a pair of cantilevered arms 1254 that each include axially oriented teeth 1248, it should be realized that in other embodiments more or fewer arms 1254 may be used. For example, in some embodiments, disc 1224 may include a single cantilevered arm 1254 or three or more cantilevered arms. Similarly, some or all of the arms 1254 could include radially oriented teeth that cause the arms to flex radially inward and outward.

As described in greater detail below, the drive disc 1224 and toothed disc 1222 function as a tension limiting mechanism that allows the tension member or lace to be tensioned via a tightening mechanism (e.g., knob component 1226) until a tension threshold is achieved, after which further operation of the tightening mechanism does not substantially tension the tension member or otherwise cause further tensioning of the tension member.

The knob component 1226 is positioned axially above the drive disc 1224. Knob component 1226 functions as a tightening mechanism that may be grasped and rotated by a user to tension the tension member or lace. Knob component 1226 is operably coupled with the spool 1204 via one or more of the components previously described. Rotation of the knob component 1226 causes the spool 1204 to rotate within the interior region of the housing 1202, which winds the tension member or lace around the spool's annular channel and thereby tensions the tension member or lace. Knob component 1226 also includes indicia 1260 that indicates the tension threshold of the system 1200 that may be set and/or adjusted as described below.

Figure 12C:
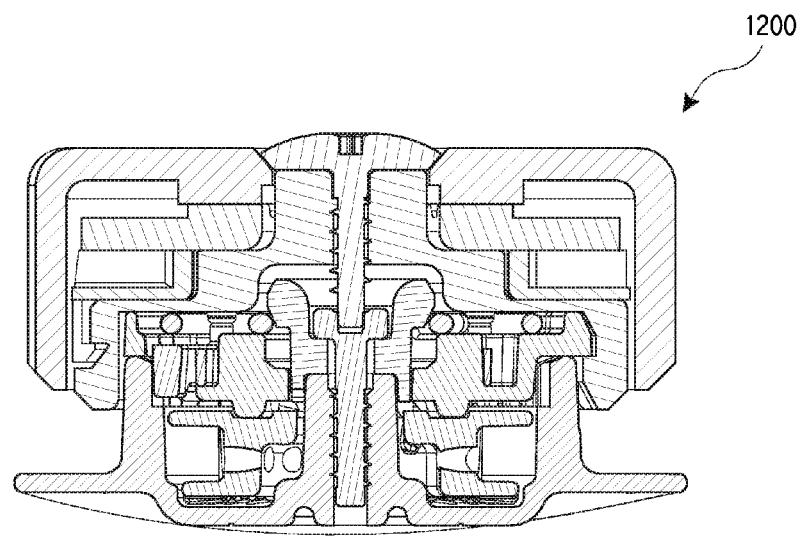

A fastener 1228, such as a screw, may be coaxially aligned with and inserted through an aperture of the knob 1226. The fastener 1228 may threadingly couple with a boss 1262 of cap component 1220 to couple the various component of system 1200 together. FIG. 12A shows an assembled perspective view of the system 1200 and FIG. 12C shows a cross section view of the assembled system.

Figure 12D:
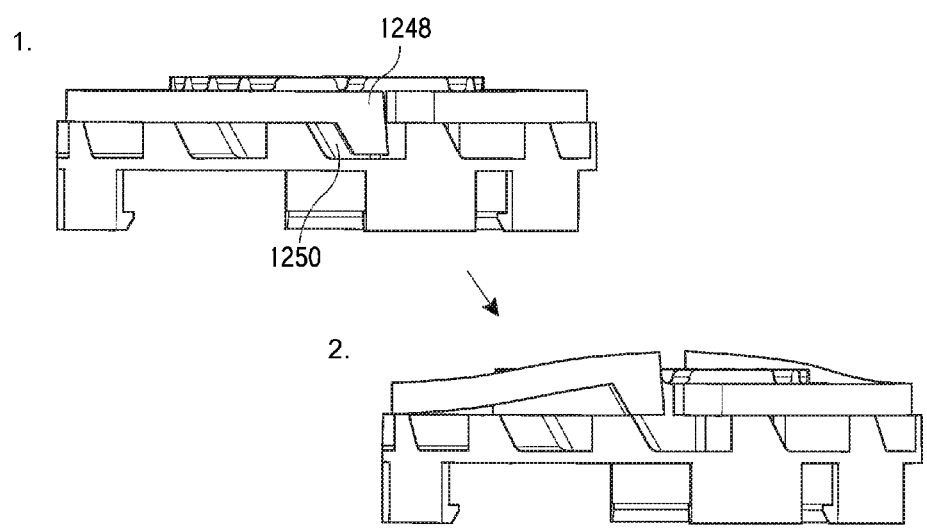
Figure 12E:
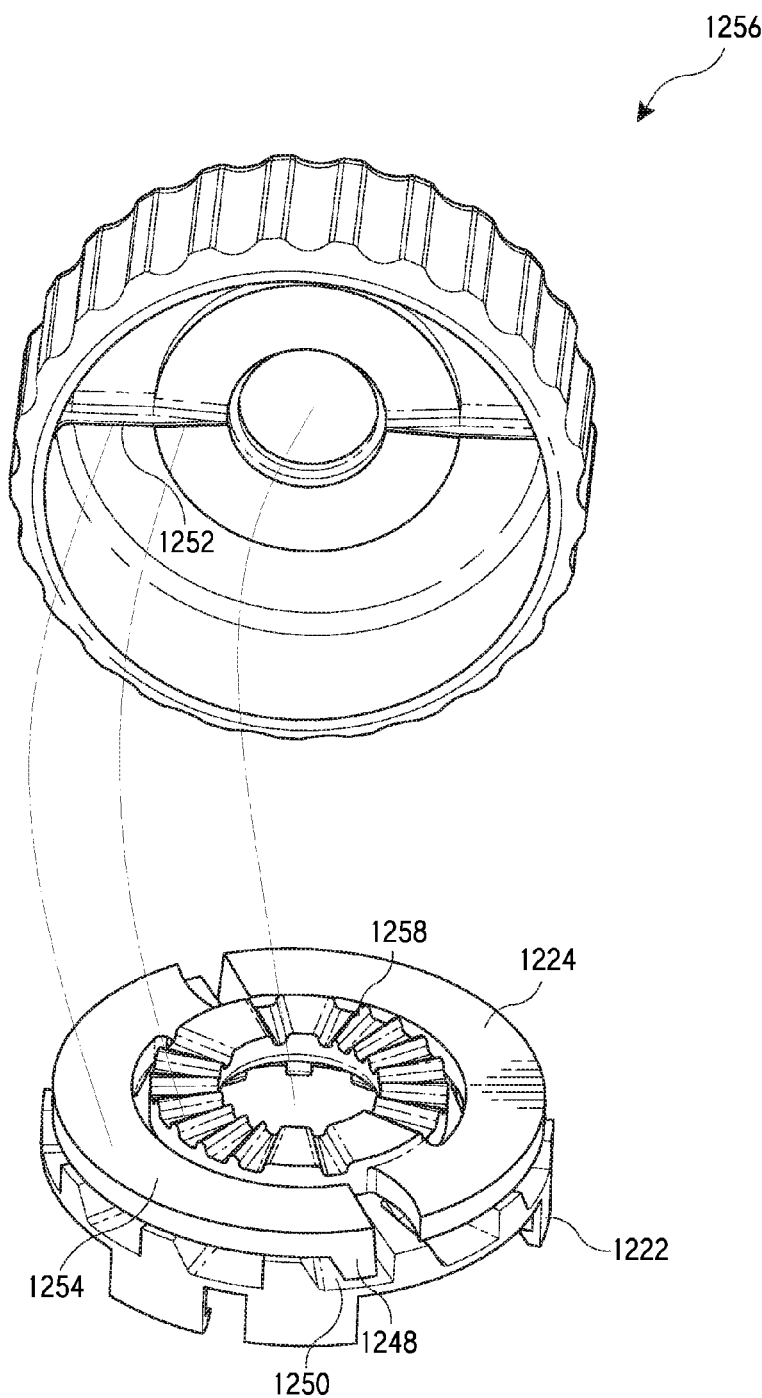

FIG. 12E shows a bottom perspective view of the knob component 1226 and a top perspective view of the drive disc 1224 and toothed component 1222. The bottom perspective view of the knob component 1226 shows a torque control member 1252 that is positioned on a bottom inner surface of the knob component 1226. The torque control member 1252 is used to adjust the tension threshold of the system 1200 by adjusting the flexibility of the cantilevered arms 1254. Specifically, the torque control member 1252 is a flange or other axially protruding member that is configured to be positioned atop the cantilevered arms 1254. As described previously in relation to FIGS. 8FF and 8GG, the position of the torque control member 1252 relative to the cantilevered arms 1254 varies the moment arm and bending moment of the arms 1254 and thus, varies the tension threshold in which the system 1200 will no longer tension the tension member or lace.

For example, when the torque control member 1252 is positioned near the proximal end of the arms 1254 and away from the tooth 1248, the flex of the arms 1254 is increased due to an increased moment arm and bending moment. This configuration allows the tooth 1248 to more easily deflect out of the notches 1250 of toothed disc 1222. As such, this configuration requires a relatively low tension threshold before further operation of the knob component 1226 will no longer tension the tension member or lace. In contrast, when the torque control member 1252 is positioned near the distal end of arms 1254 adjacent the tooth 1248, the flex of the arms 1254 is greatly decreased due to a decreased moment arm and bending moment. This configuration requires an increased input torque and/or lace tension force to cause the tooth 1248 to deflect out of the notches 1250 of toothed disc 1222. As such, this configuration requires a relatively high tension threshold before further operation of the knob component 1226 will no longer tension the tension member or lace. In some embodiments, the torque control member 1252 may be positioned axially above the teeth 1248 to prevent the teeth 1248 from deflecting out of the notches 1250. In this configuration, slippage of the drive disc 1224 and toothed disc 1222 may be essentially prevented. As such, this configuration ensures that operation of the knob component 1226 will essentially always tension the tension member or lace.

In some embodiments, a radial inward end of the torque control member 1252 may be positioned within radial grooves 1258 that are angularly positioned on the main body of the drive disc 1224. In some embodiments, the radial grooves 1258 may be relatively evenly spaced about the main body between an angle of between about 90 and 150 degrees. The radial grooves 1258 may be positioned so that a first radial groove is positioned near the proximal end of the cantilevered arms and a last radial groove is positioned near a distal end of the cantilevered arms adjacent the tooth 1248.

The position of the torque control member 1252 relative to the cantilevered arms 1254 may be changed by moving the knob component 1226 axially upward relative to the drive disc 1224 and repositioning the torque control member 1252. within a different radial groove 1258. In some embodiments the drive disc 1224 may include approximately 8 radial grooves that allow a user to set or vary the system 1200's tension threshold between 1 of 8 settings from a relatively low tension threshold to a relatively infinite threshold. In other embodiments the drive disc 1224 may include more or fewer radial grooves 1258 as desired. The indicia 1260 of knob component 1226 may correspond to the radial grooves 1258 to show the set tension threshold.

FIG. 12D illustrates the interaction of a tooth 1248 of the cantilevered arms and a notch 1250 of the toothed disc 1222. Specifically, the tooth 1248 engages with the notch 1250 and transfers a rotational force between the drive disc 1224 and toothed disc 1222. until the tension threshold is achieved or exceeded. After the tension threshold is achieved or exceeded, further rotation of the knob component 1226 causes the cantilevered arm 1254 to flex, which causes the tooth 1248 to axially deflect upward and out of the notch 1250. In this manner, rotation of the knob component 1226 causes the tooth 1248 to sequential skip of flex into and out of engagement with adjacent notches 1250 of the toothed component 1222, thereby preventing or limiting further tensioning of the tension member or lace via operation of the knob component 1226. In some embodiments, the drive component 1224 and toothed component 1222 may similarly operate when the knob component 1226 is counter-rotated.

In some embodiments, the system 1200 may also include a control mechanism that allows the tension member's tension to be substantially maintained upon tensioning of the tension member from a source other than the tightening mechanism. As used herein, the description of the tension member's tension being substantially maintained means that the tension member's tension is not substantially or significantly increased. The description may also mean that the tension member's tension is loosened to some degree. Likewise, the description of the tension member being tensioned from a source other than the tightening mechanism means that some other factor or component is causing an increase in the tension member's tension.

For example, in shoe applications, the tension member's tension may be increased as the user flexes their foot, engages in a sporting event, runs, walks, and the like. In such applications, the tension may also be increased due to swelling of the foot. In such embodiments, the control mechanism may function to prevent the tension member from being further tensioned. This tension limitation may be important to prevent injury to a body part, such as the development of ulcers in diabetic individuals due to swelling of the feet.

In some embodiments, the control mechanism may be disposed axially below a load holding element (e.g., pawl components 1208) that allows rotation of the spool in a first direction while preventing rotation of the spool in a second direction. This configuration is represented in previously described FIG. 6. In some embodiments, the control mechanism may have a non-linear bottom surface that frictionally engages with a non-linear top surface of the spool to transfer rotational forces between the control mechanism and spool and thereby tension the tension member until the tension threshold is achieved. The non-linear surfaces may also allow slippage of the spool relative to the control mechanism after the tension threshold is achieved so as to limit additional tensioning of the tension member. In such embodiments, the bottom surface of the control mechanism and the top surface of the spool may have a wave-like or sinusoidal shape as described above. In other embodiments, the non-linear bottom surface of the control mechanism and the non-linear top surface of the spool may be configured to frictionally engage as described above.

In some embodiments, the control mechanism may be a mechanism that is separate from the tension limiting mechanism, while in other embodiments the tension limiting mechanism and the control mechanism are the same. In embodiments where the control mechanism is separate from the tension limiting mechanism, the control mechanism may allow the spool 1204 to slip at a higher tension threshold then the tension limiting mechanism. This may be preferred in instance where greater tensions are preferred, but prevention of over-tensioning is still desired. For example, in diabetic shoes it may be preferred to allow some increase in the tension member's tension to prevent the shoes from becoming loose due to walking or running, while still preventing over-tensioning of the shoes from swelling. In some embodiments, the tension limiting mechanism may be disposed axially above the load holding element.

In some embodiments, a method for assembling a device for tightening an article may include providing a housing having an interior region and positioning a spool within the interior region of the housing so that the spool is rotatable relative to the housing. The method may also include operably coupling a tightening mechanism with the spool so that the spool is rotatable within the interior region of the housing upon operation of the tightening mechanism and coupling a tension member with the spool so that the tension member is tensionable upon rotation of the spool via the tightening mechanism. The method may further include operably coupling a tension limiting mechanism with the spool to enable the tension member to be tensioned via the tightening mechanism until a tension threshold is achieved, after which further operation of the tightening mechanism does not substantially tension the tension member.

In some embodiments, the method may additionally include providing the tightening mechanism with an indicator having indicia representative of a set tension threshold. In some embodiments, the method may additionally include coupling a control mechanism with the spool where the control mechanism is configured to allow the tension member's tension to be substantially maintained upon tensioning of the tension member from a source other than the tightening mechanism. In such embodiments, the control mechanism may be disposed axially below a load holding element that allows rotation of the spool in a first direction while preventing rotation of the spool in a second direction.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A reel for use with a lacing system for tightening an article comprising:
    a housing having an interior region;
    a spool positioned within the interior region of the housing and rotatable relative thereto, the spool having an annular channel formed therein;
    a knob rotatable relative to the housing and operably coupled with the spool to cause the spool to rotate within the interior region of the housing;
    a tension member coupled with the spool so as to be tensioned by winding the tension member around the spool's annular channel upon rotation of the knob;
    a tension control mechanism that is configured to enable tensioning of the tension member by rotation of the knob until a tension threshold is achieved, after which further rotation of the knob does not cause further tensioning of the tension member; and
    an adjustment mechanism that is operably coupled with the tension control mechanism and that is adjustable by a user to adjust the tension threshold upon which further rotation of the knob does not cause further tensioning of the tension member.

2. The reel of claim 1, wherein the adjustment mechanism includes an adjustment arm or member that is rotatable by the user to adjust the tension threshold.

3. The reel of claim 1, wherein the tension control mechanism is further configured to enable rotation of the spool within the housing's interior region upon tensioning of the tension member from a source other than the knob.

4. The reel of claim 1, wherein the tension control mechanism comprises a non-linear clutch mechanism that transfers a rotational force from the knob to the spool until the tension threshold is achieved, and wherein the non-linear clutch mechanism allows slippage of the spool after the tension threshold is achieved to limit additional tensioning of the tension member.

5. The reel of claim 4, wherein the non-linear clutch mechanism has a wave-like or sinusoidal shape.

6. The reel of claim 1, wherein the adjustment mechanism includes a spring member that biases a first component of the tension control mechanism toward a second component of the tension control mechanism, and wherein user adjustment of the adjustment mechanism comprises varying a biasing force of the spring member.

7. The reel of claim 6, wherein the adjustment mechanism further includes a lever arm that is rotatable by the user to vary the biasing force of the spring member.

8. The reel of claim 1, wherein the tension control mechanism comprises one or more cantilever arms that extend from a main body of the tension control mechanism and that engage with corresponding teeth of a spool driving mechanism to enable tensioning of the tension member by rotation of the knob until the tension threshold is achieved; and wherein the adjustment mechanism adjusts a flexibility of the one or more cantilever arms.

9. The reel of claim 6, wherein the spring member is replaceable such that user adjustment of the adjustment mechanism comprises replacing the spring member with another spring member having a different spring constant.

10. The reel of claim 6, wherein the adjustment mechanism further includes a detent, and wherein user adjustment of the adjustment mechanism comprises varying a position of the detent in relation to the spring member.

11. A reel device for tightening an article comprising:
    a housing having an interior region;
    a spool positioned within the interior region of the housing and rotatable relative thereto;
    a knob operably coupled with the spool to cause the spool to rotate within the interior region of the housing;
    a tension member coupled with the spool so as to be windable about the spool, the tension member being configured to be tensioned upon rotation of the spool via the knob; and
    a tension limiting mechanism that allows the tension member to be tensioned via the knob until a tension threshold is achieved, after which further operation of the knob does not substantially tension the tension member; and
    an adjustment mechanism that is adjustable by a user to adjust the tension threshold.

12. The reel device of claim 11, wherein the tension limiting mechanism is configured to allow the tension member's tension to be substantially maintained upon tensioning of the tension member from the article.

13. The reel device of claim 12, wherein the tension limiting mechanism is disposed axially below a load holding element that allows rotation of the spool in a first direction while preventing rotation of the spool in a second direction.

14. The reel device of claim 12, wherein the tension limiting mechanism comprises a non-linear clutch mechanism that transfers rotational forces between the tension limiting mechanism and spool until the tension threshold is achieved and that allows slippage of the spool relative to the tension limiting mechanism after the tension threshold is achieved.

15. The reel device of claim 14, wherein the tension limiting mechanism has a wave-like or sinusoidal shape.

16. The reel device of claim 11, wherein the adjustment mechanism includes an adjustment arm or member that is rotatable by the user to adjust the tension threshold.

17. The reel device of claim 11, wherein the tension limiting mechanism is disposed axially above a load holding element that allows rotation of the spool in a first direction while preventing rotation of the spool in a second direction.

18. The reel device of claim 11, wherein the adjustment mechanism includes a spring member, and wherein user adjustment of the adjustment mechanism comprises varying a biasing force of the spring member.

19. The reel device of claim 18, wherein the spring member biases opposing wave like or sinusoidal shaped members of the tension limiting mechanism into engagement.

20. The reel device of claim 18, wherein the adjustment mechanism further includes a lever arm that is rotatable by the user to vary the biasing force of the spring member.

21. The reel of claim 1, wherein the tension control mechanism is further configured to allow rotation of the spool within the housing's interior region upon tensioning of the tension member from the article.

22. The reel of claim 21, wherein the tension control mechanism comprises:
a first mechanism that enables tensioning of the tension member by rotation of the knob until the tension threshold is achieved; and
a second mechanism that enables rotation of the spool upon tensioning of the tension member from the source other than the knob.

23. The reel device of claim 11, wherein the tension limiting mechanism is configured to allow rotation of the spool within the housing's interior region upon tensioning of the tension member from the article.

* * * * *